US011203622B2

(12) United States Patent
Garred et al.

(10) Patent No.: US 11,203,622 B2
(45) Date of Patent: Dec. 21, 2021

(54) MASP ISOFORMS AS INHIBITORS OF COMPLEMENT ACTIVATION

(71) Applicants: Rigshospitalet, Copenhagen Ø (DK); Københavns Universitet, Copenhagen K (DK); Syddansk Universitet, Odense M (DK)

(72) Inventors: Peter Garred, Charlottenlund (DK); Tina Hummelshøj Glue, Søborg (DK); Mikkel-Ole Skjødt, Frederiksberg C (DK)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 15/609,660

(22) Filed: May 31, 2017

(65) Prior Publication Data

US 2017/0334961 A1    Nov. 23, 2017

Related U.S. Application Data

(63) Continuation of application No. 13/383,676, filed as application No. PCT/EP2010/060279 on Jul. 16, 2010.

(60) Provisional application No. 61/311,049, filed on Mar. 5, 2010.

(30) Foreign Application Priority Data

Jul. 17, 2009  (EP) .................................... 09165770
Oct. 1, 2009   (EP) .................................... 09171941

(51) Int. Cl.
  *C07K 14/47*         (2006.01)

(52) U.S. Cl.
  CPC ................................. *C07K 14/472* (2013.01)

(58) Field of Classification Search
  CPC .................................................. C07K 14/472
  See application file for complete search history.

(56) References Cited

U.S. PATENT DOCUMENTS

| | | | |
|---|---|---|---|
| 4,745,051 A | 6/1988 | Smith et al. | |
| 4,873,316 A | 10/1989 | Meade et al. | |
| 5,037,743 A | 8/1991 | Welch et al. | |
| 6,969,601 B2 | 11/2005 | Jensenius et al. | |
| 7,060,267 B2 | 6/2006 | Jensenius et al. | |
| 7,462,596 B2 | 12/2008 | Larsen et al. | |
| 2005/0032157 A1 | 2/2005 | Gal et al. | |
| 2007/0093443 A1* | 4/2007 | Madison | A61P 1/04 514/44 R |
| 2012/0058956 A1 | 3/2012 | Dahan et al. | |

FOREIGN PATENT DOCUMENTS

| | | |
|---|---|---|
| JP | 2003/515338 A | 5/2003 |
| JP | 2004-504027 A | 2/2004 |
| WO | WO 87/04464 A1 | 7/1987 |
| WO | WO 01/40451 A2 | 6/2001 |
| WO | WO 02/06460 A2 | 1/2002 |
| WO | WO 02/06460 A3 | 1/2002 |
| WO | WO 2007/047995 A2 | 4/2007 |

OTHER PUBLICATIONS

Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000; 10:398-400 (Year: 2000).*
Degn et al. Molecular Immunology. 2008; 45(16): 4137 (Year: 2008).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Bork.Powers and Pitfalls in Sequence Analysis: The 70% Hurdle. Genome Research, 2000; 10:398-400 (Year: 2000).*
Matsushita et al. Journal of Immunology. 164:2281-2284, 2000 (Year: 2000).*
Skjoedt et al. Crystal Structure and Functional Characterization of the Complement Regulator Mannose-binding Lectin (MBL)/Ficolin-associated Protein-1 (MAP-1). JBC, 2012; 287(39): 32913-32921 (Year: 2012).*
GENESEQ Database Accession No. AFY31045, "Complement-activating component of Fa-rective factor precursor V3 cDNA," Jul. 26, 2007, 3 pages.
GENESEQ Database Accession No. AFY31048, "Mannan-binding lectin serine protease 2 precursor protein VI," Jul. 26, 2007, 3 pages.
GENESEQ Database Accession No. AGE19338, "Human MBL-associated serine protease-2 CUBI-EGF-CUBII domai," Oct. 4, 2007, 3pages.
GENESEQ Database Accession No. AFY31046, "Complement-activating component of RA-reactive factor precursor V3," Jul. 26, 2007, 3 pages.
UNIPROT Database Accession No. B4DUI7_HUMAN, "Full-cDNA FLJ55004, highly similar to Comlement-act," Sep. 23, 2008, 2 pages.

(Continued)

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

The present invention relates to novel ficolin-associated polypeptides, and polypeptides derived from these ficolin-associated polypeptides for the use in the treatment of conditions associated with inflammation, apoptosis, autoimmunity, coagulation, thrombotic or coagulopathic related diseases, as well as the use as biomarkers. The present invention further relates to antibodies recognising such novel ficolin-associated polypeptides, and polypeptides derived thereof, nucleic acid molecules encoding such polypeptides, vectors and host cells used in the production of the polypeptides.

9 Claims, 36 Drawing Sheets

Figure 1:
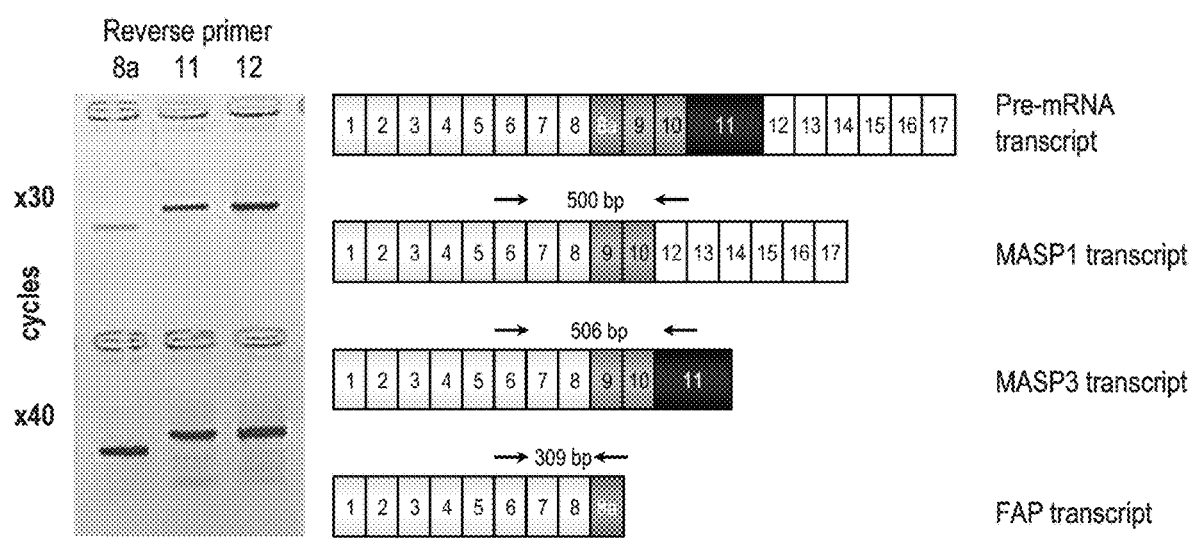

Specification includes a Sequence Listing.

(56) References Cited

OTHER PUBLICATIONS

Beinrohr, L., et al., "C1, MBL-MASPs and C1-inhibitor: novel approaches for targeting complement-mediated inflammation," *Trends in Molecular Medicine*, Dec. 2008, vol. 14(12), pp. 511-521.
Bowie, J., et al., "Deciphering the Message in Protein Sequences: Tolerance to Amino Acid Substitutions," *Science*, 1990, vol. 247, pp. 1306-1310.
Degn, S., et al., "Expression of various serine protease constructs of MASP-1 and -3 reaffirms the importance of the signal peptide in determining recombinant protein yields," *Molecular Immunology*, 2008, vol. 45(16), p. 4137, abstract P125.
European Examination Report for European PatentApplication No. 10737833.3, dated May 12, 2015.
Fujita, Teizo, "Evolution of the Lectin-Complement Pathway and Its Role in Innate Immunity," *Nature Reviews|Immunology*, May 2002, vol. 2(5), pp. 346-353.
Fujita, T., et al., "The lectin-complement pathway—its role in innate immunity and evolution," *Immunological Reviews*, Apr. 2004, vol. 198, pp. 185-202.
GENESEQ Database Accession No. AFY31046, "Method of modulating complement activation comprises contacting a non-complement protease with target substrates of a complement pathway," Jul. 27, 2007, two pages.
GENESEQ Database Accession No. AGE19338, "Inhibiting in a subject mannan-binding lectin-associated serine protease 2 (MASP-2)-dependent complement activation for treating or preventing e.g., atherosclerosis by administering a MASP-2 inhibitory agent," Oct. 4, 2007, two pages.
Hummelshoj, T., et al., "Molecular organization of human Ficolin-2," *Molecular Immunology*, 2007, vol. 44, pp. 401-411.
Iwaki, D., et al., "Small Mannose-Binding Lectin-Associated Protein Plays a Regulatory Role in the Lectin Complement Pathway," *The Journal of Immunology*, 2006, vol. 177(12), pp. 8626-8632.
Japanese Application No. 2012-555437, Non-Final Rejection dated Apr. 21, 2015.
Liu, T., et al., "Human Plasma N-Glycoproteome Analysisby Immunoaffinity Subtraction, Hydrazide Chemistry, and Mass Spectrometry," *Journal of Proteome Research*, 2005, vol. 4, pp. 2070-2080.
Makrides, Savvas C., "Therapeutic Inhibition of the Complement System," *Pharmacological Reviews*, 1998, vol. 50(1), pp. 59-88.
Matsushita, M., et al., "Cutting Edge: Complement-Activating Complex of Ficolin and Mannose-Binding Lectin-Associated Serine Protease," *The Journal of Immunology*, 2000, vol. 164, pp. 2281-2284.
Skjoedt, M., et al., "A Novel Mannose-binding Lectin/Ficolin-associated Protein is Highly Expressed in Heart and Skeletal Muscle Tissues and Inhibits Complement Activation," *The Journal of Biological Chemistry*, Mar. 2010, vol. 285(11), pp. 8234-8243.
Teillet, F., et al., "Crystal Structure of the $CUB_1$-EGF-$CUB_2$ Domain of Human MASP-1/3 and Identification of Its Interaction Sites with Mannan-binding Lectin and Ficolins," *The Journal of Biological Chemistry*, 2008, vol. 283(37), pp. 25715-25724.
UNIPROT Database Accession No. MASP2_HUMAN, "Full= Mannan-binding lectin serine protease 2; EC=3.4.21.104," May 30, 2000, pp. 1-10.
UNIPROT Database Accession No. AK300663, "Homo sapiens cDNA FLJ55004 complete cds, highly similar to Complement-activating component of Ra-reactive factor precursor (EC 3.4.21.-)," Jul. 31, 2008, pp. 1-2.
Wallis, Russell, "Interactions between mannose-binding lectin and MASPs during complement activation by the lectin pathway," *Immunobiology*, 2007, vol. 212, pp. 289-299.
Whisstock, J., et anon., "Prediction of protein function from protein sequence and structure," *Quarterly Reviews of Biophysics*, 2003, vol. 36(3), pp. 307-340.
GENBANK Accession No. AAH39724.1, "MASP1 protein, partial [*Homo sapiens*]," 2005, pp. 1-3.

\* cited by examiner

FIG. 4

FIG. 5

| Immobilized ligand | Soluble analyte | $K_{on}$ (M$^{-1}$ s$^{-1}$) | $K_{off}$ (s$^{-1}$) | $K_D$ (nM) |
|---|---|---|---|---|
| rFicolin-2 | MASP-1 | $8.9 \times 10^4$ | $4.4 \times 10^{-4}$ | 5.0 |
| rFicolin-2 | MASP-3 | $1.0 \times 10^5$ | $3.0 \times 10^{-4}$ | 2.9 |

FIG. 11

24A

| Immunoprecipitated with | mAb-MASP-1/3 | mAb-MAP-1 | mAb-MASP-1/3 | mAb-MAP-1 | mAb-MASP-1/3 | mAb-MAP-1 | MW |
|---|---|---|---|---|---|---|---|
| | | | | | | | ◄ 75kD |
| MAP-1 ► | | | | | | | ◄ 50kD |
| Ficolin-3 ► | | | | | | | ◄ 37kD |
| MBL ► | | | | | | | |
| | | | | | | | ◄ 25kD |
| Western blot detected with | pAb-MAP-1 | | mAb-Ficolin-3 | | mAb-MBL | | |

24B

| Immunoprecipitated with | mAb-MBL | mAb-Ficolin-2 | mAb-Ficolin-3 | mAb-MAP-1 + rMAP-1 | mAb-MAP-1 + sMAP-1 | |
|---|---|---|---|---|---|---|
| MW | | | | | | |
| 50kD ► | | | | | | ◄ MAP-1 |
| 37kD ► | | | | | | |
| 25kD ► | | | | | | |
| Western blot detected with | | | pAb-MAP1 | | | |

FIG. 24

31B

MASP ISOFORMS AS INHIBITORS OF COMPLEMENT ACTIVATION

CROSS-REFERENCE TO RELATED APPLICATIONS

This application is a continuation of U.S. application Ser. No. 15/609,660, filed May 31, 2017, which is a U.S. National Phase Application of PCT/EP2010/060,279, filed Jul. 16, 2010, which International Application was published by the International Bureau in English on Jan. 20, 2011, and application claims priority from U.S. Provisional Patent Application No. 61/311,049, filed Mar. 5, 2010, European Application No. 09171941.9, filed Oct. 1, 2009, and European Application No. 09165770.0, filed Jul. 17, 2009, which applications are hereby incorporated in their entirety by reference in this application.

FIELD OF THE INVENTION

The present invention relates to novel ficolin-associated polypeptides, and polypeptides derived from these ficolin-associated polypeptides for the use in the treatment of conditions associated with inflammation, apoptosis, autoimmunity, coagulation, thrombotic or coagulopathic related diseases, as well as the use as biomarkers. The present invention further relates to antibodies recognising such novel ficolin-associated polypeptides, and polypeptides derived thereof, nucleic acid molecules encoding such polypeptides, vectors and host cells used in the production of the polypeptides.

BACKGROUND OF THE INVENTION

Activation of the complement system (C) is accomplished via three different initiation pathways: The alternative (AP), the classical (CP), or the lectin pathway (LCP). AP activation occurs on foreign surfaces and is caused by a slow, spontaneous hydrolysis of C3 and the activity of the factors properdin, factor B and factor D to form the functional C3 convertase C3bBb. AP also functions as an amplification pathway (the amplification loop) of the two other pathways. Recently it has been shown that the alternative convertase assembly may also be initiated by non-covalent attachment of properdin to some target surfaces. CP activation on the other hand is initiated when C1q binds to immunoglobulins in complex with antigens, which triggers the activation of the C1q-associated serine proteases C1r and C1s. C1s cleaves and activates C4 and C2 to form the CP C3 convertase C4b2a. The LCP is activated when mannose-binding lectin (MBL) or ficolins binds to restricted patterns of carbohydrates or acetylated compounds e.g. on the surface of microorganisms or when exposed on dying host cells. Upon binding to the ligand the associated serine protease MASP-2 activates and cleaves C4 and C2 to form the LCP C3 convertase C4b2a. The function of MASP-1 has been suggested to involve a stabilization of MASP-2 cleavage of C2 and also direct low grade cleavage of C3. Yet other studies relate the function and activity of MASP-1 and MASP-2 to a coagulation system cross-talk involving prothrombin, fibrinogen and factor XIII. Using MASP1/3 knockout mice it was recently demonstrated that MASP-1 in fact contributes to the complement activity. The exact function of the most recently discovered MBL associated serine protease MASP-3 has yet to be elucidated. Studies indicating that MASP-3 associates with a limited range of MBL oligomers and that MASP-3 and the small MBL-associated protein (sMAP) are involved in regulation or inhibition of MBL dependent LCP complement activation have been reported.

MASP-1 and -3 are derived from the same MASP1/3 gene (present on chromosome 3q27-q28) through differential splicing. They contain an identical A-chain except for 15 C-terminal residues. The A chain is comprised of two CUB (C1r/C1s, Urchin-EGF, Bone morphogenetic protein) domains separated by an EGF (Epidermal Growth Factor) domain and followed by two CCP domains (complement control protein). The B-chain including the serine protease domain is different for MASP-1 and MASP-3. The MASP-2 and sMAP are also derived from the same gene (present on chromosome 1p36-p36.2) where sMAP is a truncated form lacking the serine protease domain and a major part of the A-chain. The MASP1/3 gene has been shown to be polymorphic, but the functional importance of this is still poorly understood. However, there is some evidence that polymorphisms in the MASP2/sMAP gene are associated with increased risk of infections. Expression of the MASPs is localized to liver hepatocytes, but a recent study described that human MASP-3 mRNA (as the only MASP-mRNA) was expressed in a broad range of tissues.

OBJECT OF THE INVENTION

It is an object of embodiments of the invention to provide polypeptides suitable for the treatment of conditions associated with inflammation, apoptosis, autoimmunity, coagulation, and/or thrombotic or coagulopathic related diseases. The polypeptides of the invention may further be suitable as biomarkers for the diagnosis and/or prognosis of these indications as well as for malignant diseases, such as cancers.

SUMMARY OF THE INVENTION

It has been found by the present inventor(s) that novel polypeptides that associate with the recognition molecules of the lectin complement pathway as well as polypeptides, such as fragments derived thereof may be used in the treatment of specific medical conditions associated with inflammation, apoptosis, autoimmunity, coagulation, and/or thrombotic or coagulopathic related diseases.

So, in a first aspect the present invention relates to an isolated ficolin-associated polypeptide.

In a second aspect the present invention relates to a polypeptide comprising the amino acid sequence of SEQ ID NO:4 or variants or immunologic fragment thereof.

In a third aspect the present invention relates to an antibody that specifically binds a polypeptide according to the invention.

In a fourth aspect the present invention relates to an isolated nucleic acid molecule encoding a polypeptide according to the invention.

In a further aspect the present invention relates to an isolated nucleic acid molecule comprising a nucleotide sequence that is at least 70% identical to the sequence of SEQ NO: 2.

In a further aspect the present invention relates to a vector comprising an isolated nucleic acid molecule encoding a polypeptide according to the invention.

In a further aspect the present invention relates a host cell comprising a vector comprising an isolated nucleic acid molecule encoding a polypeptide according to the invention.

In a further aspect the present invention relates a method for producing the polypeptide according to the invention, the method comprising cultivating a cell according to the invention in an appropriate growth medium under conditions allowing expression of the polynucleotide construct and recovering the resulting polypeptide from the culture medium.

In a further aspect the present invention relates a composition comprising a polypeptide according to the invention.

In a further aspect the present invention relates a pharmaceutical composition comprising a polypeptide according to the invention.

In a further aspect the present invention relates a method for detecting a polypeptide according to the present invention in a biological sample, the method comprising:
a) obtaining a biological sample;
b) contacting the biological sample with an antibody according to the invention; and
c) detecting complexes of the antibody and the polypeptide, if any;

as an indication of the presence of the polypeptide in the sample.

In a further aspect the present invention relates a polypeptide according to the invention for use as a medicament.

In a further aspect the present invention relates to the use of a polypeptide according to the present invention; for the preparation of a medicament.

In a further aspect the present invention relates to a polypeptide according to the present invention for the treatment of any indications associated with inflammation, apoptosis and/or autoimmunity.

In a further aspect the present invention relates to a polypeptide according to the present invention for the treatment of any indications associated with coagulation, thrombotic or coagulopathic related diseases.

In a further aspect the present invention relates to a polypeptide according to the present invention for preventing the occurrence of thromboembolic complications in identified high risk patients, such as those undergoing surgery or those with congestive heart failure.

In a further aspect the present invention relates to a polypeptide according to the present invention for the treatment of medical condition associated with the heart.

In a further aspect the present invention relates to a polypeptide according to the present invention for the treatment of a medical condition associated with a deficiency in a ficolin-associated polypeptide.

In a further aspect the present invention relates to a method for the treatment of any indication associated with inflammation, apoptosis and/or autoimmunity; the method comprising administering a therapeutically or prophylactically effective amount of a polypeptide according to the invention to a subject in need thereof.

In a further aspect the present invention relates to a method for the treatment of any indication associated with coagulation, thrombotic or coagulopathic related diseases; the method comprising administering a therapeutically or prophylactically effective amount of a polypeptide according to the present invention to a subject in need thereof.

In a further aspect the present invention relates to a method for preventing the occurrence of thromboembolic complications in identified high risk patients, such as those undergoing surgery or those with congestive heart failure; the method comprising administering a therapeutically or prophylactically effective amount of a polypeptide according to the present invention to a subject in need thereof.

In a further aspect the present invention relates to a method for the treatment of a medical condition associated with the heart; the method comprising administering a therapeutically or prophylactically effective amount of a polypeptide according to the present invention to a subject in need thereof.

In a further aspect the present invention relates to a method for the treatment of a medical condition associated with a deficiency in a ficolin-associated polypeptide; the method comprising administering a therapeutically or prophylactically effective amount of a polypeptide according to the present invention to a subject in need thereof.

In a further aspect the present invention relates to a nucleic acid probe capable of hybridizing under stringent conditions to a nucleic acid sequence encoding a polypeptide according to the present invention.

In a further aspect the present invention relates to a method of detecting the presence of a nucleic acid encoding a polypeptide according to the present invention in a biological sample, the method comprising
a) obtaining a biological sample;
b) contacting the biological sample with a nucleic acid probe according to the present invention; and
c) detecting complexes of the a nucleic acid probe and the nucleic acid encoding the polypeptide, if any;

as an indication of the presence of the nucleic acid encoding the polypeptide in the sample.

In a further aspect the present invention relates to a method for diagnosing a disorder associated with aberrant expression of a ficolin-associated polypeptide, comprising obtaining a biological sample from a patient and measuring the expression in the biological sample of the ficolin-associated polypeptide, wherein increased or decreased expression of the ficolin-associated polypeptide in the biological sample compared to a control indicates that the patient suffers from a disorder associated with aberrant expression of a ficolin-associated polypeptide.

In a further aspect the present invention relates to an isolated composition comprising the combination of a polypeptide according to the present invention together with one or more proteins selected from Ficolin-1, 2, 3, mannose-binding lectin (MBL), C1q, lung surfactant proteins SP-A and/or SP-D, and intracellular collagen-like defense molecules, such as CLL-11.

In a further aspect the present invention relates to a composition comprising a polypeptide according to the present invention, which is a pharmaceutical composition.

In a further aspect the present invention relates to a pharmaceutical composition according to the present invention for use as a medicament.

In a further aspect the present invention relates to the use of a composition according to the present invention; for the preparation of a medicament.

In a further aspect the present invention relates to a pharmaceutical composition according to the present invention for the treatment of any indications associated with inflammation, apoptosis and/or autoimmunity.

In a further aspect the present invention relates to a pharmaceutical composition according to the present invention for the treatment of any indication as defined herein.

In a further aspect the present invention relates to a method for the treatment of any indication as defined herein, the method comprising simultaneously or sequentially administering a therapeutically or prophylactically effective amount of a polypeptide according to the present invention and one or more proteins selected from Ficolin-1, 2, 3, and mannose-binding lectin (MBL), C1q, lung surfactant proteins SP-A and/or SP-D, and intracellular collagen-like defense molecules, such as CLL-11.

In a further aspect the present invention relates to the use of a polypeptide according to the present invention as a biomarker in the blood and tissue for the diagnosis and/or prognosis of a malignant disease, such as a cancer disease, such as brain tumors, liver tumors and tumors in the reproductive tract.

In a further aspect the present invention relates to the use of a polypeptide according to the present invention as a biomarker in blood and tissue for diagnosis and/or prognosis of an autoimmune, metabolic and/or inflammatory condition as defined herein.

LEGENDS TO THE FIGURES

FIG. 1: Alternative transcription of the MASP-1 gene. Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). MASP1 generates a fragment of 500 bp, MASP3 generates a fragment of 506 bp and FAP generates a fragment of 309 bp.

Figure 2:
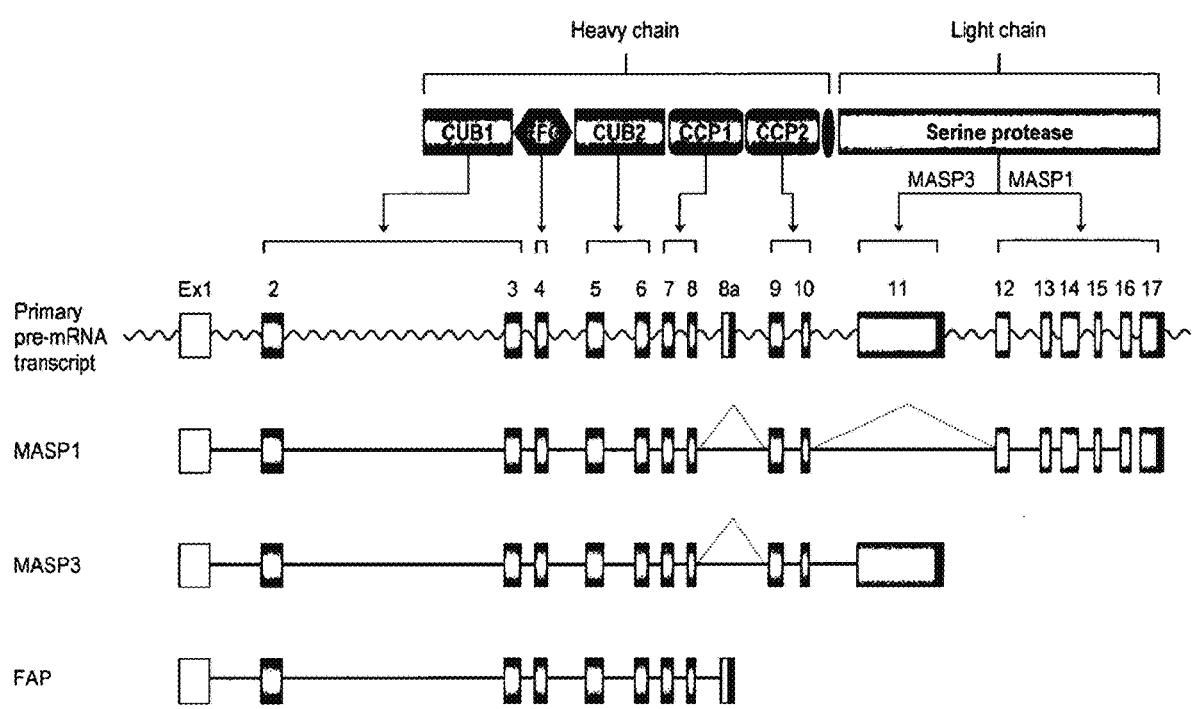

FIG. 2: Alternative splicing of the MASP1 gene. MASP1 is generated by splicing out of 8a and exon 11, which both contain a stop codon sequence (marked with black boxes). The MASP1 sequence contains a stop codon in exon 17. MASP3 is generated by splicing out of exon 8a and FAP is generated if no splicing out of exon 8a occurs. The FAP protein contains the two CUB domains, the EFG domain and the first CCP1 domain.

Figure 3:
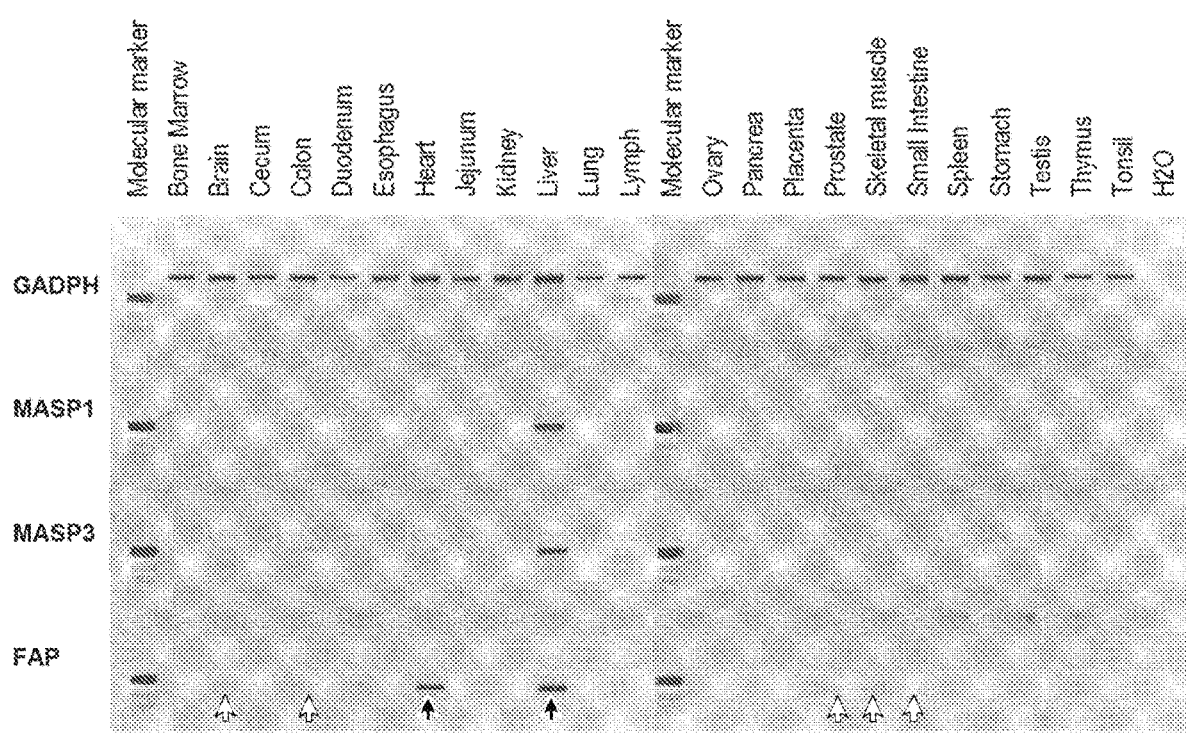

FIG. 3: Tissue expression of the FAP fragment. The tissue distributions of the MASP-1, MASP3, and FAP genes were investigated in cDNA panels from Clontech. MASP-1, MASP-3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

Figure 4:
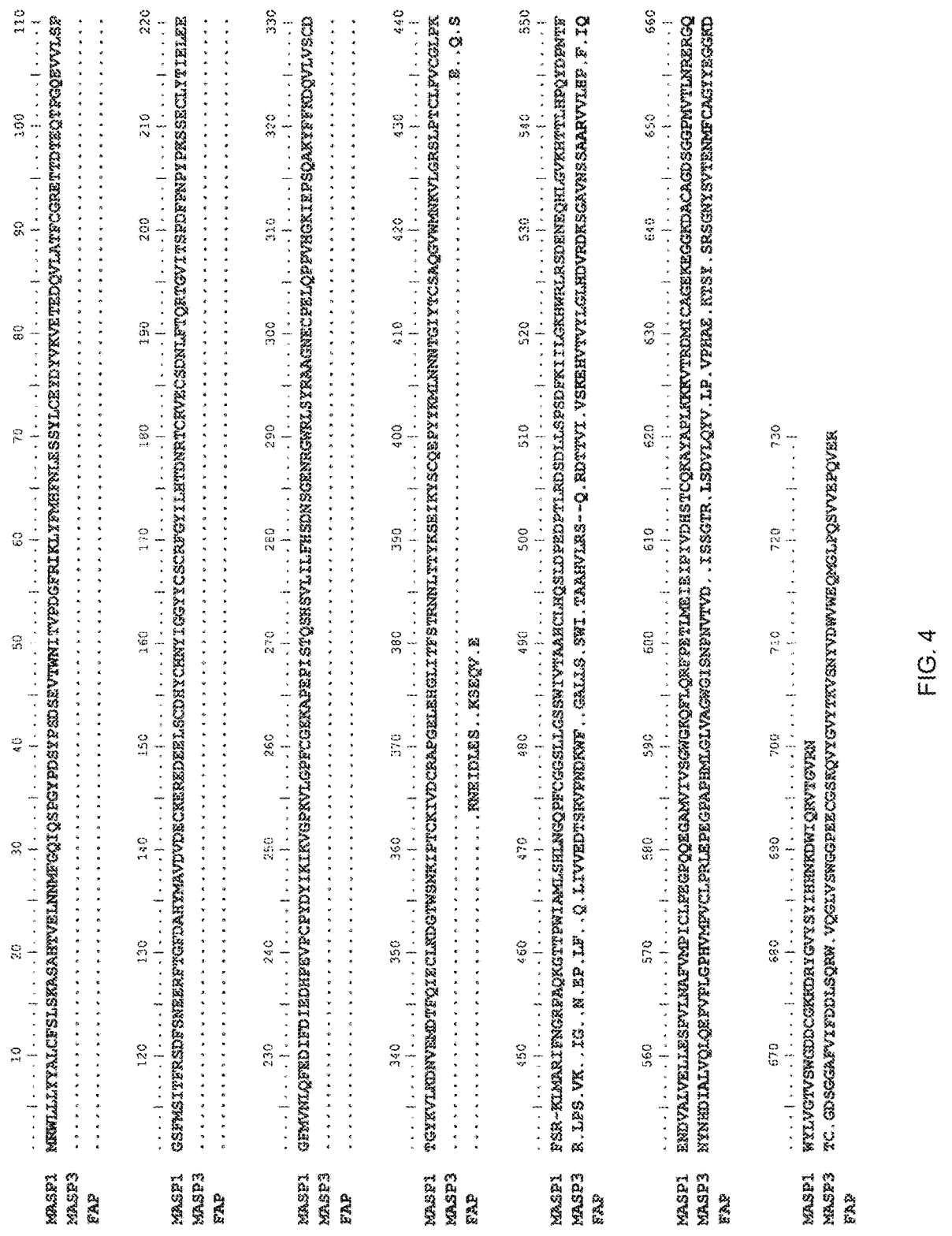

FIG. 4: Alignment of MASP-1, MASP-3, and FAP. The protein sequences of MASP-1, MASP-3, and FAP were aligned using the BioEdit Software. MASP-1 and MASP-3 contain different C-terminal serine protease domains whereas FAP does not contain any serine protease domain. Instead the protein contains 17 new amino acids in the C-terminal region.

Figure 5:
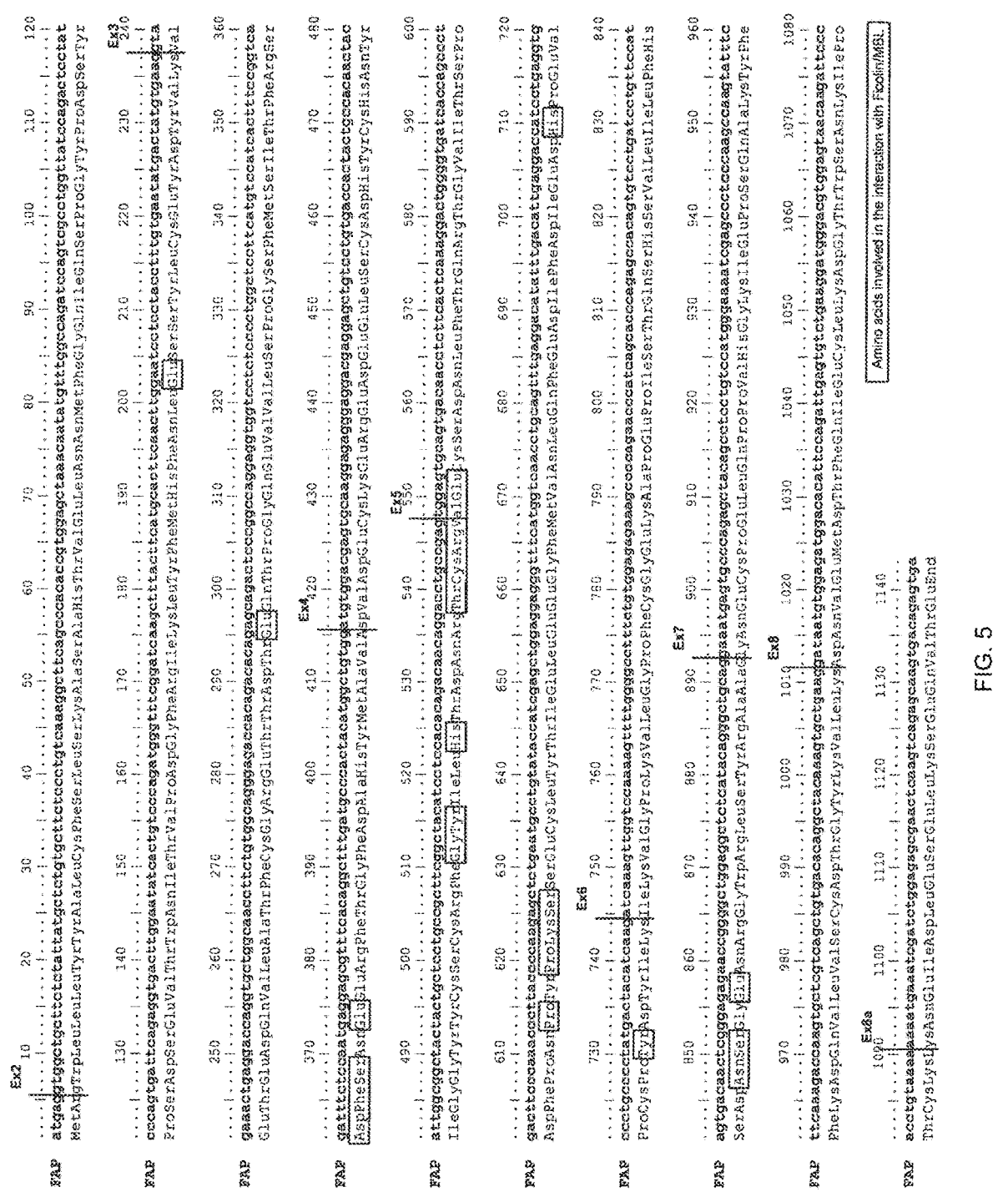

FIG. 5: cDNA sequence and corresponding protein sequence of FAP. The cDNA sequence is shown in the upper row and the corresponding protein sequence is shown below. Exons regions are divided by black vertical lines. Amino acids believed to be involved in the binding to MBL/ficolins are marked with light-yellow boxes.

Figure 6:
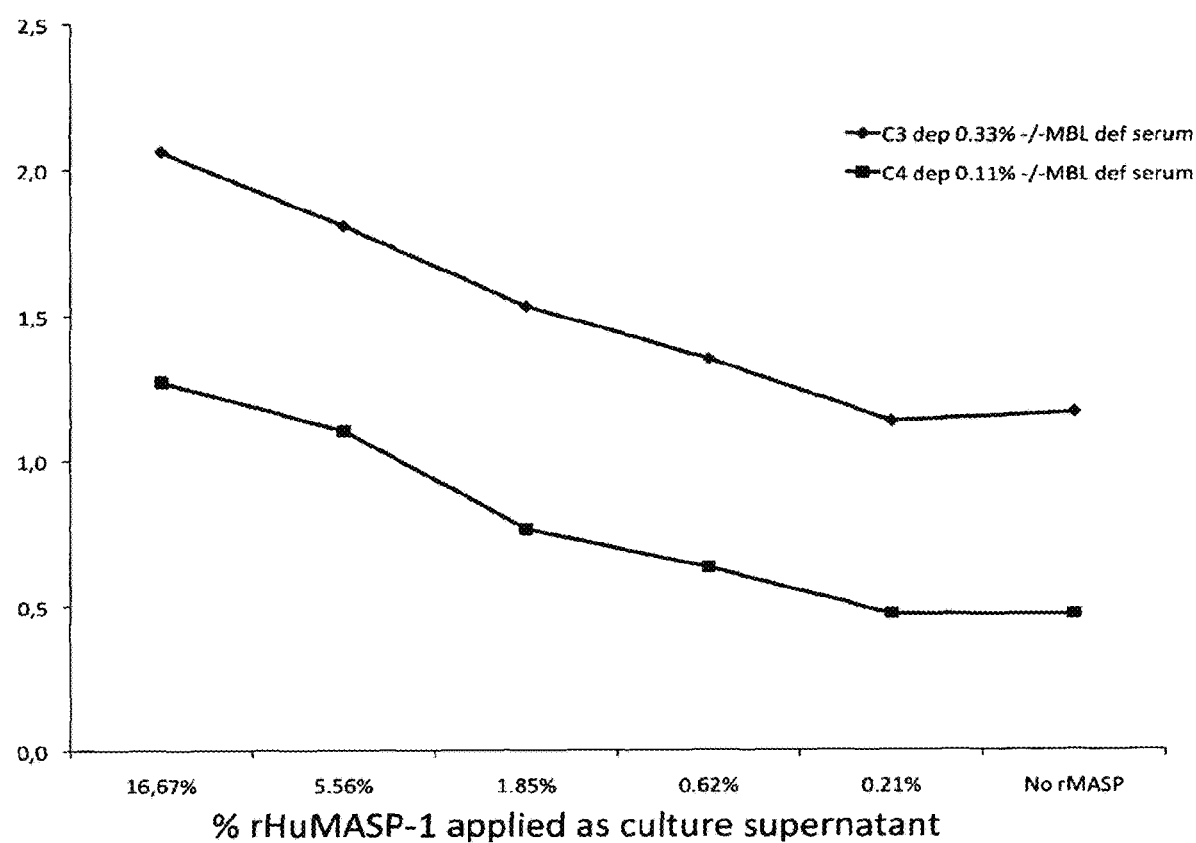

FIG. 6: MASP-1 complement activation. Human MBL were incubated with increased amount of MASP-1. MASP-1 were able to activate both the C3 and C4 complement proteins.

Figure 7:
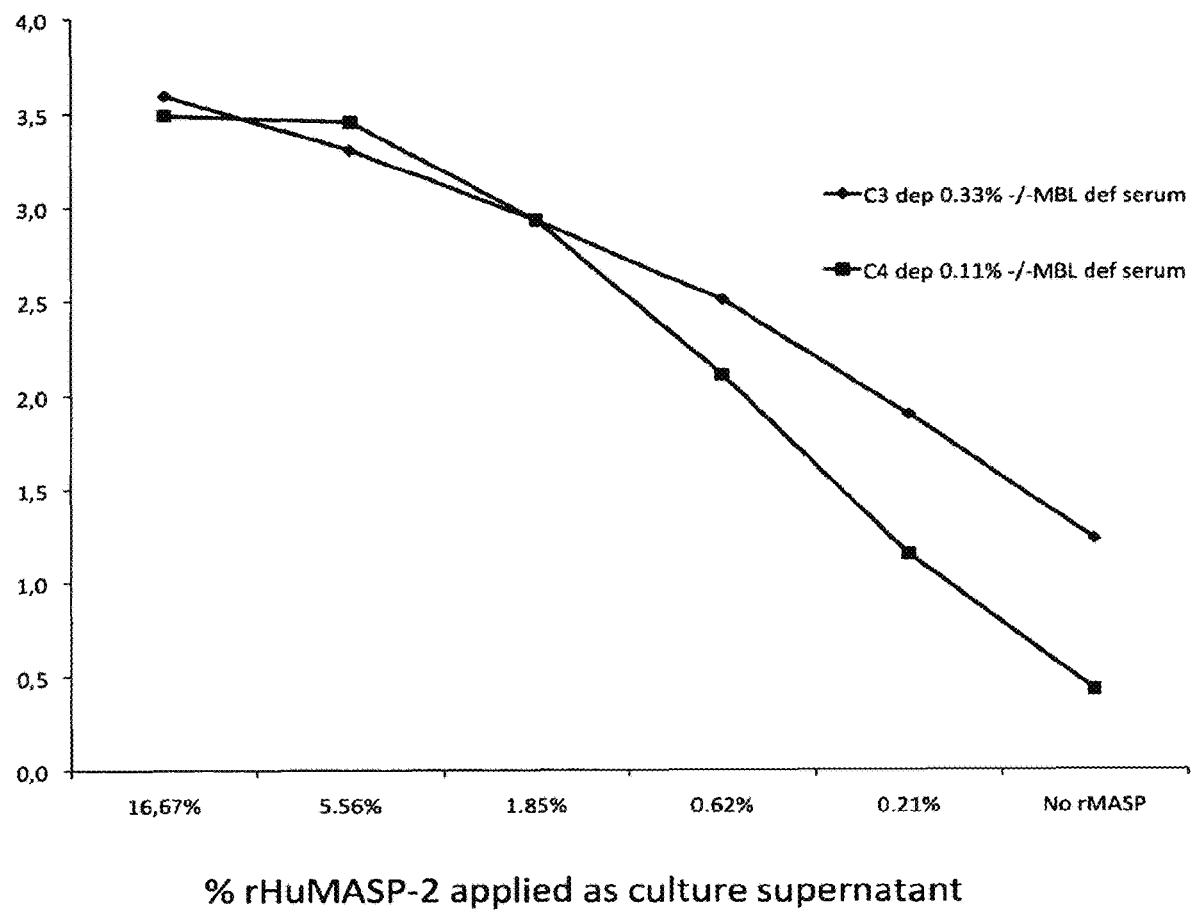

FIG. 7: MASP-2 complement activation. Human MBL were incubated with increased amount of MASP-2. MASP-2 were able to strongly activate both the C3 and C4 complement proteins.

Figure 8:
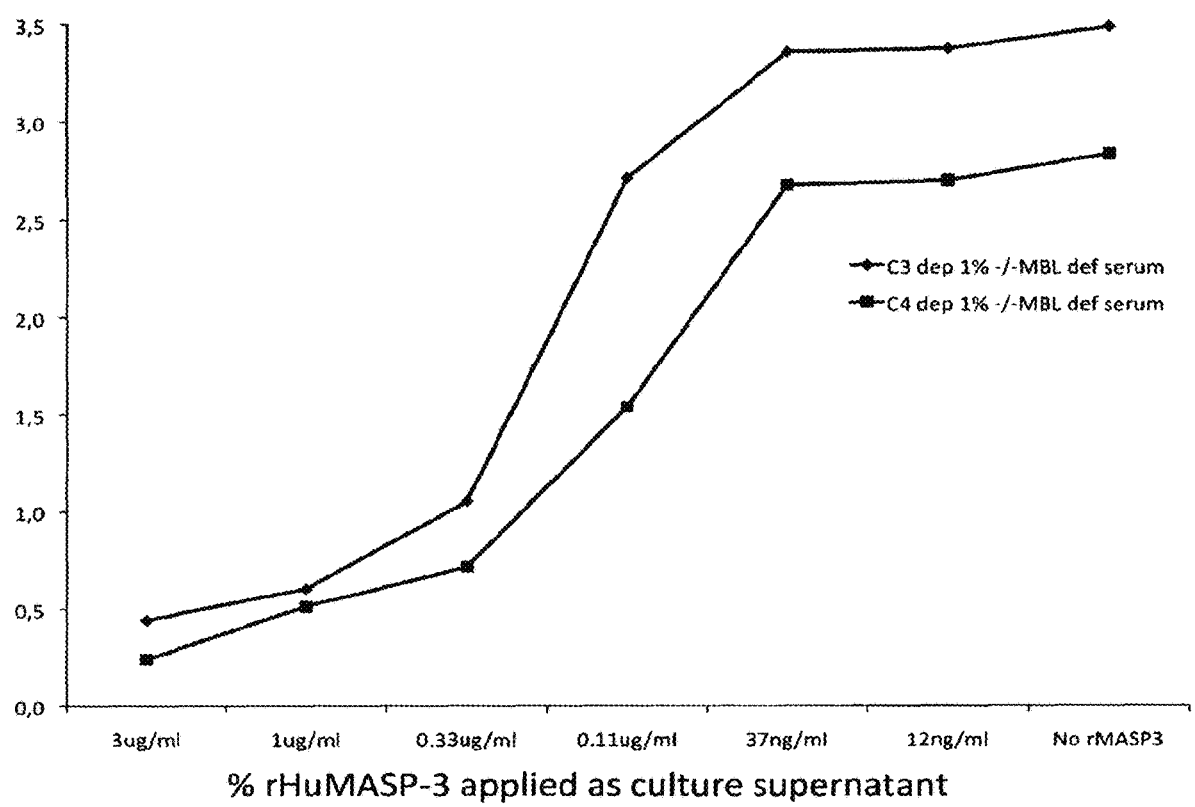

FIG. 8: MASP-3 inhibition of the complement. Human MBL were incubated with increased amount of MASP-3. MASP-3 were able to inhibit the activation of both the C3 and C4 complement proteins.

Figure 9:
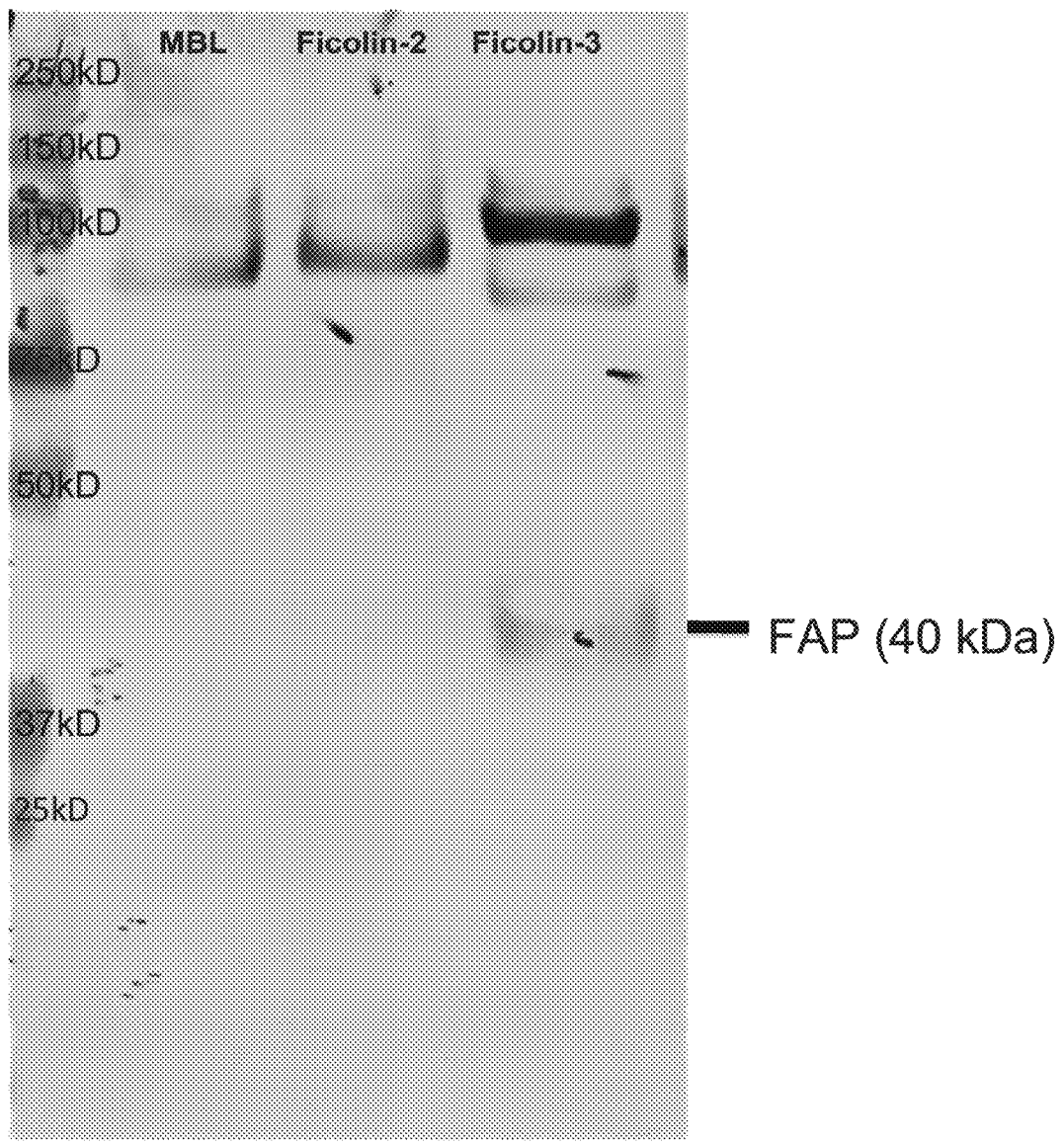

FIG. 9: Immunoprecipitation. Immunoprecipitation of serum Ficolin/MBL with mAb anti-MBL 131-11, anti-Ficolin-2 clone 219, and anti-Ficolin-3 clone 334. Followed by Dynal magnetic bead separation, SDS-PAGE, Western blot and biotin labeled anti-MASP-1/MASP-3 clone 8B3 as signal antibody.

Figure 10:
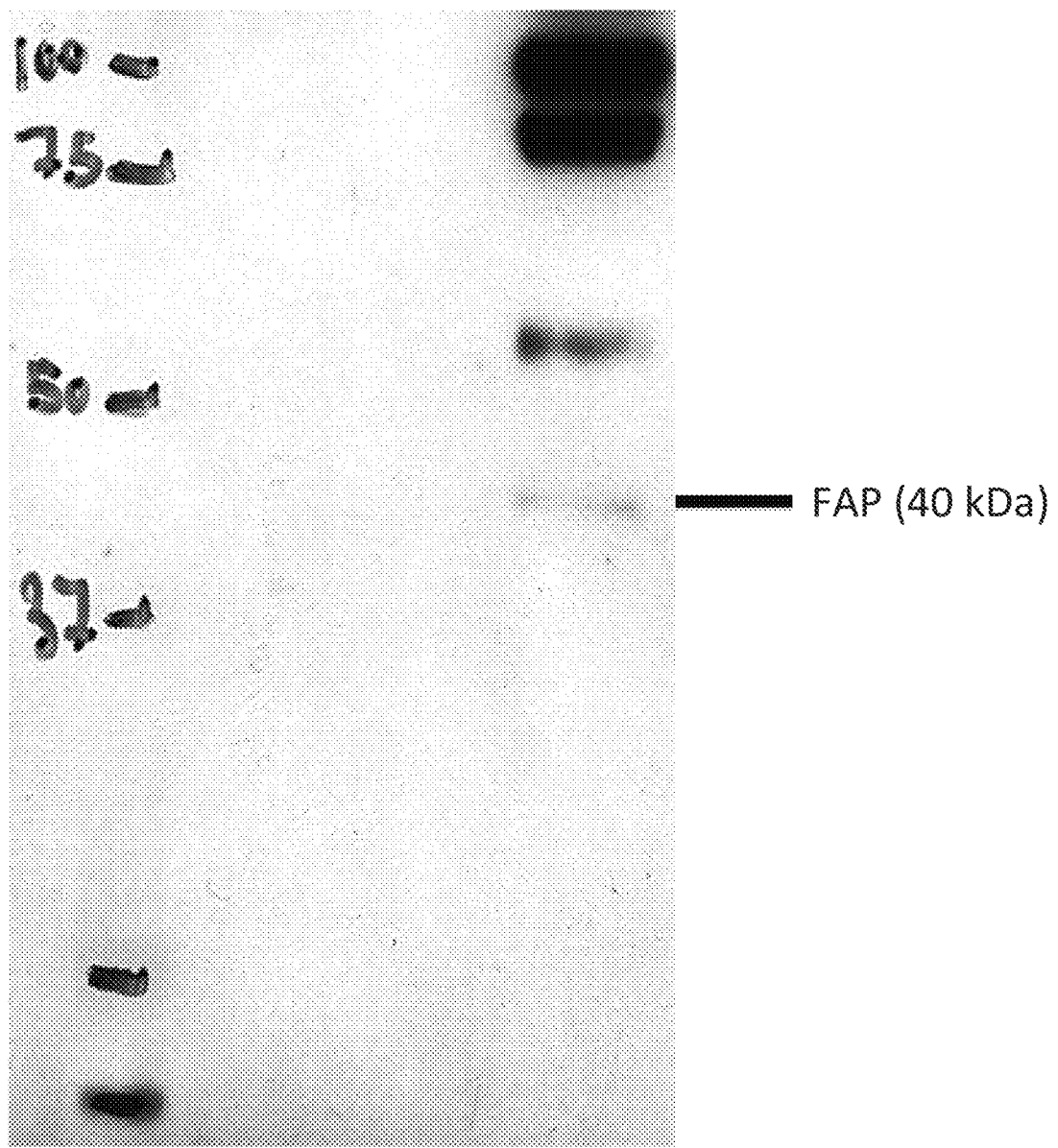

FIG. 10: FAP interact with Ficolin when bound to acetylated human serum albumin (AcHSA). Eluted serum Ficolin binding to AcHSA. Western blot with biotin labelled anti-MASP-1/MASP-3 clone 8B3 as signal antibody.

FIG. 11: Kinetics and dissociation constants for interaction between MASP-1 and MASP-3 and rFicolin-2 (Hummelshøj T et al., Mol. Immunol., 2007).

Figure 12:
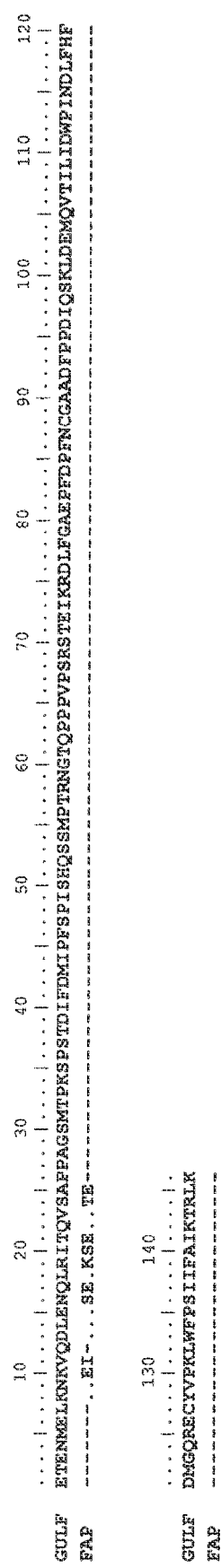

FIG. 12: Alignment of GULF and the 17 unique amino acids of FAP.

Figure 13:
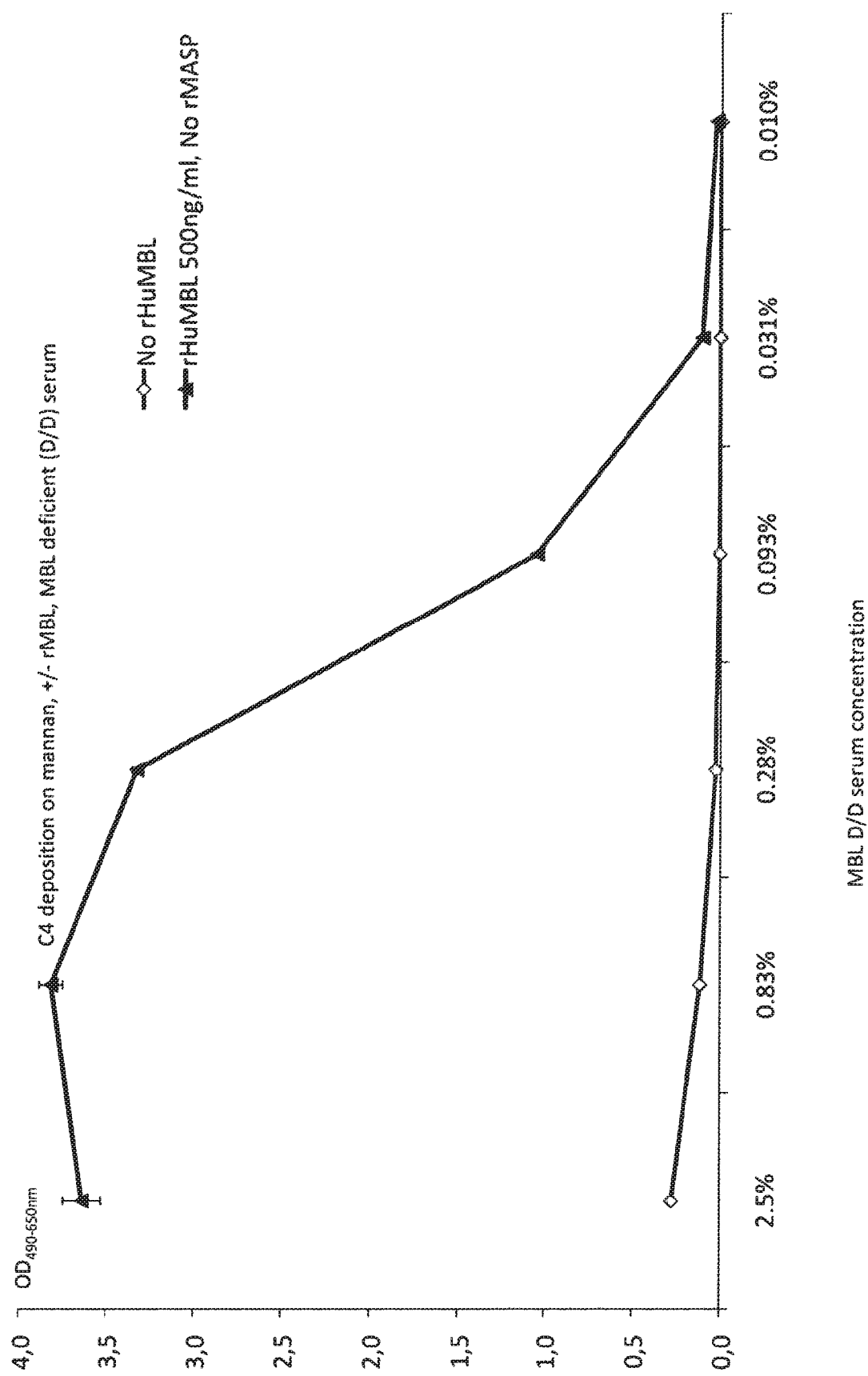

FIG. 13: Complement activation of C4 in a mannan/MBL ELISA assay. Mannan coated wells were incubated with or without recombinant human MBL followed by incubation with MBL homozygous deficient serum in serial dilutions. The C4 deposition was measured using polyclonal anti C4c antibodies. Error bars indicate two times the standard deviations on double determinations of each point on the curves.

Figure 14:
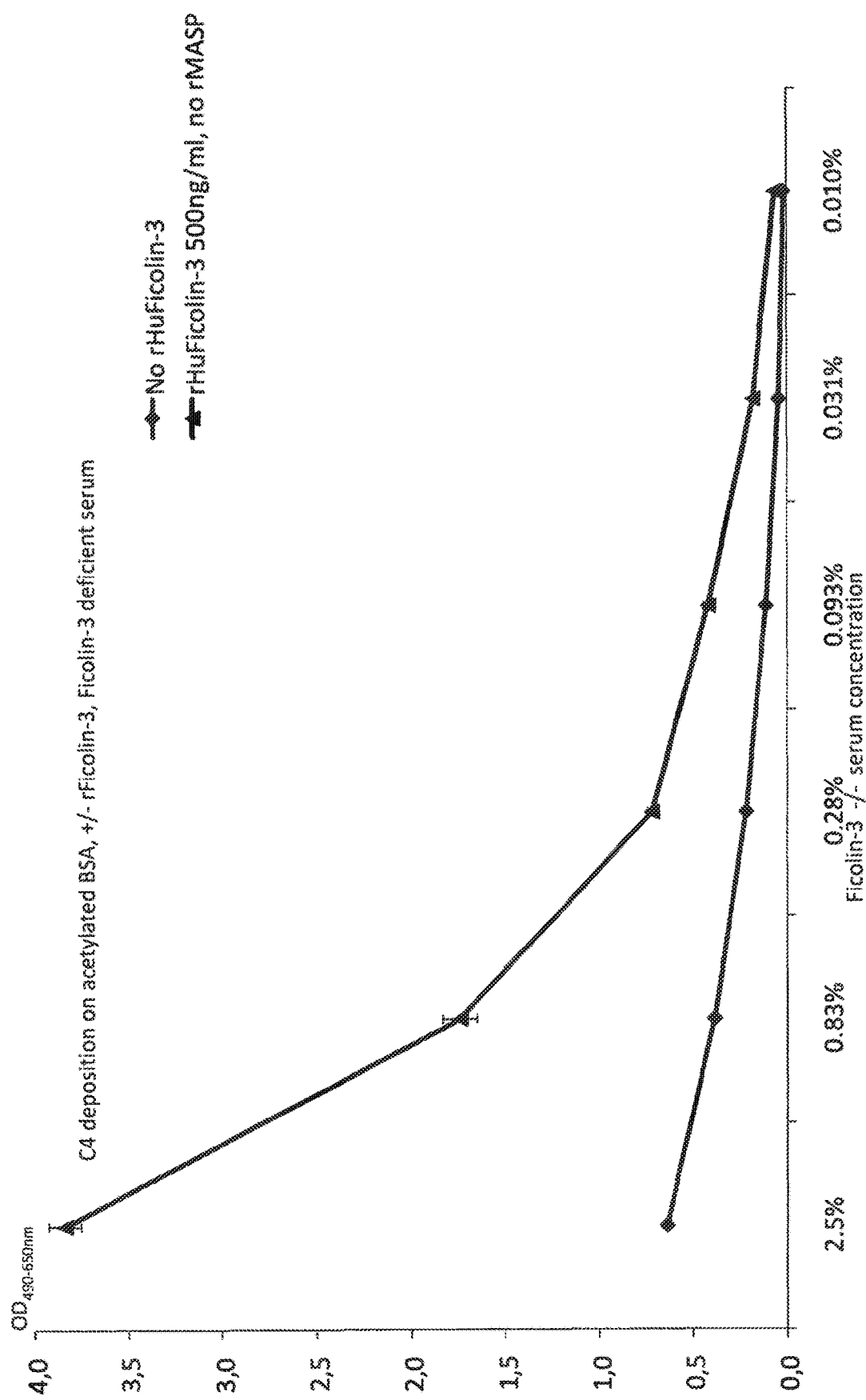

FIG. 14: Complement activation of C4 in an acetylated BSA/Ficolin-3 ELISA assay. AcBSA coated wells were incubated with or without recombinant human Ficolin-3 followed by incubation with Ficolin-3 homozygous deficient serum in serial dilutions. The C4 deposition was measured using polyclonal anti C4c antibodies. Error bars indicate two times the standard deviations on double determinations of each point on the curves.

Figure 15:
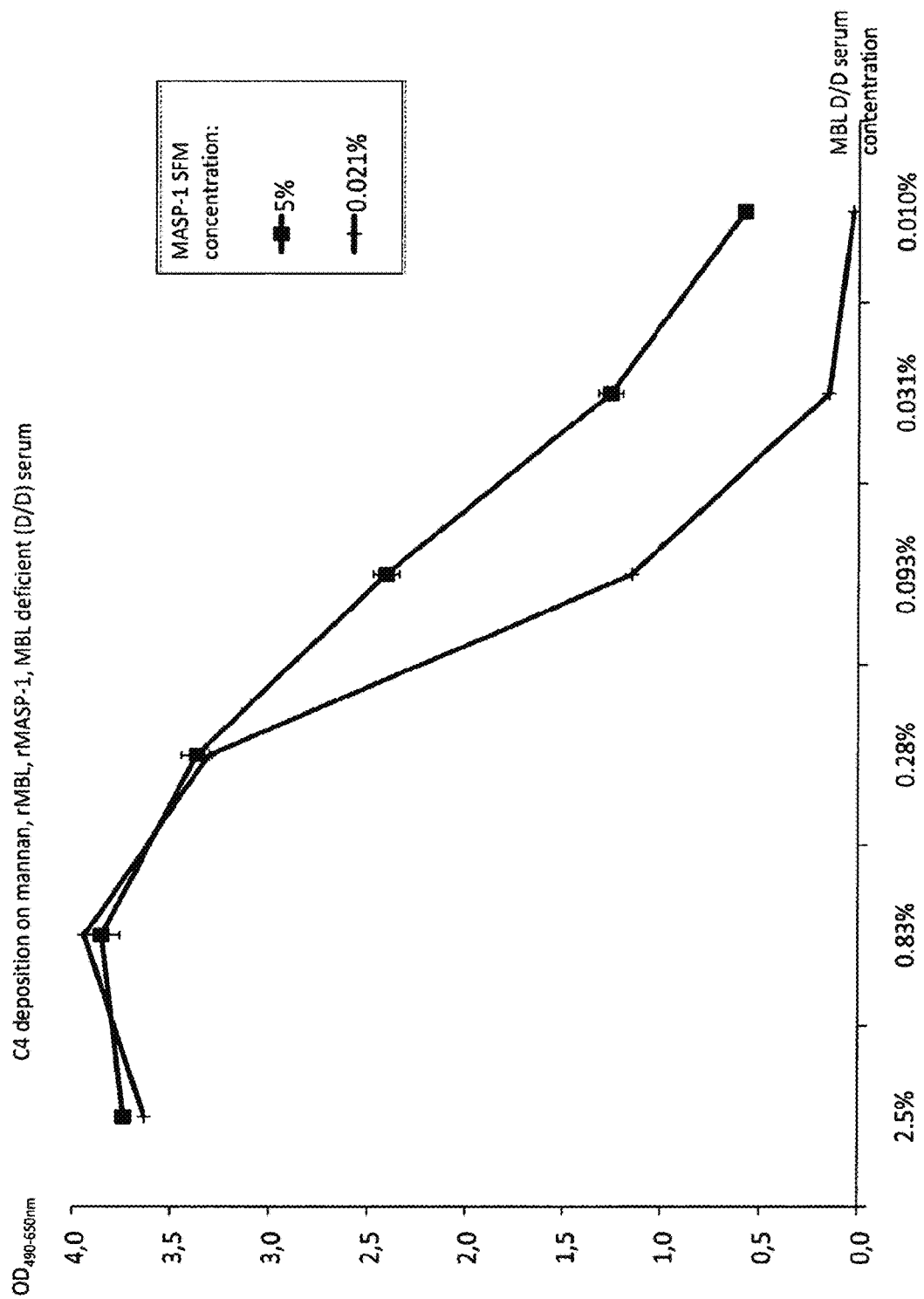

FIG. 15: Complement activation of C4 in a mannan/MBL ELISA assay. Mannan coated wells were incubated with recombinant human MBL followed by incubation with serial dilutions of rMASP-1 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 16:
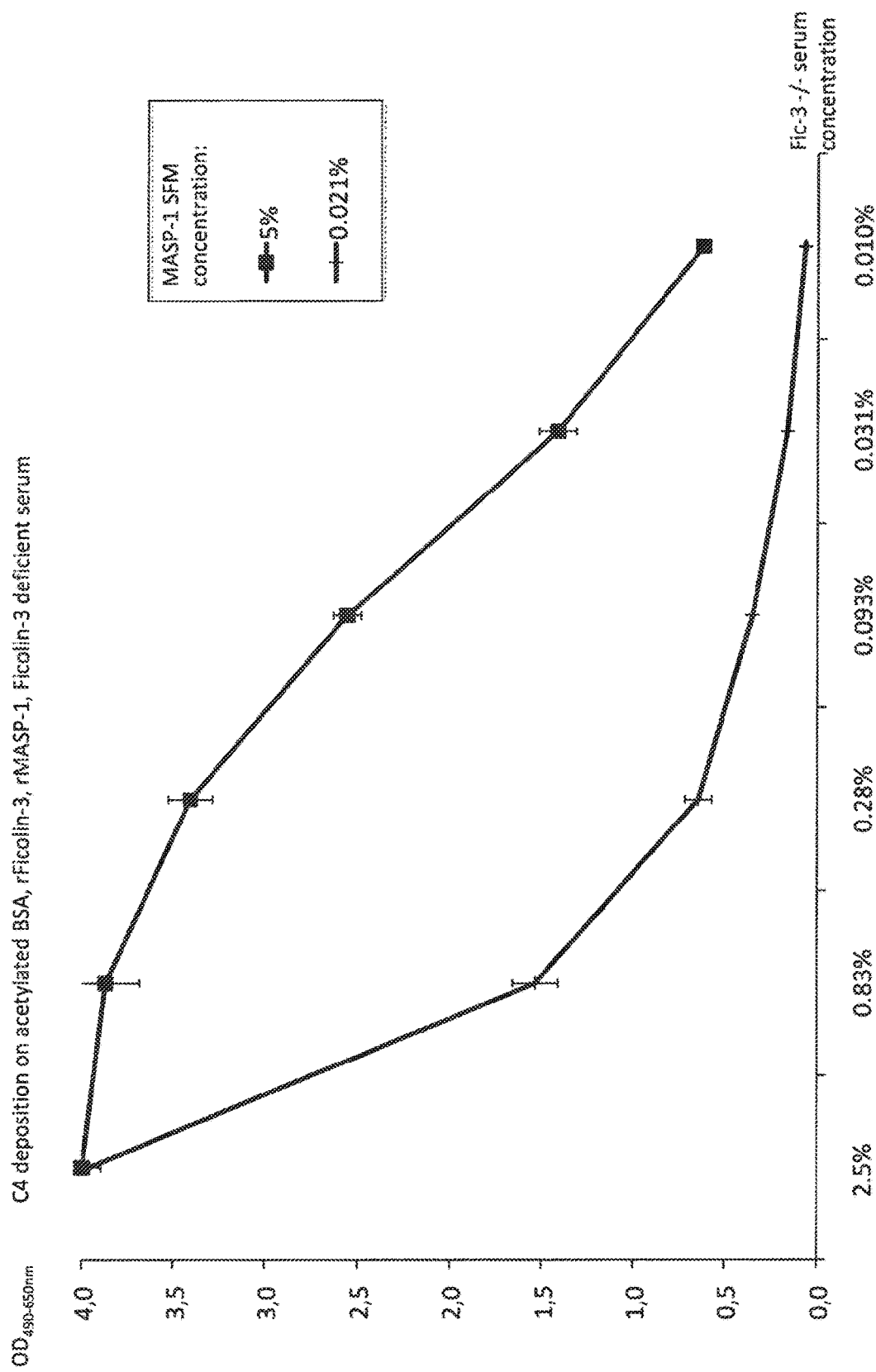

FIG. 16: Complement activation of C4 in an AcBSA/Ficolin-3 ELISA assay. AcBSA coated wells were incubated with recombinant human Ficolin-3 followed by incubation with serial dilutions of rMASP-1 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 17:
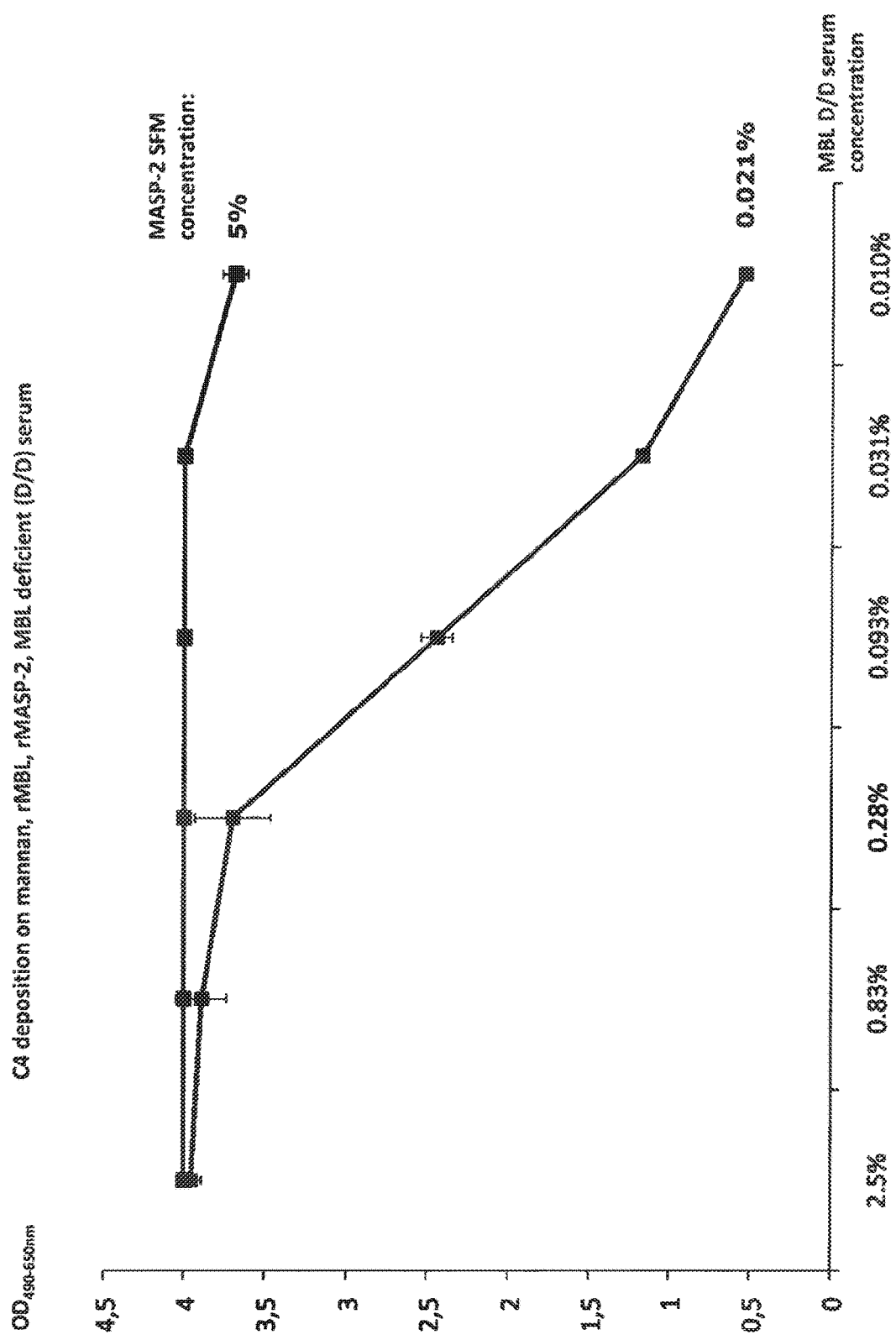

FIG. 17: Complement activation of C4 in a mannan/MBL ELISA. Mannan coated wells were incubated with recombinant human MBL followed by incubation with serial dilutions of rMASP-2 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 18:
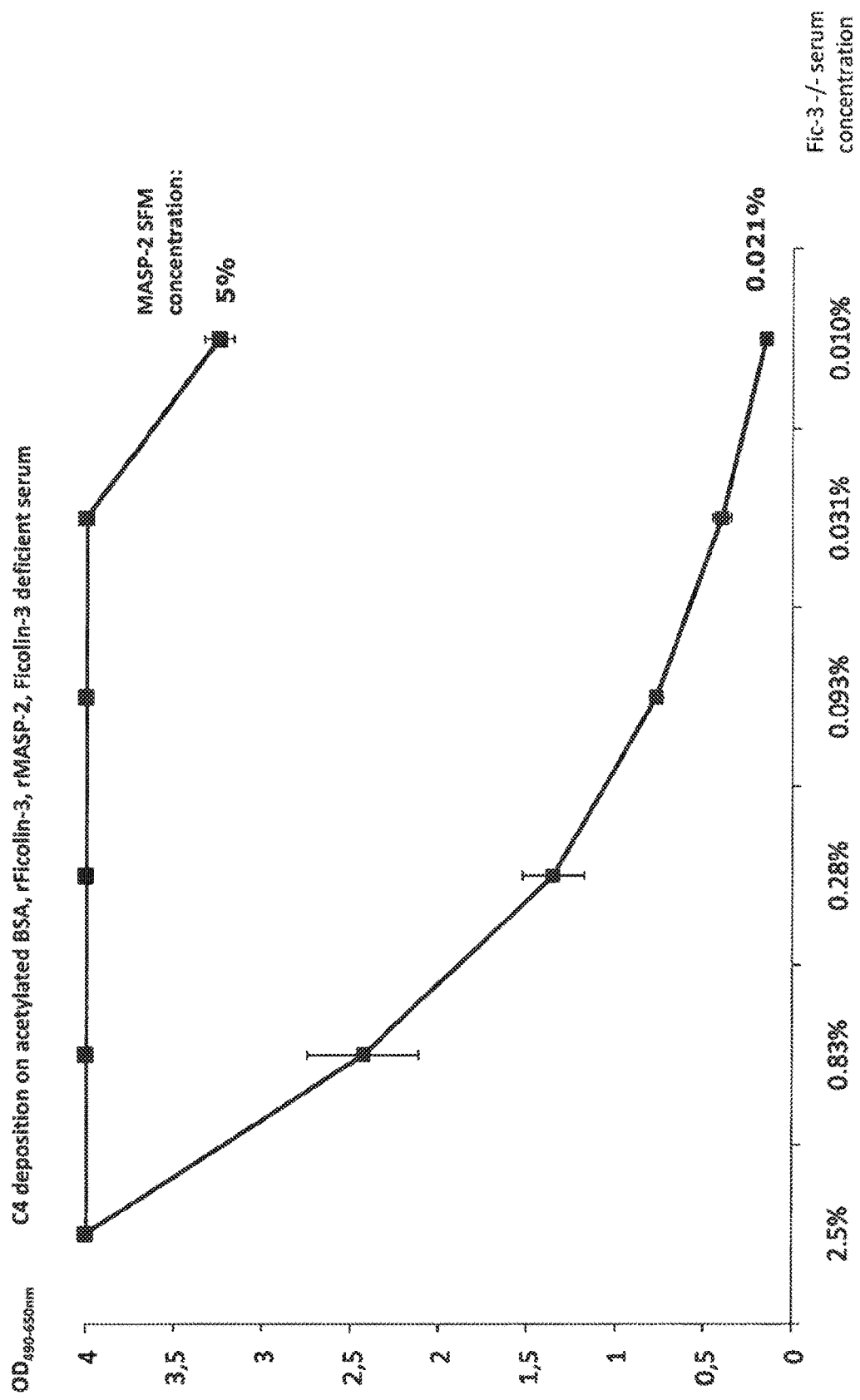

FIG. 18: Complement activation of C4 in an AcBSA/Ficolin-3 ELISA assay. AcBSA coated wells were incubated with recombinant human Ficolin-3 followed by incubation with serial dilutions of rMASP-2 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 19:
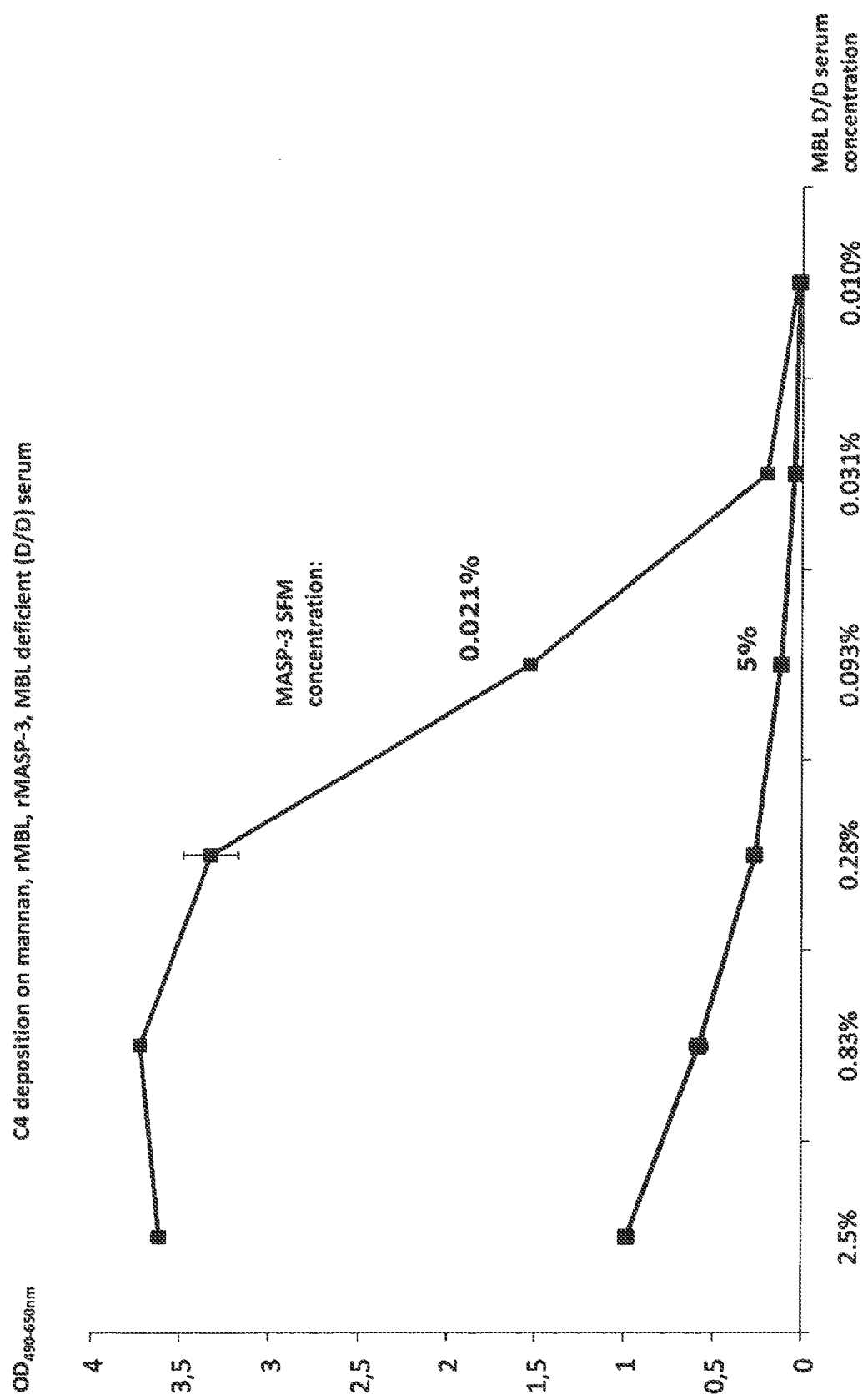

FIG. 19: Complement activation of C4 in a mannan/MBL ELISA assay. Mannan coated wells were incubated with recombinant human MBL followed by incubation with serial dilutions of rMASP-3 as serum free medium culture supernatants in one dimension. MBL homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 20:
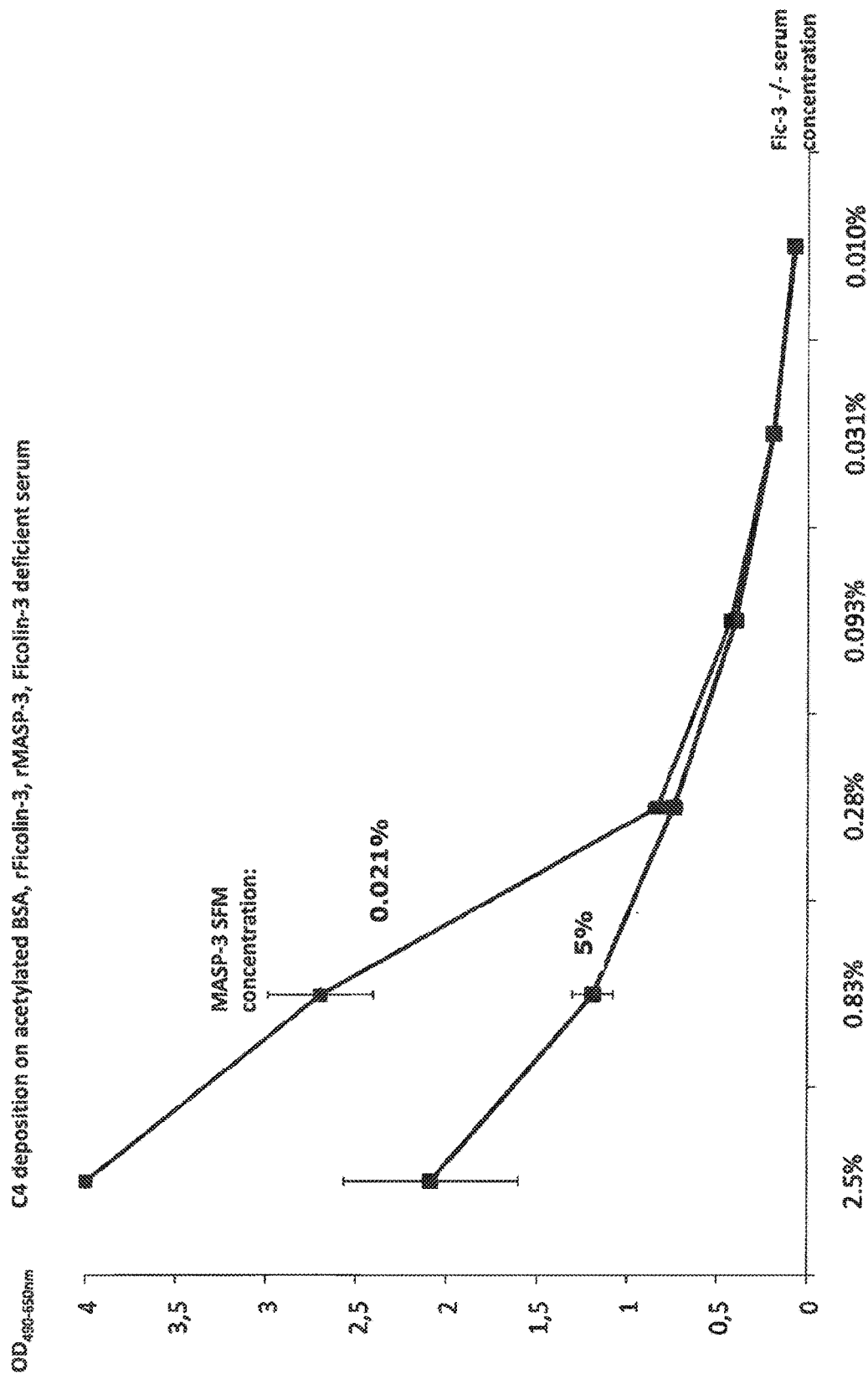

FIG. 20: Complement activation of C4 in an AcBSA/Ficolin-3 ELISA assay. AcBSA coated wells were incubated with recombinant human Ficolin-3 followed by incubation with serial dilutions of rMASP-3 as serum free medium culture supernatants in one dimension. Ficolin-3 homozygous deficient serum was subsequently incubated in serial dilutions in the second dimension. The C4 deposition was measured using polyclonal anti C4c antibodies. Error bars indicate two times the standard deviations on double determinations of each point on the curves.

Figure 21:
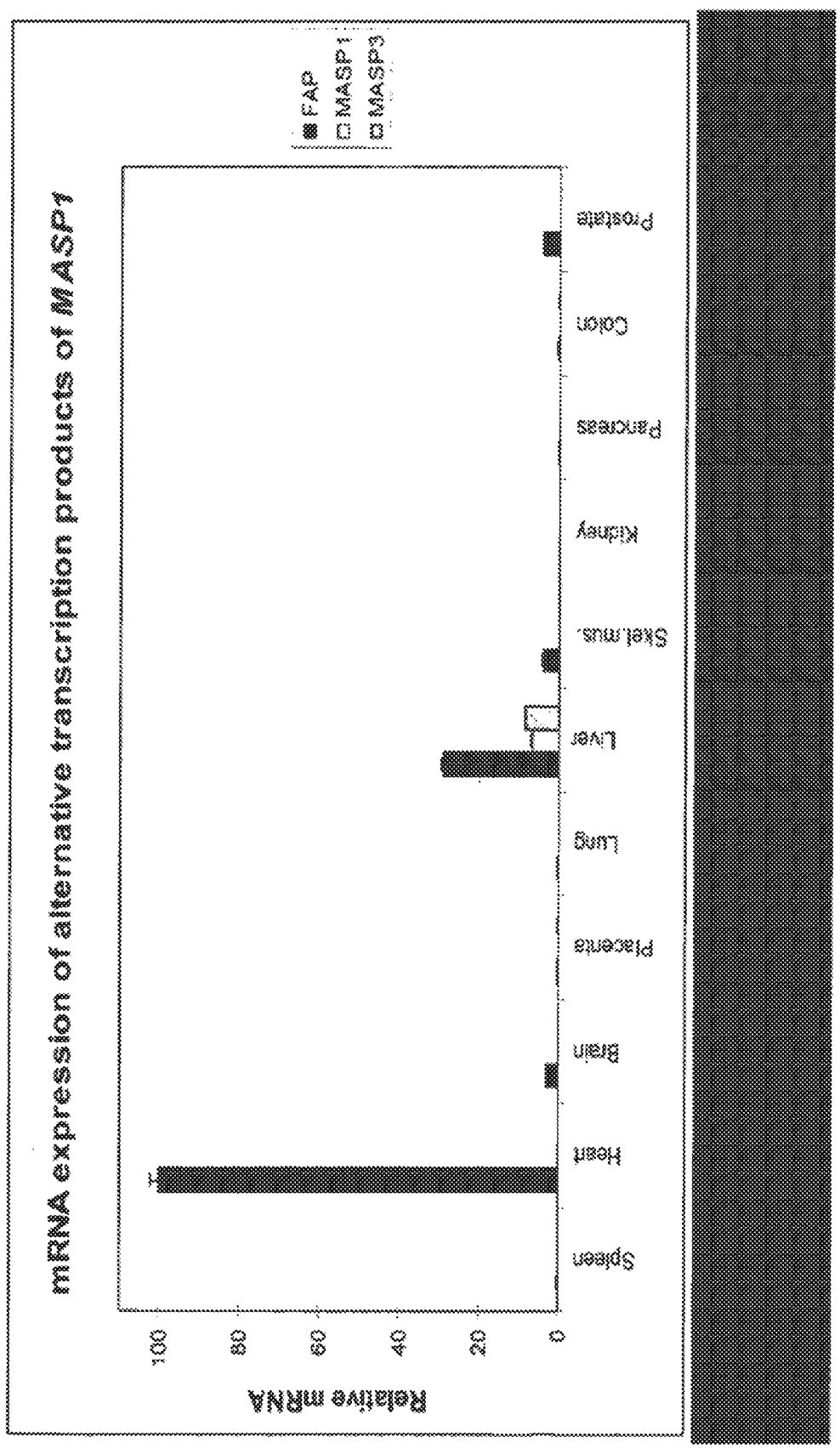

FIG. 21: Tissue distribution of FAP, MASP1 and MASP3. FAP was expressed much higher in the heart tissue compared to MASP1 and MASP3. FAP was expressed three times higher in the heart tissue compared to the FAP expression in liver. Furthermore, a higher FAP expression was observed in the liver compared to the MASP1 and MASP3 expression in the liver. Considerable FAP expression was also detected in brain, skeletal muscle and prostate tissues. The experiment was performed three times in duplicates. Standard error of the mean are indicated.

Figure 22:
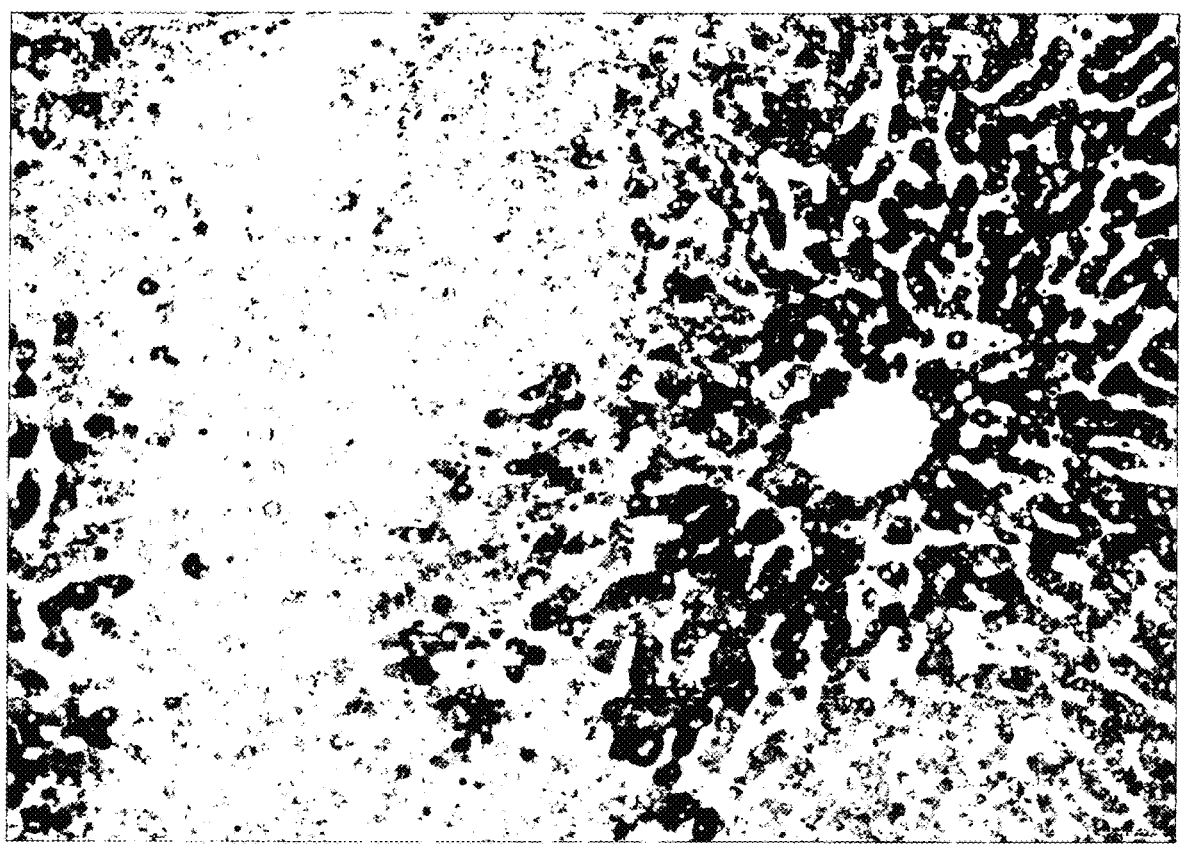

FIG. 22: Immunohistochemical liver localization of MAP-1 using polyclonal mouse antiserum raised against the 17 FAP specific C-terminal residues of the Protein. Control staining was negative. Several different polyclonal antibodies raised against FAP (rabbit and mouse) showed the same pattern staining.

Figure 23:

FIG. 23: Immunohistochemical analysis of MAP-1 tissue localization (OM X10). Left panel shows staining with a mAb (12B11) to MAP-1. Right panel shows the isotype control staining with a non-related IgG1k mAb. (A-B): Myocardium, (C-D): Skeletal muscle, (E-F): Liver sample, (G-H): Aortic tissue. Bottom right corner bar indicates 50 µm on all slides.

FIG. 24: Immunoprecipitation of MAP-1 and MASP-1/3 serum complexes. (A) MAP-1 and MASP-1/3 was immunoprecipitated from serum using mAb 20C4 (anti MAP-1) and mAb 8B3 (anti MASP-1/3, with an epitope on the common heavy chain). Reduced samples were electro-blotted and developed with pAb to MAP-1 or biotinylated mAbs to Ficolin-3 (FCN334) and MBL (Hyb 131-1). (B) Immunoprecipitation with mAbs to MBL (Hyb 131-11), Ficolin-2 (FCN219) and Ficolin-3 (FCN334) from 1 ml, 300 µl and 100 µl serum, respectively (Left side). Controls were MAP-1 precipitated from serum (sMAP-1) and rMAP-1 from culture supernatant (rMAP-1) using anti MAP-1 mAb 20C4 (right side). The samples were analyzed by western blotting probed with pAb to MAP-1.

Figure 25:
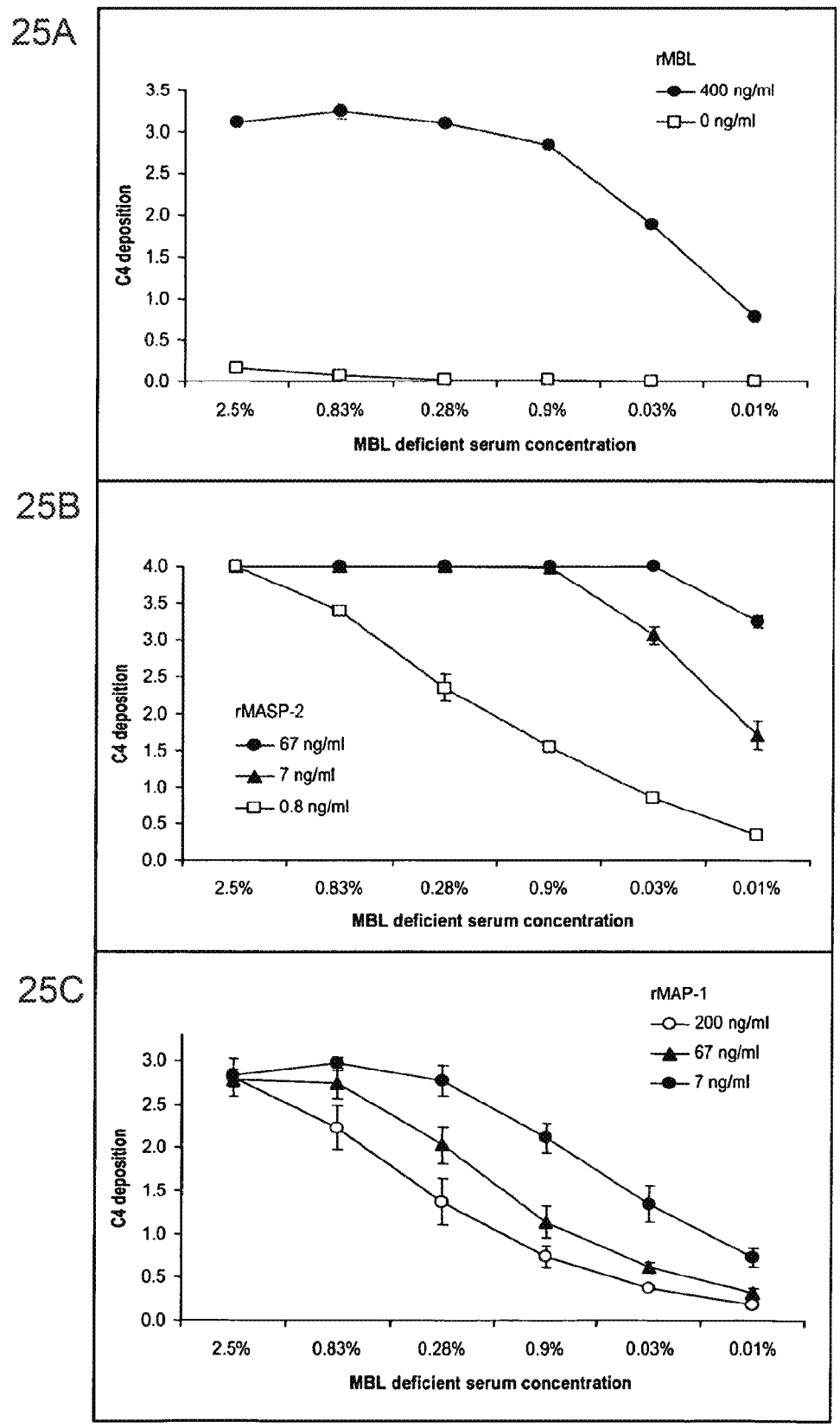
Figure 25:
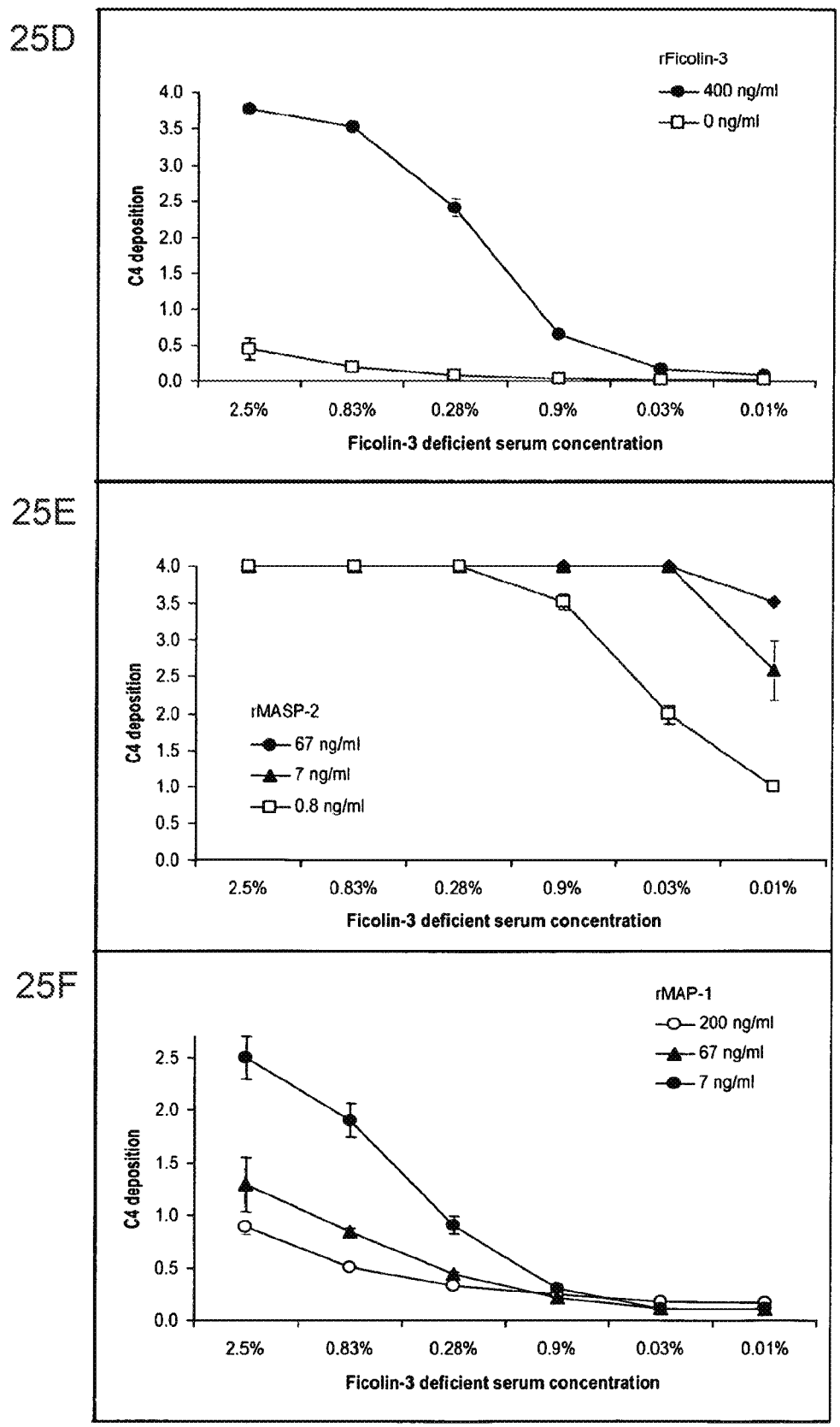

FIG. 25: Influence of MASP-2 and MAP-1 on MBL and Ficolin-3 mediated complement C4 deposition. The C4 depositions were measured using a polyclonal antibody to C4 and are given as $OD_{490-650\,nm}$ values. Error bars indicate two times the standard deviation of double determinations. Approximated concentrations of rMBL, rFicolin-3. rMAP-1 and rMASP-2 are given in the figure labels. (A) Reconstitution of the C4 deposition on a mannan coated surface using MBL deficient serum with rMBL at 400 ng/ml. Control was without addition of rMBL. (B) Dose dependent effect of rMASP-2 on the rMBL mediated C4 deposition. (C) Dose dependent effect of rMAP-1 on the rMBL mediated C4 deposition. (D) Reconstitution of the C4 deposition on an AcBSA coated surface using Ficolin-3 deficient serum with rFicolin-3 at 400 ng/ml. Control was without addition of rFicolin-3. (E) Dose dependent effect of rMASP-2 on the rFicolin-3 mediated C4 deposition. (F) Dose dependent effect of rMAP-1 on the rFicolin-3 mediated C4 deposition.

Figure 26:
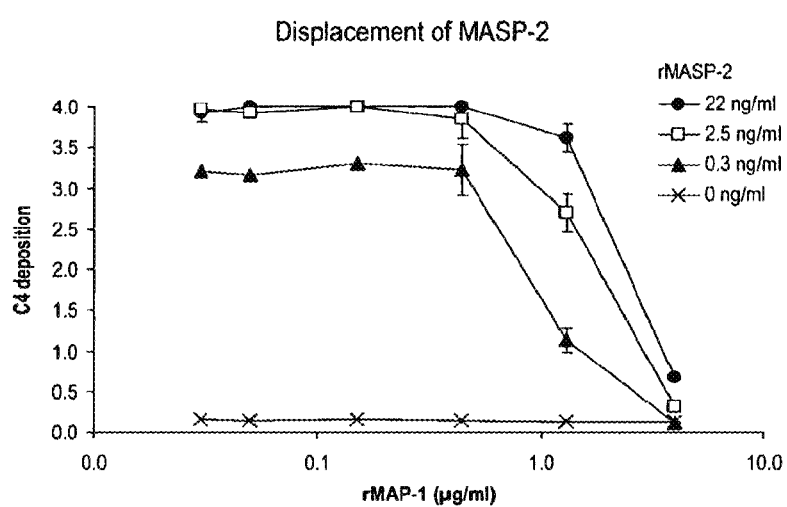

FIG. 26: Influence of MASP-2 and MAP-1 on the complement C4 deposition in a pure system. rMBL on a mannan surface was preincubated with serial dilutions of rMASP-2 in the first dimension. Serial dilutions of rMAP-1 were then applied in the second dimension followed by application of purified C4 at 1 µg/ml. The C4 depositions were measured with a pAb to C4 and are given as $OD_{490-650\,nm}$ values. Error bars indicate two times the standard deviation of double determinations. Approximated concentrations of rMAP-1 and rMASP-2 are given in the figure labels.

Figure 27:
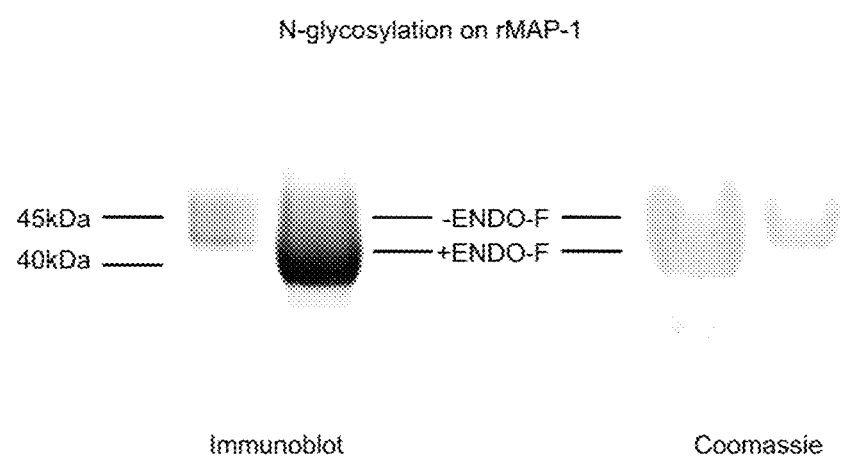

FIG. 27: SDS-PAGE analysis of rMAP-1. Left hand side shows the immunoblot analysis +/−N-glycosidase F treatment (ENDO-F). Right side shows the corresponding coomassie staining.

Figure 28:
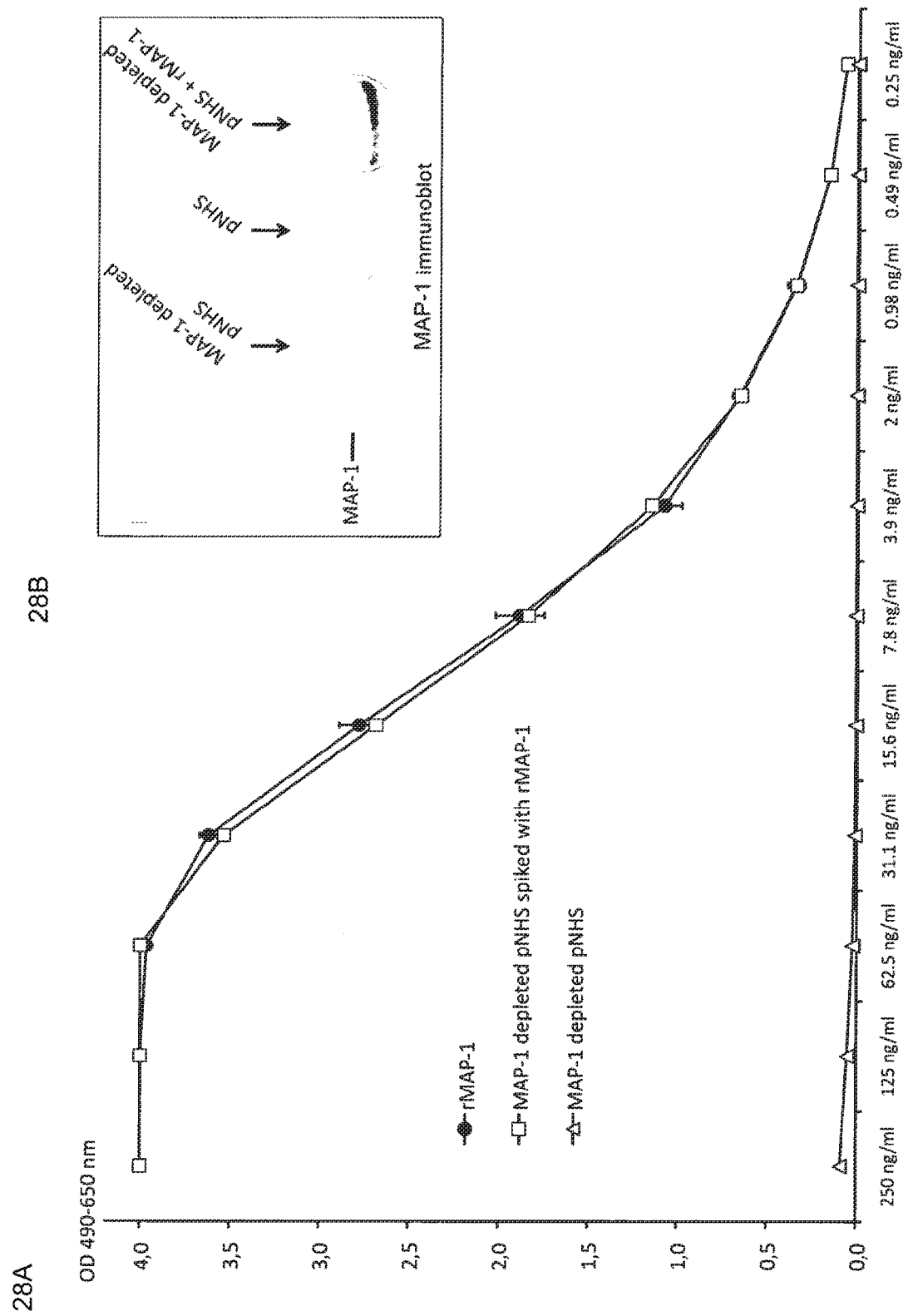

FIGS. 28A and 28B. Calibration curves. FIG. 28A) Calibration curve generated by mAb 20C4/mAb-8B3 two-side ELISA with two-fold serial dilutions of rMAP-1 applied to a MAP-I depleted pool of normal human serum (pNHS) or serial dilutions of rMAP-1 diluted in PBS/0.05% tween/10 mM EDTA. Error bars indicate two times the standard deviation of eight determinations. FIG. 28B) Immunoblot of serum depleted of MAP-I, normal human serum and MAP-I depleted serum spiked with rMAP-1.

Figure 29:
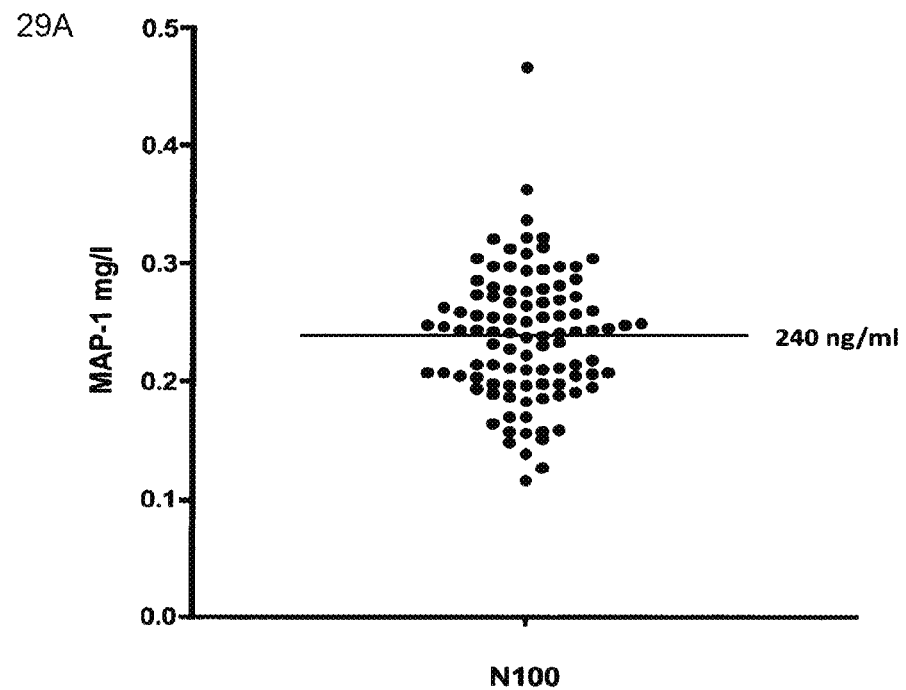
Figure 29:
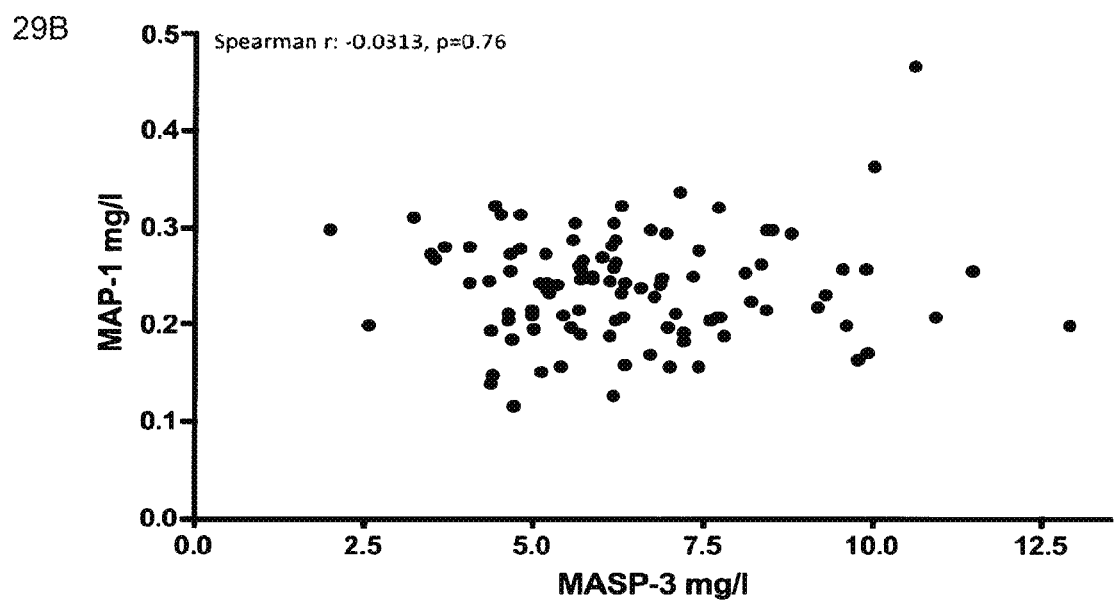
Figure 29C:
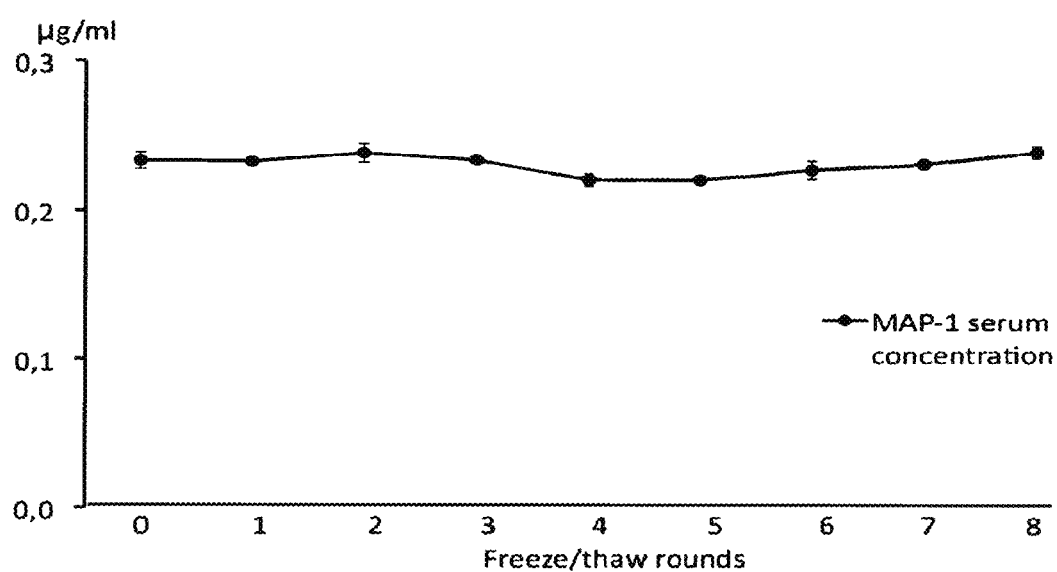

FIGS. 29A, 29B, and 29C. MAP-I serum concentration. FIG. 29A) Serum concentrations and distribution range of MAP-I in 100 Danish blood donors. Mean serum level: 240 ng/ml. Range: 115-466 ng/ml.; FIG. 29B) Correlation between the MASP-3 and MAP-I serum levels; FIG. 29C) Influence of freezing and thawing of serum. Serum was frozen and thawed for 8 rounds and the MAP-I level was measured for each round. Error bars indicate two times the standard deviation of double determinations.

Figure 30:
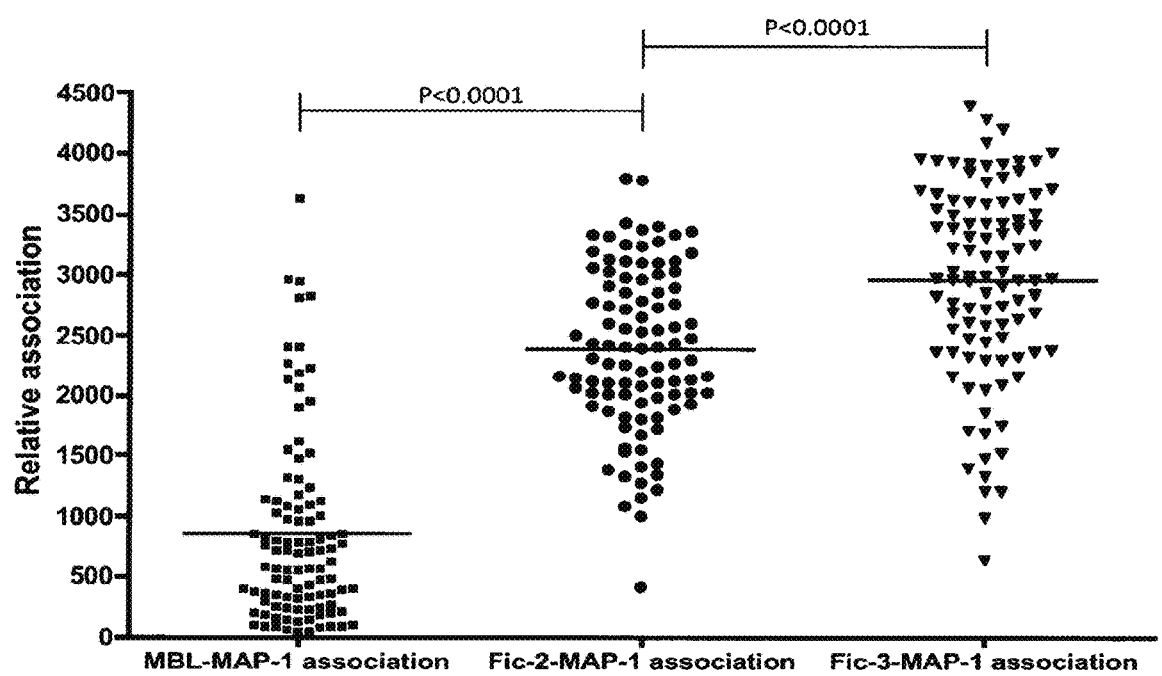
Figure 30:
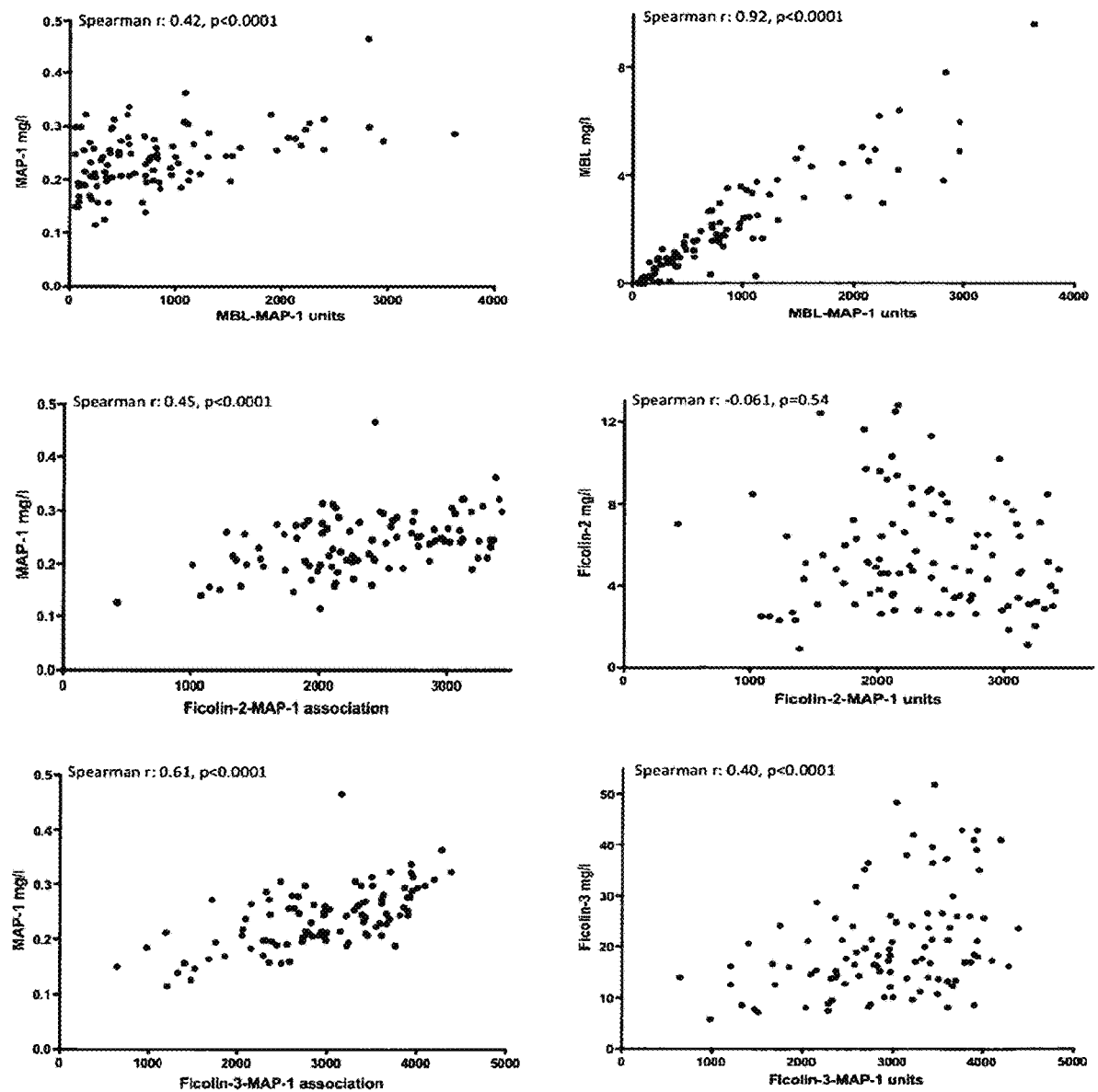

FIG. 30A) Association levels (in relative O. D. 490-650 nm units) between MAP-I and MBL, Ficolin-2 and Ficolin-3, respectively in 100 Danish blood donors. P values were obtained by non-parametric two-tailed t-test. FIG. 30B) Correlation between the MAP-I serum levels and the relative association to MBL, Ficolin-2 and Ficolin-3 (left hand side). Correlation between the MBL, Ficolin-2 and Ficolin-3 serum levels and the relative association to MAP-I (right hand side). Correlation p- and r-values were calculated using the non-parametric spearman rank correlation test.

Figure 31:
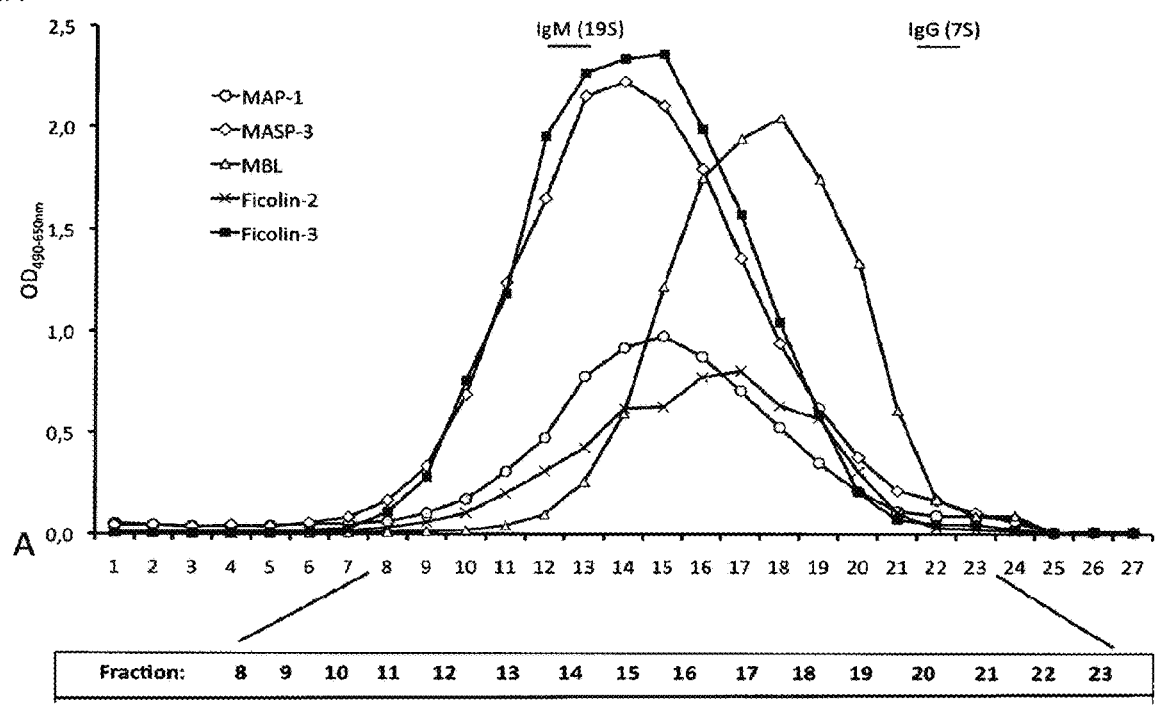
Figure 31:
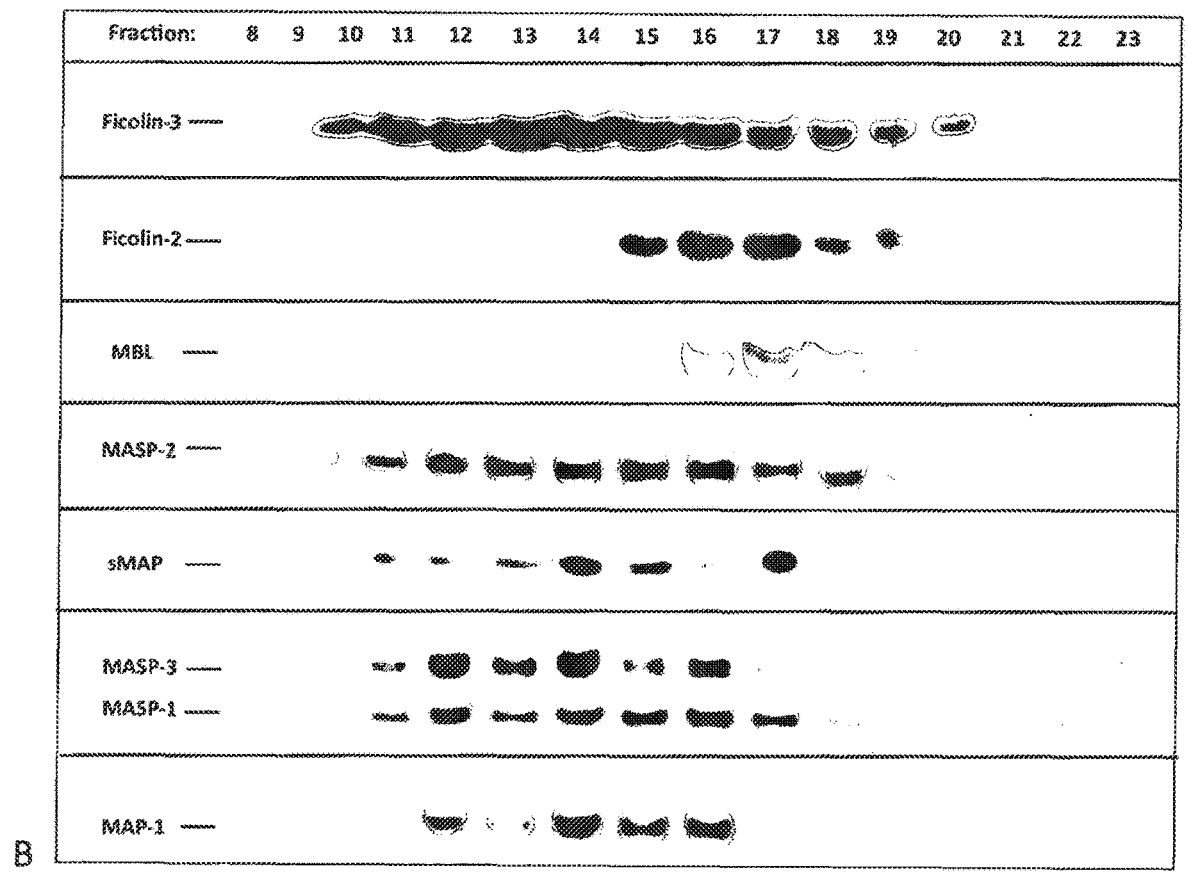
Figure 31:
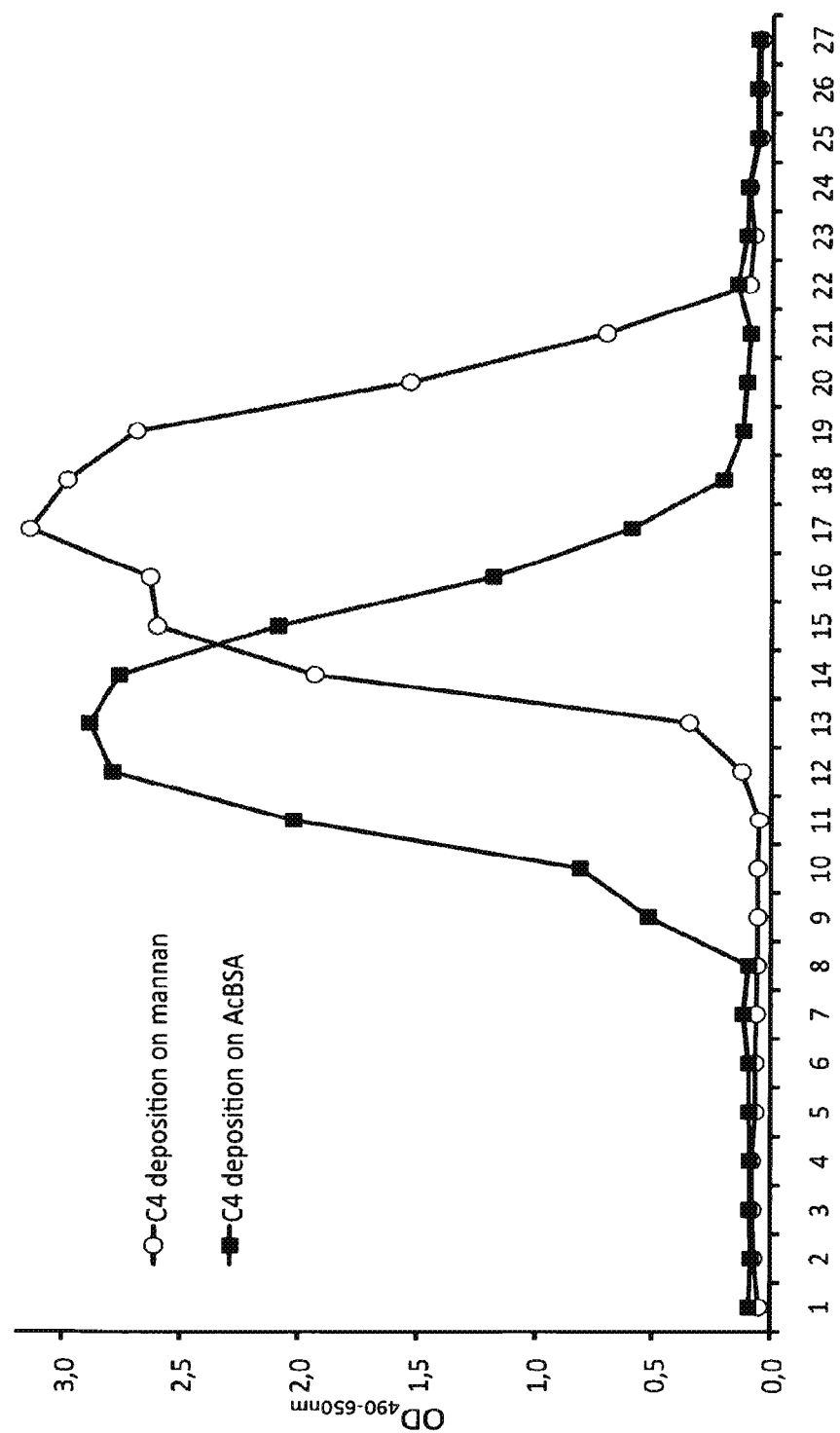

FIGS. 31A, 31B, and 31C. Sucrose gradient ultracentrifugation. FIG. 31A) Collected fractions (1-27) from serum subjected to a 10-30% sucrose density gradient. The fractions were analyzed by specific ELISA for: MAP-I, MASP-3, MBL, Ficolin-2 and -3. The peaks of serum IgM (19S) and IgG (7S) indicated at the top of the graph. FIG. 31B) Fractions number 8-23 analyzed by immunoblotting for: MAP-I, MASP-I, MASP-3, sMAP, MASP-2, MBL, Ficolin-2 and Ficolin-3. FIG. 31C) The fractions 1-27 analyzed by the capacity to activate exogenously applied human C4 on immobilized acetylated BSA (a Ficolin-3 ligand) or mannan (an MBL ligand).

DETAILED DISCLOSURE OF THE INVENTION

The present inventors have discovered a novel plasma protein of 40 kDa associated with the recognition molecules of the lectin complement pathway and identified this as a new alternative transcript variant of MASP-1/MASP-3 that in turn corresponds to the newly discovered plasma protein.

The novel protein (by the inventors named FAP (Ficolin Associated Protein) or MAP-I (MBL/Ficolin associated protein-1)) has been shown by the present inventors to lack an enzyme domain but to contain the ficolin/MBL binding domain and is thus expected to be involved in regulation and inhibition of complement and coagulation functions through competitions and displacement of the MASPs or alternatively, but not mutually exclusive as a protein involved in scavenger or signaling functions.

Uncontrolled activation of the complement system and/or the coagulation cascade is strongly associated with fatal severe outcome in variety of diseases ranging from systemic inflammation and sepsis, through myocardial infarction and autoimmunity.

Inhibition of coagulation and complement activation has been shown to be a promising therapeutic tool.

This present invention describes both a possible novel inhibitor of complement and coagulation functions. However, the polypeptides according to the present invention may have other functions, such as a scavenger and/or a signalling function. Moreover, it may be used as a new biomarker in several disease settings, including malignant diseases, autoimmune, metabolic and/or inflammatory conditions.

The inventors of the present invention have found a plasma protein present in vivo named Ficolin Associated Protein (FAP) and showed that it is primarily associated with the ficolins (FIG. 9), but it may likely also be associated with mannose-binding lectin. By searching nucleotide database of NCBI the inventors of the present invention found a possible transcript variant that corresponds to a truncated of MASP-1. Based on this sequence, primers were designed in order to amplify the putative new gene transcript. Subsequently, using human liver cDNA a new alternative transcript variant of the MASP-1 gene (FIG. 1) was identified. This mRNA strain was sequenced and accordingly the amino acid sequence was determined, which corresponds to the molecular weight of the observed protein in plasma/serum of 40 kDa (FIG. 5). The new protein is partly identical to MASP-1 and MASP-3, but lacks a serine protease domain, but contain a novel exon encoding 17 amino acids followed by a stop codon. This exon is spliced out in the MASP1 and MASP3 transcript (FIG. 2). By using a panel of mRNA expression libraries the present inventors have found evidence that this protein is strongly expressed in the heart and in the liver, followed by skeletal muscle (FIG. 3). Weak expression was observed in the brain, the digestive tract, prostata and in the spleen (FIG. 3). Taqman analysis confirmed the expression in heart and liver cells. FAP was expressed much higher in the heart tissue compared to MASP1 and MASP3. FAP was expressed three times higher in the heart tissue compared to the FAP expression in liver. Furthermore, a higher FAP expression was observed in the liver compared to the MASP1 and MASP3 expression in the liver. Considerable FAP expression was also detected in brain, skeletal muscle and prostate tissues. The experiment was performed three times in duplicates.

The high expression in the heart is very prominent and has made the present inventors suggest a use of the polypeptides according to the present invention as a very useful protector against tissue damage in autoimmune, metabolic and/or inflammatory conditions, such as medical conditions associated with the heart.

The present inventors have established assays to assess complement activity initiated by ficolins and mannose-binding lectin and the present inventors have thus been able to show a possible functional complement inhibition of FAP.

The present inventors have establishing real time quantitative assays to measure the exact relative expression level in different tissues.

The polypeptides according to the present invention may be produced by recombinant techniques. Rabbits or mice may be immunized with a unique 17 amino acid long peptide in order to obtain FAP polyclonal and monoclonal specific antibodies, respectively.

Specific FAP antibodies may be used for quantitative measurement of FAP and immunohistochemical detection in different tissues.

Binding constants between FAP and different binding partners as described herein may be determined in ELISA and by using surface plasmon resonance technology (Biacore).

A FAP specific acceptor protein, such as a specific cell surface bound receptor may be identified by standard assays known to the person skilled in the art, such as assays wherein the protein is bound directly to cells.

The novel protein Ficolin Associated Protein (FAP) is an alternative splicing variant of MASP1. The protein lacks the serine protease domain but it still contains the domains that are involved in the binding to the initiators of the lectin pathway of the complement system. Thus, the present inventors expect the protein to be involved in regulation and inhibition of the function of MASP-1 and MASP-3 (complement, coagulation functions and other enzymes substrates) through competitions and displacement of the MASPs. Alternatively, but not mutually exclusive FAP may function as scavenger molecule facilitating removal of FAP/MBL/ficolin complexes bound to endogenous waste material or pathogens.

Uncontrolled activation of the complement system and the coagulation cascade are associated with adverse outcome and functional inhibitors, such as the polypeptides according to the present invention may be very useful for the control of the complement system and the coagulation cascade. In addition the polypeptides according to the present invention may be used in other settings. Another angle could be to use the protein as biomarker in different disease settings.

The protein is unique and may provide the basis for new drugs and/or new diagnostic tools.

Polypeptides according to the present invention comprising the amino acid sequence of SEQ ID NO:4 or an immunologic fragment or variant thereof may have a specific function associated with this sequence of amino acids. It is suggested by the present inventors that such polypeptides may have a function or activity corresponding to the activity of one or more protein selected from DNMT1 DNA (cytosine-5-)-methyltransferase 1 (DNMT1), Golgin subfamily B member 1 (GOLGB1), A-kinase anchor protein 9 (AKAP9), B- and T-lymphocyte-associated protein)(CD272 antigen), PTB domain-containing engulfment adapter protein 1 (GULP), and MACRO domain-containing protein 2.

In some particular interesting embodiments the polypeptides according to the present invention have a function or activity corresponding to the activity of PTB domain-containing engulfment adapter protein 1 (GULP).

Definitions

The term "ficolin-associated polypeptide" as used herein means any protein or polypeptide comprising the amino acid sequence 20-380 of native human ficolin-associated protein (FAP) (SEQ ID NO: 1) or amino acid sequence of 16-363 of SEQ ID NO:9, functional variants, functional truncated versions thereof as well as functional derivatives or conjugates, which polypeptide do not have complement activity, but posses the ability to compete with MASP-1, MASP-2, or MASP-3 for binding to ficolin-3, MBL, C1q, lung surfactant proteins SP-A and/or SP-D and/or CL-L1 (and other collectin family members). This includes but is not limited to human ficolin-associated polypeptide (FAP) having SEQ ID NO:1 and variants thereof.

The term "ficolin-associated protein (FAP)" as used herein means proteins that have the amino acid sequence 1-380 (with or without signal peptide, such as the amino acid sequence 20-380) of native human FAP (SEQ ID NO: 1), natural allelic variations and homologous thereof. It also includes proteins with a slightly modified amino acid sequence, for instance, a modified N- or C-terminal end including N- or C-terminal amino acid deletions or additions so long as those proteins substantially retain the activity of FAP. The term "ficolin-associated protein (FAP)" is used interchangeable herein with the terms "MAP-1" or "MBL/Ficolin associated protein-1". "FAP" within the above definition also includes natural allelic variations that may exist and occur from one individual to another. The term also includes proteins with homologous sequence and similar function derived from other species than human, such as bovine, pig, dog, horse, rat, and mouse. Also, degree and location of glycosylation or other post-translation modifications may vary depending on the chosen host cells and the nature of the host cellular environment.

The term "MBL-Associated Serine Protease-1" or "MASP-1" as used herein means proteins that have the amino acid sequence 1-699 (with or without signal peptide, such as the amino acid sequence 20-699) of native human MASP-1 (SEQ ID NO:5), natural allelic variations and homologous thereof. It is to be understood that the sequence may be in one or more peptide chains, such as in two chains, i.e. the heavy and light chains of the native human protein.

The term "MBL-Associated Serine Protease-3" or "MASP-3" as used herein means proteins that have the amino acid sequence 1-728 (with or without signal peptide, such as the amino acid sequence 20-728) of native human MASP-3 (SEQ ID NO:7), natural allelic variations and homologous thereof. It is to be understood that the sequence may be in one or more peptide chains, such as in two chains, i.e. the heavy and light chains of the native human protein.

The term "MBL-Associated Serine Protease-2" or "MASP-2" as used herein means proteins that have the amino acid sequence 1-686 (with or without signal peptide, such as the amino acid sequence 16-686) of native human MASP-2 (SEQ ID NO:9), natural allelic variations and homologous thereof. It is to be understood that the sequence may be in one or more peptide chains, such as in two chains, i.e. the heavy and light chains of the native human protein.

The terms "small MBL-associated protein", "sMAP", "MBL-associated plasma protein of 19 kD" or, "MAp19" as used herein means proteins that have the amino acid sequence 1-185 (with or without signal peptide, such as the amino acid sequence 16-185) of native human sMAP (SEQ ID NO:11), natural allelic variations and homologous thereof.

The terms "variant" or "variants", as used herein, is intended to designate a ficolin-associated polypeptide having the sequence of SEQ ID NO:1 or a polypeptide comprising the amino acid sequence of SEQ ID NO:4, wherein one or more amino acids have been substituted by another amino acid and/or wherein one or more amino acids have been deleted and/or wherein one or more amino acids have been inserted in the polypeptide and/or wherein one or more amino acids have been added to the polypeptide. Such addition can take place either at the N-terminal end or at the C-terminal end or both. The "variant" or "variants" within this definition still have functional activity. In some embodiment a variant has 70% sequence identity with the sequence of SEQ ID NO:1. In some embodiments a variant has 80% sequence identity with the sequence of SEQ ID NO:1. In other embodiments a variant has 90% sequence identity with the sequence of SEQ ID NO:1. In a further embodiment a variant has 95% sequence identity with the sequence of SEQ ID NO:1.

In some embodiments a variant has 70% sequence identity with the sequence of SEQ ID NO:4. In some embodiments a variant has 80% sequence identity with the sequence of SEQ ID NO:4. In other embodiments a variant has 90% sequence identity with the sequence of SEQ ID NO:4. In a further embodiment a variant has 95% sequence identity with the sequence of SEQ ID NO:4.

The phrases "functional variant", "functional truncated versions", and "functional derivatives" as used herein refers to variants, truncated versions, as well as derivatives of SEQ ID NO:1, which polypeptides comprises essential sequence parts of SEQ ID NO:1 and at least posses the ability to compete with MASP-1 or MASP-3 for binding to the ficolins or MBL without having the complement activity and/or serine protease activity. It is to be understood that a ficolin-associated polypeptide may have to or three features selected from being a both a variant, and/or truncated and/or a derivative.

A functional variant of a ficolin-associated polypeptide encompass those that exhibit at least about 25%, such as at least about 50%, such as at least about 75%, such as at least about 90% of the specific activity of wild-type FAP that has been produced in the same cell type, when tested in the assays as described herein.

The term "immunologic fragment" as used herein refers to fragment of an amino acid sequence that posses essentially the same functional activities and the same spatial orientation to be recognized by an antibody. Accordingly a specific antibody will bind both the polypeptide and immunologic fragments thereof.

The term "another amino acid" as used herein means one amino acid that is different from that amino acid naturally present at that position. This includes but is not limited to amino acids that can be encoded by a polynucleotide. In some embodiments the different amino acid is in natural L-form and can be encoded by a polynucleotide.

The term "derivative" as used herein, is intended to designate a ficolin-associated polypeptide exhibiting substantially the same or improved biological activity relative to wild-type human FAP, in which one or more of the amino acids of the parent peptide have been chemically modified, e.g. by alkylation, PEGylation, acylation, ester formation or amide formation or the like.

The term "complement activity" as used herein means the ability activate the complement system. The complement activity may be measured with assay as described in the section headed "Assays".

The term "mannose-binding lectin (MBL)" as used herein also means mannan-binding lectin, mannose-binding protein (MBP1), and mannan-binding protein, which terms may be used interchangeably.

The term "capable of associating" as used herein refers to the ability of the proteins according to the present invention to specifically bind in solution one or more of the initiators of the lectin pathway of the complement system or other proteins that may be involved in the effect of the polypeptide.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

The term "vector", as used herein, means any nucleic acid entity capable of the amplification in a host cell. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

In a further aspect, the invention provides a recombinant host cell comprising the polynucleotide construct or the vector. In some embodiments the recombinant host cell is a eukaryotic cell. In other embodiments the recombinant host cell is of mammalian origin. In a further embodiment the recombinant host cell is selected from the group consisting of CHO cells, HEK cells and BHK cells.

The term "a host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Nati. Acad. Sci. USA* 77:4216-4220, 1980). Also useful are 3T3 cells, Namalwa cells, myelomas and fusions of myelomas with other cells.

In a further aspect, the invention provides a transgenic animal containing and expressing the polynucleotide construct.

In a further aspect, the invention provides a transgenic plant containing and expressing the polynucleotide construct.

In a further aspect, the invention relates to a method for producing the ficolin-associated polypeptide of the invention, the method comprising cultivating a cell comprising the polynucleotide construct in an appropriate growth medium under conditions allowing expression of the polynucleotide construct and recovering the resulting polypeptide from the culture medium.

As used herein the term "appropriate growth medium" means a medium containing nutrients and other components required for the growth of cells and the expression of the nucleic acid sequence encoding the ficolin-associated polypeptide of the invention.

In a further aspect, the invention relates to a method for producing the ficolin-associated polypeptide, the method comprising recovering the polypeptide from milk produced by the transgenic animal.

In a further aspect, the invention relates to a method for producing the ficolin-associated polypeptide, the method comprising cultivating a cell of a transgenic plant comprising the polynucleotide construct, and recovering the polypeptide from the resulting plant.

In the present context, the term "treatment" is meant to include both prevention of an expected condition involving inappropriate complement activation, such as inflammation and reperfusion injury and regulation of an already occurring condition, such as myocardial infarction and stroke with the purpose of inhibiting or minimising the tissue damage Prophylactic administration of the ficolin-associated polypeptide according to the invention is thus included in the term "treatment".

The term "subject" as used herein is intended to mean any animal, in particular mammals, such as humans, and may, where appropriate, be used interchangeably with the term "patient".

The term "sequence identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a sequence relationship that includes both identical matches and conservative substitution matches. If two polypeptide sequences have, for example, (fraction ($10/20$)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction ($15/20$))). Therefore, in cases where there are conservative substitutions, the degree of similarity between two polypeptides will be higher than the percent identity between those two polypeptides.

Conservative modifications to the amino acid sequence of SEQ ID NO:1 (and the corresponding modifications to the encoding nucleotides) will produce ficolin-associated polypeptides having functional and chemical characteristics similar to those of naturally occurring FAP. In contrast, substantial modifications in the functional and/or chemical characteristics of a ficolin-associated polypeptide may be accomplished by selecting substitutions in the amino acid sequence of SEQ ID NO:1 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of a ficolin-associated polypeptide, or to increase or decrease the affinity of a ficolin-associated polypeptide described herein.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human ficolin-associated polypeptide that are homologous with non-human ficolin-associated polypeptides, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±0.2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in SEQ ID NO:1 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a ficolin-associated polypeptide to such similar polypeptides. With such a comparison, one can identify residues and portions of the molecules that are conserved among similar polypeptides. It will be appreciated that changes in areas of a ficolin-associated polypeptide that are not conserved relative to such similar polypeptides would be less likely to adversely affect the biological activity and/or structure of the ficolin-associated polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a ficolin-associated polypeptide that correspond to amino acid residues that are important for activity or structure in similar polypeptides. One skilled in the art may opt for chemically similar amino acid substitutions for such predicted important amino acid residues of ficolin-associated polypeptides and other polypeptides of the invention.

One skilled in the art can also analyze the three-dimensional structure and amino acid sequence in relation to that structure in similar polypeptides. In view of that information, one skilled in the art may predict the alignment of amino acid residues of a ficolin-associated polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol, 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins, which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377-87 (1997); Sippl et al., Structure, 4(1):15-9 (1996)), "profile analysis" (Bowie et al., Science, 253:164-170 (1991); Gribskov et al., Meth. Enzymol., 183:146-159 (1990); Gribskov et al., Proc. Nat. Acad. Sci., 84(13):4355-4358 (1987)), and "evolutionary linkage" (See Home, supra, and Brenner, supra).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA, 89:10915-10919 (1992) for the BLOSUM 62 comparison matrix) is also used by the algorithm.

Preferred parameters for a polypeptide sequence comparison include the following:

Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following: Algorithm: Needleman et al., J. Mol Biol., 48:443-453 (1970); Comparison matrix: matches=+10, mismatch=0, Gap Penalty: 50, Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Preparation of Ficolin-Associated Polypeptides and Other Polypeptides of the Invention The invention also relates to a method of preparing human Ficolin-associated polypeptides and other polypeptides of the invention as mentioned above. The Ficolin-associated polypeptides and other polypeptides of the invention described herein may be produced by means of recombinant nucleic acid techniques. In general, a cloned wild-type FAP nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete amino acid and nucleotide sequences for human FAP is given by SEQ ID NO:1 and SEQ ID NO:2.

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of FAP, one may introduce the alteration(s) of choice. Likewise, procedures for preparing a DNA construct using polymerase chain reaction using specific primers are well known to per-sons skilled in the art (cf. PCR Protocols, 1990, Academic Press, San Diego, Calif., USA).

The polypeptides of the present invention can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcys-teine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an $E.\ coli$ S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in $Xenopus\ oocytes$ by microinjection of mutated mRNA and chemically aminoacylated suppressor tRNAs (Turcatti et al., J. Biol. Chem. 271:19991-8, 1996). Within a third method, $E.\ coli$ cells are cul-tured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

The nucleic acid construct encoding the Ficolin-associated polypeptides and other polypeptides of the invention of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Labora-tory, Cold Spring Harbor, N.Y., 1989).

The nucleic acid construct encoding a Ficolin-associated polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the human Ficolin-associated polypeptides and other polypeptides of the invention may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of syn-thetic, genomic or cDNA origin (as appropriate), the fragments corresponding to various parts of the entire nucleic acid construct, in accordance with standard techniques.

The nucleic acid construct is preferably a DNA construct. DNA sequences for use in producing Ficolin-associated polypeptides and other polypeptides according to the present invention will typically encode a pre-pro polypeptide at the amino-terminus of FAP to obtain proper posttranslational processing and secretion from the host cell.

The DNA sequences encoding the human Ficolin-associated polypeptides and other polypeptides according to the present invention are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Ficolin-associated polypeptides and other polypeptides according to the present invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing Ficolin-associated polypeptides and other polypeptides according to the present invention will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Ficolin-associated polypeptide in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

An example of a suitable promoter for use in insect cells is the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. Nos. 5,155,037; 5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Ficolin-associated polypeptides and other polypeptides according to the present invention may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the FAP sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from the human FAP gene or the bovine FAP gene. The expression vectors may also include a noncoding viral leader sequence, such as the adenovirus 2 tripartite leader, located between the promoter and the RNA splice sites; and enhancer sequences, such as the SV40 enhancer.

To direct the human Ficolin-associated polypeptides and other polypeptides of the present invention into the secretory pathway of the host cells, a secretory signal sequence (also known as a leader sequence, prepro sequence or pre sequence) may be provided in the recombinant vector. The secretory signal sequence is joined to the DNA sequences encoding the human Ficolin-associated polypeptides and other polypeptides according to the present invention in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Ficolin-associated polypeptides and other polypeptides according to the present invention into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the human Ficolin-associated polypeptides and other polypeptides according to the present invention. The function of the leader peptide is to allow the expressed peptide to be directed from the endoplasmic reticulum to the Golgi apparatus and further to a secretory vesicle for secretion into the culture medium (i.e. exportation of the human Ficolin-associated polypeptides and other polypeptides according to the present invention across the cell wall or at least through the cellular membrane into the periplasmic space of the yeast cell). The leader peptide may be the yeast alpha-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran Manduca sexta adipokinetic hormone precursor signal peptide (cf. U.S. Pat. No. 5,023,328).

The procedures used to ligate the DNA sequences coding for the human Ficolin-associated polypeptides and other polypeptides according to the present invention, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Ficolin-associated polypeptide of interest. Media generally include a carbon source, a nitrogen source, essential amino acids, essential sugars, vitamins, salts, phospholipids, protein and growth factors. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the human Ficolin-associated polypeptide of interest.

The host cell into which the DNA sequences encoding the human Ficolin-associated polypeptides and other polypeptides according to the present invention is introduced may be any cell, which is capable of producing the posttranslational modified human polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk- ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk- ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous poly-peptides there from are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human Ficolin-associated polypeptides and other polypeptides according to the present invention may be preceded by a signal sequence and optionally a leader sequence, e.g. as described above. Further examples of suitable yeast cells are strains of Kluyveromyces, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162, 222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214).

Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Ficolin-associated polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Ficolin-associated polypeptide produced by the cells may then be recovered from the culture medium by conventional procedures including separating the host cells from the medium by centrifugation or filtration, precipitating the protein aqueous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of polypeptide in question.

Transgenic animal technology may be employed to produce the Ficolin-associated polypeptides and other polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a 4.25 kbp DNA segment encompassing the 5' flanking promoter and non coding portion of the beta lactoglobulin gene (see Whitelaw et al., Biochem. J. 286: 31-39 (1992)). Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836-840 (1988); Palmiter et al., Proc. Natl. Acad. Sci. USA 88: 478-482 (1991); Whitelaw et al., Transgenic Res. 1: 3-13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g., the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the FAP sequence is replaced with corresponding sequences from a milk specific protein gene. Such replacement provides a putative tissue specific initiation environment to enhance expression. It is convenient to replace the entire FAP pre pro and 5' non coding sequences with those of, for example, the BLG gene, although smaller regions may be replaced.

For expression of Ficolin-associated polypeptides and other polypeptides according to the present invention in transgenic animals, a DNA segment encoding FAP is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified FAP. The secretory signal sequence may be a native FAP secretory signal sequence or may be that of another protein, such as a milk protein (see, for example, von Heijne, Nucl. Acids Res. 14: 4683 4690 (1986); and Meade et al., U.S. Pat. No. 4,873,316, which are incorporated herein by reference).

Construction of expression units for use in transgenic animals is conveniently carried out by inserting a FAP sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a FAP variant; thereby creating a gene fusion that includes the expression control sequences of the milk protein gene. In any event, cloning of the expression units in plasmids or other vectors facilitates the amplification of the FAP sequence. Amplification is conveniently carried out in bacterial (e.g. E. coli) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468-1474 (1988)) or site directed integration using embryonic stem (ES) cells (reviewed by Bradley et al., Bio/Technology 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179-183 (1988); Wall et al., Biol. Reprod. 32: 645-651 (1985); Buhler et al., Bio/Technology 8: 140-143 (1990); Ebert et al., Bio/Technology 9: 835 838 (1991); Krimpenfort et al., Bio/Technology 9: 844-847 (1991); Wall et al., J. Cell. Biochem. 49: 113-120 (1992); U.S. Pat. Nos. 4,873,191; 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380-7384 (1980); Gordon and Ruddle, Science 214: 1244-1246 (1981); Palmiter and Brinster, Cell 41: 343-345 (1985); Brinster et al., Proc. Natl. Acad. Sci. USA 82: 4438-4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179-183 (1988)). To summarise, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469-479 (1990); Edelbaum et al., J. Interferon Res. 12:449-453 (1992); Sijmons et al., Bio/Technology 8:217-221 (1990); and EP 0 255 378).

FAP Purification

The Ficolin-associated polypeptides and other polypeptides of the invention may be recovered from cell culture medium or milk. The Ficolin-associated polypeptides and other polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J. C. Janson and Lars Ryden, editors, VCH Publishers, New York, 1989). Preferably, they may be purified by affinity chromatography on an anti-FAP antibody column. Additional purification may be achieved by conventional chemical purification means, such as high performance liquid chromatography. Other methods of purification, including barium citrate precipitation, are known in the art, and may be applied to the purification of the novel Ficolin-associated polypeptides and other polypeptides described herein (see, for example, Scopes, R., Protein Purification, Springer-Verlag, N.Y., 1982).

For therapeutic purposes it is preferred that the Ficolin-associated polypeptides and other polypeptides of the invention are substantially pure. Thus, in a preferred embodiment of the invention the and other polypeptides of the invention is purified to at least about 90 to 95% homogeneity, preferably to at least about 98% homogeneity. Purity may be assessed by e.g. gel electrophoresis and amino-terminal amino acid sequencing.

The term "isolated polypeptide" refers to a polypeptide of the present invention that (1) has been separated from at least about 50 percent of polynucleotides, lipids, carbohydrates or other materials (i.e., contaminants) with which it is naturally associated. Preferably, the isolated polypeptide is substantially free from any other contaminating polypeptides or other contaminants that are found in its natural environment, which would interfere with its therapeutic, diagnostic, prophylactic or research use.

The term "microorganism" as used herein refers to bacteria, fungi, archaea, protists; microscopic plants and animals (such as green algae or plankton), the planarian and amoeba. Included within this definition are pathogenic microorganisms.

Assays

A general procedure for SDS-PAGE and Western blotting:
Electrophoresis was performed on 10% or 4-12% (w/v) Bis-Tris Polyacrylamide-gels with discontinuous buffers using the NuPAGE® system (Invitrogen) as recommended by the manufacture. Western blotting was performed using polyvinylidene difluoride membranes (PVDF-HyBond, GE-healthcare, Hilleroed, Denmark, cat. no. RPN303F), 2 µg/ml of biotin labeled primary monoclonal antibody and secondary visualization by HRP conjugated streptavidin (P0397, Dako, Glostrup, Denmark) diluted to 1:1500 in PBS, 0.05% Tween20. The membranes were developed with 0.04% 3-amino-9-ethylcarbazole (Sigma-aldrich, Broenby, Denmark, cat. no. A5754-100G) in acetone and 0.015% $H_2O_2$ in 50 mM sodium acetate buffer pH 5.

Co-Immunoprecipitation:

Immunoprecipitation of mannose binding lectin (MBL) serum complexes: 1 ml of normal human serum was diluted 1:1 in TBS (10 mM Tris, 140 mM NaCl, pH 7.5) and incubated end over end for 1 hour at 4° C. with 5 µg of the MBL specific mouse monoclonal antibody Hyb 131-11 (Bioporto, Gentofte, Denmark).

Immunoprecipitation of Ficolin-2 serum complexes: 0.5 ml of normal human serum was diluted 1:1 in TBS (10 mM Tris, 140 mM NaCl, pH 7.5) and incubated end over end for 1 hour at 4° C. with 5 µg of the Ficolin-2 specific mouse monoclonal antibody Hyb 219 (Munthe-Fog L, et al.

Immunoprecipitation of Ficolin-3 serum complexes: 0.2 ml of normal human serum was diluted 1:1 in TBS (10 mM Tris, 140 mM NaCl, pH 7.5) and incubated end over end for 1 hour at 4° C. with 5 µg of the Ficolin-3 specific mouse monoclonal antibody Hyb 334 (Munthe-Fog L, et al.

Immune complex precipitation was conducted with sheep anti mouse IgG conjugated magnetic dynal beads (Dynal-Invitrogen, Cat. No. 112.02D): After incubation with serum and primary antibodies (as above) $5 \times 10^7$ sheep anti mouse conjugated magnetic dynal beads were added and incubated for 30 min 4° C. The beads were magnetically separated and washed for three times with TBS-tween-$Ca^{2+}$ (10 mM Tris, 140 mM NaCl, 0.05% tween, 5 mM $CaCl_2$, pH 7.5) and finally boiled in SDS-loading buffer and analyzed by SDS-PAGE and western blotting with biotin labeled monoclonal antibody mAb-8B3 (reacting with an epitope on the heavy chain/A-chain shared by MASP-1 and -3).

Immunoaffinity purification of FAP: 10 mg of mAb-8B3 (reacting with an epitope on the heavy chain/A-chain shared by FAP, MASP-1 and -3) or 10 mg of rabbit polyclonal anti FAP antibodies were conjugated to CNBr activated sepharose as recommended by the manufacturer (GE-healthcare, Hilleroed, Denmark, cat. no. 17-0430-01) and packed onto a column.

Purification from serum: 150 ml of a pool of normal human serum was diluted 1:1 with TBS+0.5 M NaCl+10 mM EDTA (10 mM Tris, 640 mM NaCl, 10 mM EDTA, pH 7.5) and loaded on the columns described above. The columns were washed with 1 l of TBS+0.5 M NaCl+10 mM EDTA and 1 ml fractions were eluted with 1 M Glycine-HCl, pH 2.5 and analyzed by SDS-PAGE and western blotting with biotin labeled monoclonal antibody mAb-8B3.

Purification of recombinant FAP: 2-3 l of culture supernatant (from CHO serum free medium/Gibco-Invitrogen, cat. no. 12651-014) from Chinese hamster ovarian cells (CHO cells) expressing recombinant FAP (rFAP) was loaded on the antibody columns described above. The columns were washed with 1.5 l of TBS+0.5 M NaCl+10 mM EDTA and 1 ml fractions were eluted with 1 M Glycine-HCl, pH 2.5. The eluted fractions were analyzed by SDS-PAGE and coomassie staining.

Recombinant expression of FAP: Full-length cDNA inserted into the pcDNA5/FRT vector (Invitrogen, cat. no. V6010-20) was ordered from Genscript (Genscript, N.J., USA) and co-transfected with the pOG44 vector (Invitrogen, cat. no. V6005-20) into the CHO Flp-In cell line (Invitrogen, cat. no. R758-07) and selected and cloned as recommended by the manufacturer (Invitrogen). The cells were grown in Freestyle CHO serum free medium (Invitrogen, cat. no. 12651-014) and culture supernatants were harvested and analyzed.

Production of mono- and polyclonal antibodies: A peptide construct (ordered from Genscript, N.J., USA) of the FAP specific 17 C-terminal residues were coupled onto the toxoid form of tetanus and diphtheria using the cysteine coupling method with m-Maleimidobenzoyl-N-hydroxysuccinimide ester as recommended by the manufacturer (Thermo Fisher Scientific/Pierce, Ill., USA).

Six mice and two rabbits were each immunized three times (with 14 days intervals) with 25 μg antigen adsorbed onto Al(OH)$_3$ and Freunds incomplete adjuvant. The polyclonal antibody titers were assessed using ELISA with the different FAP peptides coupled to a protein carrier. Polyclonal rabbit antiserum (≈10 ml) was harvested 14 days after the first, second and third immunization.

Two mice were used for production of monoclonal antibodies. Four days prior to the fusion the mice received an intravenous injection of 25 μg antigen. The fusion was conducted as described elsewhere (Kohler, G. and C. Milstein. 1975. Continuous cultures of fused cells secreting antibody of predefined specificity. *Nature* 256:495-497).

Clones were selected by differential ELISA screening against peptides coupled to different protein carriers.

Functional complement assays: Ficolin-3 and MBL homozygous defect sera were used to investigate the function of FAP.

Ficolin-3 assay: Maxisorp plates (NUNC, Roskilde, Denmark, cat. no. 439454) were coated with acetylated bovine serum albumin at 5 μg/ml for 12 hours at 4° C. in coating buffer (15 mM Na$_2$CO$_3$, 35 mM NaHCO$_3$, pH 9.5). After blocking/washing four times in barbital/tween buffer (4 mM barbital, 145 mM NaCl, 2 mM CaCl$_2$, 1 mM MgCl$_2$, pH 7.4+0.05% Tween), recombinant human Ficolin-3 was added at 500 ng/ml l barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the 1$^{st}$ dimension on separate plates and incubated for 1 hour at 20° C. with shaking. After washing the plates twice in barbital/tween buffer, Ficolin-3 or MASP-2 deficient serum were added in serial dilutions in the 2$^{nd}$ dimension on the plates and incubated for 30 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 μl/well of Ortho-phenylene-diamine (OPD) (0.4 mg/ml) dissolved in citrate buffer (35 mM citric acid, 65 mM Na$_2$PO$_4$, pH 5) with 0.12‰ (v/v) H$_2$O$_2$. The enzyme reaction was stopped with 1 M H$_2$SO$_4$ and optical density (OD) levels were measured at 490 nm-650 nm using a V-max Kinetic-reader (Molecular Devices).

Mannose-Binding Lectin assay: Maxisorp plates (NUNC, Roskilde, Denmark, cat. no. 439454) were coated with mannan (Sigma-aldrich, Broenby, Denmark, cat. no. M7504-1G) at 10 μg/ml for 12 hours at 4° C. in coating buffer (15 mM Na$_2$CO$_3$, 35 mM NaHCO$_3$, pH 9.5). After blocking/washing four times in barbital/tween buffer (4 mM barbital, 145 mM NaCl, 2 mM CaCl$_2$, 1 mM MgCl$_2$, pH 7.4+0.05% Tween) recombinant human Mannose-Binding Lectin was added at 0.5 μg/ml l barbital/tween buffer and incubated for 1.5 hours at 20° C. with shaking. After washing the plates twice in barbital/tween buffer, recombinant FAP, human MASP-1, -2 or -3 as serum free medium culture supernatants were added in serial dilutions in the 1$^{st}$ dimension on separate plates and incubated for 1 hour at 20° C. with shaking. After washing the plates twice in barbital/tween buffer, MBL or MASP-2 deficient serum were added in serial dilutions in the 2$^{nd}$ dimension on the plates and incubated for 45 min at 37° C. After washing the plates four times in barbital/tween buffer the deposition of complement factor C4 was measured by incubation for 1 hour at 20° C. with polyclonal rabbit antibodies to human C4c (Dako, Glostrup, Denmark cat. no Q0369) diluted at 1:2000, followed by four washing steps and incubation with horseradish peroxidase conjugated swine anti rabbit antibodies (Dako, Glostrup, Denmark cat. no P0399) for 45 min at 20° C. The signal was obtained by the plates were developed with 100 μl/well of Ortho-phenylene-diamine (OPD) (0.4 ring/ml) dissolved in citrate buffer (35 mM citric acid, 65 mM Na$_2$PO$_4$, pH 5) with 0.12‰ (v/v) H$_2$O$_2$. The enzyme reaction was stopped with 1 M H$_2$SO$_4$ and optical density (OD) levels were measured at 490 nm-650 nm using a V-max Kinetic-reader (Molecular Devices).

Genotyping assay: Different genotyping assays may be conducted where the genotype is determined in individuals using biological assays. Different kind of assays could be used such as:

Hybridization-based methods
    Dynamic allele-specific hybridization
    Molecular beacons
    SNP microarrays
Enzyme-based methods
    Restriction fragment length polymorphism
    PCR-based methods
    Flap endonuclease
    Primer extension
    5'-nuclease
    Oligonucleotide ligase assay
Other post-amplification methods based on physical properties of DNA
    Single strand conformation polymorphism
    Temperature gradient gel electrophoresis
    Denaturing high performance liquid chromatography
    High-Resolution Melting of the entire amplicon
    SNPlex Sequencing
Administration and Pharmaceutical Compositions
Combination Treatments The ficolin-associated polypeptide as defined in the present specification may be administered simultaneously or sequentially with one or more proteins selected from Ficolin-1, 2, 3, and mannose-binding lectin (MBL). The factors may be supplied in single-dosage form wherein the single-dosage form contains both compounds, or in the form of a kit-of-parts comprising a preparation of a ficolin-associated polypeptide as a first unit dosage form and a preparation of the one or more other compound as a second unit dosage form. Whenever a first or second or third, etc., unit dose is mentioned throughout this specification this does not indicate the preferred order of administration, but is merely done for convenience purposes.

By "simultaneous" dosing of a preparation of a ficolin-associated polypeptide and a preparation of one or more other compound is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

Another object of the present invention is to provide a pharmaceutical formulation comprising a ficolin-associated polypeptide which is present in a serum/plasma concentration from 0 mg/ml to 1 mg/ml, and wherein the formulation has a pH from 2.0 to 10.0. The formulation may further comprise a buffer system, preservative(s), tonicity agent(s), chelating agent(s), stabilizers and surfactants. In some embodiments of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In other embodiments the pharmaceutical formulation is a freeze-dried formulation, whereto the physician or the patient adds solvents and/or diluents prior to use.

In other embodiments the pharmaceutical formulation is a dried formulation (e.g. freeze-dried or spray-dried) ready for use without any prior dissolution.

In a further aspect the invention relates to a pharmaceutical formulation comprising an aqueous solution of a ficolin-associated polypeptide, and a buffer, wherein the ficolin-associated polypeptide is present in a serum/plasma concentration from 0-1 mg/ml or above, and wherein the formulation has a pH from about 2.0 to about 10.0.

In a other embodiments of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In some embodiments the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In some embodiments the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In some embodiments, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/mi. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In some embodiments, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In some embodiments the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a non-ionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives—(e.g. sodium taurodihydrofusidate etc.), long-chain fatty acids and salts thereof C6-C12 (e.g. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dinnethylannn-nonio-1-propanesulfonates, 3-cholamido-1-propyldimethyl-ammonio-1-propanesulfonate, cationic surfactants (quaternary ammonium bases) (e.g. cetyl-trimethylammonium bromide, cetylpyridinium chloride), non-ionic surfactants (e.g. Dodecyl β-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Pharmaceutical compositions containing a ficolin-associated polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Topical administration may be a particular advantage in the treatment of conditions associated with local inflammation, such as in the treatment of inflammation associated with burn or other conditions associated with the skin. Accordingly, in some embodiments administration is by topical administration.

In some particular embodiments, eye droplets may be used in conditions associated with the eye, such as keratitis, such as diffuse lamellar keratitis (DLK).

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the ficolin-associated polypeptide, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the ficolin-associated polypeptide, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the ficolin-associated polypeptide in the form of a nasal or pulmonal spray. As a still further option, the pharmaceutical compositions containing the ficolin-associated polypeptide of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In some embodiments of the invention the pharmaceutical formulation comprising the ficolin-associated polypeptide is stable for more than 6 weeks of usage and for more than 3 years of storage. In other embodiments of the invention the pharmaceutical formulation comprising the ficolin-associated polypeptide is stable for more than 4 weeks of usage and for more than 3 years of storage. In a further embodiment of the invention the pharmaceutical formulation comprising the ficolin-associated polypeptide is stable for more than 4 weeks of usage and for more than two years of storage. In an even further embodiment of the invention the pharmaceutical formulation comprising the ficolin-associated polypeptide is stable for more than 2 weeks of usage and for more than two years of storage.

Specific Embodiments of the Invention

As described above the present invention relates to isolated ficolin-associated polypeptides as well as polypeptides comprising the amino acid sequence of SEQ ID NO:4 or variants or immunologic fragment thereof.

In some embodiments the polypeptide according to the present invention is substantially pure.

In some embodiments the polypeptide according to the present invention is capable of associating with mannose-binding lectin (MBL).

In some embodiments the polypeptide according to the present invention is capable of associating with any one of ficolin-1, ficolin-2, or ficolin-3.

In some embodiments the polypeptide according to the present invention is capable of associating with any one of C1q, lung surfactant proteins SP-A and/or SP-D, and intracellular collagen-like defense molecules, such as CLL-11.

In some embodiments the polypeptide according to the present invention is capable of associating with a specific acceptor protein, such as a specific receptor.

In some embodiments the polypeptide according to the present invention comprises the amino acid sequence 20-297 of SEQ NO:3, or a functional variant thereof.

In some embodiments the polypeptide according to the present invention comprises the amino acid sequence 20-380 of SEQ NO:1 or a functional variant thereof.

In some embodiments the polypeptide according to the present invention comprises the amino acid sequence 16-296 of SEQ ID NO:9 or a functional variant thereof.

In some embodiments the polypeptide according to the present invention has a molecular mass of about 40 kDa under non-reducing conditions on an SDS-PAGE.

In some embodiments the polypeptide according to the present invention is N-linked glycosylated at one or two amino acids corresponding to a position selected from 49 and 178 of SEQ NO:1.

In some embodiments the polypeptide according to the present invention is a recombinant protein.

In some embodiments the polypeptide according to the present invention is in homodimer form.

In some embodiments the polypeptide according to the present invention consists of the amino acid sequence 20-380 of SEQ ID NO 1.

In some embodiments the polypeptide according to the present invention comprises the amino acid sequence of SEQ ID NO:4 or variants or immunologic fragments thereof.

In some embodiments the polypeptide according to the present invention consist of SEQ ID NO:4, or variants or immunologic fragments thereof.

In some embodiments the polypeptide according to the present invention mediates phagocytosis of dying or dead cells, such as apoptotic cells, and/or cellular debris.

In some embodiments the polypeptide according to the present invention mediates phagocytosis of a microorganism.

In some embodiments the antibodies that specifically bind a polypeptide according to the present invention is a monoclonal antibody.

In some embodiments the antibodies that specifically bind a polypeptide according to the present invention is a polyclonal antibody.

In some embodiments the polypeptide according to the present invention has activity similar to other proteins with sequence homology, such as the engulfment adapter protein (GULP).

In some embodiments the isolated nucleic acid molecule encoding a polypeptide according to the present invention comprises a nucleotide sequence that is at least 70% identical to the sequence of SEQ NO:2.

In some embodiments the host cell according the present invention is a eukaryotic cell.

In some embodiments the host cell according the present invention is of mammalian origin.

In some embodiments the host cell according to the present invention is selected from the group consisting of CHO cells, HEK cells and BHK cells.

In some embodiments the polypeptide according to the present invention is for the treatment of any indications associated with inflammation, apoptosis and/or autoimmunity.

In some embodiments the polypeptide according to the present invention is for the treatment of any autoimmune conditions such as Addison's disease, autoimmune hemolytic anemia, autoimmune thyroiditis, Crohn's disease, Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, various allergies.

In some embodiments the polypeptide according to the present invention is for the treatment of any inflammatory disorder selected from the group consisting of appendicitis, peptic ulcer, gastric ulcer, duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, enteritis, Whipple's disease, allergy, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumotransmicroscopicsilicovolcanoconiosis, alveolitis, bronchiolitis, pharyngitis, pleurisy, sinusitis, influenza, respiratory syncytial virus infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillain-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosis, Goodpasture's syndrome, Behcet's syndrome, allograft rejection, graft-versus-host disease, Type I diabetes, ankylosing spondylitis, Berger's disease, Reiter's syndrome and Hodgkin's disease, keratitis, Type 2 diabetes, cystic fibrosis, myocardial infarction, reperfusion injury, stroke, dermatomyositis, metabolic syndrome, systemic inflammatory response syndrome, sepsis, multiple organ failure, disseminated intravascular coagulation, anaphylactic shock. Vascular complication and nephropathy associated with type 1 and/or type 2 diabetes, meningitis, bacterial septicemia, complicated malaria, atypic haemolytic uremic syndrome, haemolytic uremic syndrome, age related macular degeneration, paroxysmal nocturnal hemoglobinuria, snake venom bite, burn injury, and complications to organ transplantations.

In some embodiments the polypeptide according to the present invention is for the treatment of any inflammatory disorder selected from the group consisting of organ ischemia, reperfusion injury, organ necrosis, vasculitis, endocarditis, atherosclerosis, thrombophlebitis, pericarditis, myocarditis, myocardial ischemia, periarteritis nodosa, rheumatic fever, congestive heart failure, adult respiratory distress syndrome, cerebral infarction, cerebral embolism. Vascular complications and nephropathy associated with type 1 and/or type 2 diabetes.

In some embodiments the polypeptide according to the present invention is for the treatment of any indications associated with coagulation, thrombotic or coagulopathic related diseases.

In some embodiments the polypeptide according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplasty (PTCA), platelet deposition stroke, tumor growth, tumor metastasis, angiogenesis, thrombolysis, atherosclerosis, restenosis, such as arteriosclerosis and/or restenosis following angioplasty, acute and chronic indications such as inflammation, sepsis, septic chock, septicemia, hypotension, adult respiratory distress syndrome (ARDS), systemic inflammatory response syndrome (SIRS), disseminated intravascular coagulopathy (DIC), pulmonary embolism, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the polypeptide according to the present invention is for the treatment of an indication associated with coagulation, thrombotic or coagulopathic related diseases or disorders including inflammatory response and chronic thromboembolic diseases or disorders associated with fibrin formation including vascular disorders such as thrombosis, such as deep venous thrombosis, arterial thrombosis, post surgical thrombosis, coronary artery bypass graft (CABG), percutaneous transdermal coronary angioplasty (PTCA), platelet deposition stroke, tumor growth, tumor metastasis, angiogenesis, thrombolysis, atherosclerosis, restenosis, such as arteriosclerosis and/or restenosis following angioplasty, acute and chronic indications such as inflammation, pathological platelet deposition, myocardial infarction, or the prophylactic treatment of mammals with atherosclerotic vessels at risk for thrombosis, venoocclusive disease following peripheral blood progenitor cell (PBPC) transplantation, hemolytic uremic syndrome (HUS), and thrombotic thrombocytopenic purpura (TTP) and rheumatic fever.

In some embodiments the polypeptide according to the present invention is for preventing the occurrence of thromboembolic complications in identified high risk patients, such as those undergoing surgery or those with congestive heart failure.

In some embodiments the polypeptide according to the present invention is for the treatment of a medical condition associated with the heart.

In some embodiments the polypeptide according to the present invention is for the treatment of a medical condition associated with a deficiency in a ficolin-associated polypeptide.

EXAMPLE 1

Detection of alternative transcription of the MASP1 gene

Methods: In order to detect the three transcript variants of MASP1: MASP1, MASP3 and FAP, specific primers for each variant were design. PCR was set up with a common forward primer in exon 6 (5'-gcacccagagccacagtg-3') and specific reverse primers: MASP1 in exon 12 (5'-gccttccagtgtgtgggc-3'), MASP3 in exon 11 (5-gccttccagagtgtggtca-3') and FAP in exon 8a (5'-cgatctg-gagagcgaactc-3') (FIG. 1). PCR amplifications were carried out in 20-µl volumes containing: 50 ng liver cDNA (Clontech), 0.25 µM of each primer, 2.5 mM $MgCl_2$, 0.2 mM dNTP, 50 mM KCl, 10 mM Tris-HCl, pH 8.4, and 0.4 units of Platinum Taq DNA polymerase (Invitrogen). The PCR reactions were performed at the following cycling parameters: 10 min 94° C., 30 or 40 cycles (30 sec 94° C., 50 sec 58° C., 90 sec 72° C.), 10 min 72° C. Samples were analysed on 2% agarose gels.

Results: Alternative transcription of the MASP1 gene was detected in liver cDNA. The MASP1, MASP3, and FAP transcripts were amplified using a common forward primer located in exon 6 and specific reverse primers located in exon 12 (MASP1), exon 11 (MASP3), and exon 8a (FAP). MASP1 generates a fragment of 500 bp, MASP3 generates a fragment of 506 bp and FAP generates a fragment of 309 bp.

Tissue expression of the FAP fragment

Methods: Commercially available human tissue cDNA panels (Clontech) were investigated for MASP1, MASP3, and FAP expression with the same PCR assays as described above. Samples were analysed on 2% agarose gels.

Results: The tissue distributions of the MASP1, MASP3, and FAP genes were investigated in cDNA panels from Clontech (FIG. 2). MASP1, MASP3, and FAP transcripts were amplified using a common forward primer and specific reverse primers. GADPH was used as reference gene. All three genes were highly expressed in the liver, and additionally, FAP was strongly expressed in heart tissue (marked with black arrows). Minor expression of the FAP gene was detected in brain, colon, prostate, skeletal muscle, and small intestine (marked with white arrows).

DNA sequencing of the FAPexon8a of 100 individuals.

Methods: Direct sequencing of the exon 8a including the intron-exon boundary of the MASP1/MASP3/FAP gene spanning from position +44,083 to +44,431 relative to the translation ATG start site, was performed on genomic DNA templates from 100 healthy Caucasian individuals. The fragment was amplified by using a single primer set (forward: 5'-ctgttcttcacactggctg-3', reverse: 5'-ctgctgagatcatgttgttc-3'), where the forward primers contained a 5'-T7 sequence (5'-ttatacgactcacta-3'). PCR amplifications were carried out in 20-µl volumes containing: 50 ng genomic DNA, 0.25 µM of each primer, 2.5 mM $MgCl_2$, 0.2 mM dNTP, 50 mM KCl, 10 mM Tris·HCl, pH 8.4, and 0.4 units of Platinum Taq DNA polymerase (Invitrogen). The PCR reactions were performed at the following cycling parameters: 2 min 94° C., 15 cycles (30 sec 94° C., 60 sec 64° C., 60 sec 72° C.), 15 cycles (30 sec 94° C., 60 sec 58° C., 60 sec 72° C.), 5 min 72° C. and were sequenced in the forward direction using the ABI BigDye cycle sequencing terminator kit (Applied Biosystems, Foster City, Calif.) according to the protocol using 5'-biotinylated sequence primers. Sequence reactions were purified on the PyroMark Vacuum Prep Workstation (Biotage) using streptavidin beads (GenoVision). Sequence analysis was performed on an ABI Prism 3100 Genetic Analyser (Applied Biosystems). The resulting DNA sequences were aligned using BioEdit software, and DNA polymorphisms were confirmed visually from sequence electropherograms.

Results: All sequences were aligned using BioEdit software. No genetic variations in the 100 healthy individuals were observed in the exon 8a or the exon-intron regions.

EXAMPLE 2

Immunoprecipitation.

Specific immunoprecipitation of MAP-1 from serum was performed with the MAP-1 specific mAb 20C4 (raised against the 17 MAP-1 specific C-terminal peptide) or mAb 8B3, a monoclonal antibody reacting against the common heavy chain of MASP-1/3 used as control precipitation antibody. A total of 10 µg of anti MAP-1 or MASP-1/3 antibody was allowed to bind to sheep anti mouse or rabbit IgG Dynabeads (M-280, cat. 112.02D/112.04D, Dynal/Invitrogen). After a washing step the beads were applied to a pool of normal human serum (diluted 1:1 in TBS) and incubated end over end for 1 hour at 4° C. After final washing steps and magnetic separation the beads were boiled in SDS loading buffer and subjected to SDS-PAGE and western blotting probed with antibodies to MAP-1, MBL, and Ficolin-3.

The same precipitation procedure as described above was performed with mAbs to MBL (Hyb 131-11, Bioporto, Denmark), Ficolin-2 (FCN219) and Ficolin-3 (FCN334). To compensate for differences in serum concentrations of MBL, Ficolin-2 and -3 were precipitated from 1 ml, 300 µl and 100 µl serum, respectively. Samples were analyzed by SDS-PAGE and western blotting probed with pAb against MAP-1.

Immunohistochemistry.

CHO cells expressing rMAP-1 were grown in culture flasks in RPMI+10%. Cells were harvested at 80-90% confluence the cells were harvested and fixed for 24 h in 4% formaldehyde-PBS and subsequently embedded in paraffin. Six different human liver tissues and samples from two different myocardial tissues, two skeleton muscle tissues and two samples obtained from human aorta were also fixed and paraffin embedded as described above. Sections of 5 µm slices were obtained with a Leitz Wetzlar microtome and placed on glass slides and stored at 4° C. until assayed. Pre-treatments and analyses were performed as described previously. Primary antibodies were the MAP-1 specific monoclonal antibodies mAb 12B11 or affinity purified, monospecific rabbit anti-MAP-1 all diluted to 5 µg/ml. Isotype antibody controls were applied to the tissues at the same concentration. Secondary antibody was EnVision™ antibody (HRP-anti mouse or HRP-anti rabbit, Dako, Glostrup, Denmark). Analysis of staining patterns was conducted under a Leica DMLB2 microscope.

SDS-PAGE and Western Blotting.

Electrophoresis was performed on 10% or 4-12% (w/v) Bis-Tris Polyacrylamide-gels with discontinuous buffers using the NuPAGE® system (Invitrogen) essentially as described by the manufacturer. Western blotting was performed using polyvinylidene difluoride membranes (PVDF-HyBond, Amersham Bioscience), 2 µg/ml of primary mAbs and secondary visualization by HRP conjugated streptavidin (P0397, Dako) diluted to 1:1500 or HRP-Rabbit anti mouse IgG (P0260, Dako) diluted to 1:1000 in PBS, 0.05% Tween20. The membranes were developed with 3-amino-9-ethylcarbazole (Sigma) (0.04% in acetone) and 0.015% $H_2O_2$ in 50 mM sodium acetate buffer pH 5.

Complement Activation Assay.

The influence of MAP-1 on the MBL and Ficolin-3 mediated complement factor C4 deposition was assessed essentially as described previously. Briefly, mannan (MBL ligand) (Sigma-Aldrich M7504) or acetylated bovine serum albumin (Ficolin-3 ligand) was immobilized to Maxisorp ELISA plates (Nunc, Denmark) at 10 µg/ml. After washing with, rMBL or rFicolin-3 (0.4 µg/ml) was added and incubated for 1.5 hour. rMAP-1 or rMASP-2 was applied for 1 hour in two-fold serial dilutions in the first dimension followed by incubation for 45 min at 37° C. with serial dilutions of serum deficient of MBL or Ficolin-3 in the second dimension. The C4 deposition was measured using a pAb to C4c (Q0369, Dako, Glostrup/Denmark).

In addition we assessed the displacement of MASP-2 with MAP-1 using a pure system. rMASP-2 was pre-incubated for 45 min at 20° C. in serial dilutions in the first dimension on an rMBL/mannan matrix as described above followed by incubation with dilutions of rMAP-1 in the second dimension for 45 min at 20° C. Purified C4 (from Quidel, Calif., USA) was added at a concentration of 1 µg/ml and incubated for 45 min at 37° C. Detection was conducted as above.

Results.

MAP-1 co-precipitates with Ficolin-2, Ficolin-3 and MBL

To investigate a possible association of MAP-1 with MBL and Ficolin-3 we precipitated serum complexes using both anti MAP-1 mAb20C4 and a mAb against the common heavy chain of MASP-1 and MASP-3 (mAb8B3). The precipitates were subsequently analyzed by western blotting probed with antibodies to MAP-1, MBL, and Ficolin-3, respectively. We observed pronounced Ficolin-3 co-precipitation bands, but weaker bands were also seen with MBL (FIG. 24A). The samples wee not probed with antibodies against Ficolin-2 since they did not work in western blot. We then reversed the immunoprecipitation using mAbs against MBL, Ficolin-2 and Ficolin-3 to precipitate 1 ml, 300 µl and 100 µl serum, respectively, which was perform to adjust for differences in the serum concentration of MBL (2 µg/ml), Ficolin-2 (5 µg/ml) and Ficolin-3 (20 µg/ml), respectively. The samples were subsequently analyzed by western blotting probed with antibodies to MAP-1. Distinct MAP-1 bands were observed in the precipitates from Ficolin-2 and -3 and a much weaker band was apparent in the MBL precipitate, where immunoprecipitated rMAP-1 and serum MAP-1 served as controls (FIG. 24B).

MAP-1 inhibits complement activity of the lectin pathway.

Serum deficient of MBL and Ficolin-3 in combination with rMBL and rFicolin-3 were used to reconstitute for MBL and Ficolin-3 complement C4 activation activity. Mannan and acetylated BSA served as ligands for MBL and Ficolin-3, respectively. Both rMBL and rFicolin-3 were able to initiate C4 deposition in MBL and Ficolin-3 deficient sera, respectively (FIGS. 25A and 25D). Application of rMASP-2 resulted in a strong positive dose dependent enhancement of the C4 deposition via both the Ficolin-3 and MBL activation pathways (FIGS. 25B and 25E), whereas application of rMAP-1 resulted in a pronounced dose dependent inhibition of the C4 deposition via both pathways (FIGS. 25C and 25F).

In addition we addressed a possible displacement of MASP-2 with MAP-1 using a system of pure components comprising only of rMBL, rMASP-2, rMAP-1 and purified C4. rMASP-2 was pre-incubated with mannan/rMBL complexes in serial dilutions. Thereafter, rMAP-1 was added in varying concentrations followed by addition of purified C4. Application of rMAP-1 to the system clearly resulted in a dose dependent inhibition of C4 deposition (FIG. 26).

EXAMPLE 3

Determining Serum Concentration and Association Properties of the Novel MBL/Ficolin Associated Protein 1 (MAP-1).

A full-length non-tagged recombinant constructs of MAP-1 was generated and stably expressed in CHO-DG44 cells. Specific monoclonal antibodies against MAP-1 were raised. Also a quantitative ELISA for MAP-1 serum measurements was established and the associations between serum MAP-1 and Ficolin-2, -3 and MBL was examined by ELISA and density gradient fractionation.

Recombinant Proteins

Full length constructs of non-tagged human MAP-1 was expressed in CHO-DG44 cells as described elsewhere (Hummelshoj et al., Mol Immunol 44, 401-11, 2007; Larsen et al., J Biol Chem 279, 21302-11, 2004; Ma et al., 2009 J Biol Chem, Oct. 9; 284(41)) with the modifications that PowerCHO1 serum-free medium (Lonza, Vallensbaek/Denmark, www.lonza.com) was used as the expression medium. We used antibody affinity purification to purify rMAP-1 as described previously (Skjoedt et al., 2009; Immunobiology, Nov. 23). In brief 15 mg of the anti MAP-1 antibody (mAb 20C4) was covalently coupled to CNBr activated sepharose essentially as described by Pfeiffer et al. (Pfeiffer et al., J Immunol Methods 97, 1-9, 1987) and used as the purification matrix. The anti-MAP-1 column was also used to deplete MAP-1 from serum.

The generation of monoclonal antibodies was done as described previously (Skjoedt et al., J Biol Chem 285, 8234-43, 2010).

Electrophoresis was performed on 10% or 4-12% (w/v) Bis-Tris Polyacrylamide-gels with discontinuous buffers using the NuPAGE® system (Invitrogen) as recommended. Western blotting was performed using polyvinylidene difluoride membranes (PVDF-HyBond, GE Healthcare). The membranes were developed using 2 µg/ml of primary mAbs and secondary visualization by HRP conjugated streptavidin diluted to 1:1500 or HRP-Rabbit anti mouse IgG (P0397/P0260, Dako, Glostrup/Denmark, www.dako.com) with 0.04% 3-amino-9-ethylcarbazole (Sigma-Aldrich, Broendby/Denmark, www.sigmaaldrich.com)+0.015% $H_2O_2$ in 50 mM sodium acetate buffer pH5 as substrate.

rMAP-1 was treated with N-glycosidase-F/ENDO-F (N-glycosidase-F deglycosylation kit, Roche, Mannheim/Germany, www.roche.com) as recommended and described previously (Skjoedt et al., 2009). Products were analyzed by SDS-PAGE under reducing conditions followed by Coomassie staining or western blotting.

The specificity of the anti-MAP-1 mAb 20C4 has previously been demonstrated (Skjoedt et al., 2010). The mAb 20C4 was used as the catching antibody in a quantitative MAP-1 ELISA immobilized at 6 µg/ml to Maxisorb ELISA plates (NUNC™, Roskilde/Denmark, www.nuncbrand.com). Serial dilutions of the calibrator (rMAP-1 or rMAP-1 spiked in MAP-1 depleted serum) or donor serum samples were applied in PBS+0.05% Tween20+0.5% bovine serum and 10 mM EDTA. Detection antibody was biotin labeled mAb 8B3 reacting with the common chain of MASP-1, -3 and MAP-1 described previously (Skjoedt et al., 2010; Skjoedt et al., 2009) applied at 3 µg/ml.

The Ficolin-2 and -3 serum concentrations were determined as described by Munthe-Fog et al. and Hummelshoj et al. (Hummelshoj et al., Hum Mol Genet 14, 1651-8, 2005; Munthe-Fog et al., Scand J Immunol 65, 383-92, 2007; Munthe-Fog et al., Mol Immunol 45, 2660-6, 2008) and the MBL and MASP-3 serum concentrations were determined as described previously (Skjoedt et al., 2009).

Development was obtained with Ortho-phenylene-diamine (Dako, Glostrup/Denmark) and the enzyme reaction was stopped with 1M H2SO4 as recommended. Optical density (OD490 nm-650 nm) levels were measured using a V-max Kinetic-reader (Molecular Devices, Sunnyvale/Calif./U.S.).

The relative association between MAP-1 and MBL, Ficolin-2 and -3 was assessed essentially as described previously (Skjoedt et al., 2009) with the modification that the MAP-1 specific mAb 20C4 was used as capture antibody (coated at 6 µg/ml). Detection mAbs were biotin-labeled FCN-219 (Ficolin-2 specific) or FCN-334 (Ficolin-3 specific) (24-25), or Hyb 131-11 all applied at 2 µg/ml. The serum samples from the same 100 Danish blood donors as above were analyzed.

Normal human serum was subjected to sucrose gradient separation. 0.75 ml serum was loaded onto 40 ml centrifugation columns consisting of 10-30% sucrose gradients buffered in 10 mM Tris, 145 mM NaCl, 3 mM $CaCl_2$ and human serum albumin at 30 µg/ml. The loaded columns were centrifuged at 150.000×g in vacuum for 24 hours at 4° C. in a L70 Beckmann ultracentrifuge with a SW28 rotor head. 1.5 ml fractions were collected from the bottom and analyzed by specific ELISA or immunoblotting for the following antigens: MAP-1, MASP-1, MASP-2, MASP-3, sMAP, MBL, Ficolin-2 and Ficolin-3. The peaks of the serum IgM (19S) and IgG (7S) were also assessed indicating the molecular surface to mass ratio. Additionally the fractions were analyzed for the capacity to activate exogenously applied C4. Briefly, the fractions were applied in serial dilutions to ELISA plates coated with acetylated BSA (a Ficolin-3 ligand) or mannan (an MBL ligand) as described previously (Skjoedt et al., 2010) followed by incubation for 1 hour at 4° C. with shaking. The plates were then washed and incubated with purified C4 at 1 µg/ml for 1 hour at 37° C. The C4 deposition was subsequently measured with polyclonal antibodies to C4c (Q 0369, Dako, Glostrup, Denmark).

Statistical Analysis

Statistics (Spearman non-parametric correlation, non-parametric two-tailed t-test) and MAP-1, MBL, Ficolin-2 and -3 serum levels were calculated using Prism4 software (GraphPad Software, Inc., La Jolla/Calif./US, www.graphpad.com Results Purification and Characterization of rMAP-1

Expression of rMAP-1 in CHO DG44 cells resulted in a high yield in presence of 150 nM methotrexate (yield: 10-20 µg/ml in serum free medium). After purification rMAP-1 was analyzed in SDS-PAGE followed by Coomassie brilliant blue staining or immunoblotting. The SDS-PAGE/coomassie staining analysis revealed a band with an estimated reduced molecular mass of ~45 kDa (FIG. 27). Deglycosylation of rMAP-1 with N-glycosidase F resulted in a shift in molecular mass to ~40 kDa corresponding to the theoretical mass without signal peptide. This pattern was also observed with immunblotting using specific antibodies to MAP-1.

MAP-1 Serum Levels

We developed a quantitative ELISA to determine the serum level of MAP-1. The assay was based on the MAP-1 specific mAb 20C4 as capture antibody and a detection antibody (mAb 8B3) that recognizes the common heavy chain of MASP-1, -3 and MAP-1. Perfect parallelism was observed between the purified rMAP-1 calibrator and MAP-1 depleted serum spiked purified MAP-I at a known concentration with standard curve (FIG. 28A). We analyzed the serum level of MAP-1 in 100 Danish blood donors and found a mean of 240 ng/ml with a range of 115-466 ng/ml (FIG. 29A). We measured the MASP-3 serum level in the same group as described previously (Skjoedt et al., 2009) and plotted the MAP-1 and MASP-3 concentration (FIG. 29B). We found no correlation between the serum concentration of MAP-1 and MASP-3 although they represent alternative transcripts from the same gene.

We assessed the antigen and assay stability in serum and during freeze-thaw cycles (FIG. 29C). We observed that the assessment of MAP-1 was very robust regardless of freeze-thaw cycles.

Association between MAP-1 and Ficolin-2, -3 and MBL

In order to measure the interactions between MAP-1 and MBL, Ficolin-2 and -3, we developed three different ELISAs using mAb 20C4 as capture antibody and probing with biotin labeled mAbs: FCN-219 (Ficolin-2 specific), FCN-334 (Ficolin-3 specific) or Hyb 131-11 (MBL specific). We analyzed the same 100 donor serum samples as used for the MAP-1 determinations and assessed the serum association levels between MAP-1 and Ficolin-2, -3 and MBL given as relative O.D. 490-650 nm (FIG. 30A). In addition we measured the serum concentration of MBL, Ficolin-2 and -3 as previously (Skjoedt et al., 2009).

We found that MAP-1 exists in complex with MBL, Ficolin-2 and -3. It appears, however, that the major part of MAP-1 is associated to the ficolins and especially Ficolin-3 (p<0.0001) a pattern that has also been observed previously for MASP-3 (Skjoedt et al., 2009).

We plotted the serum concentrations of MAP-1, MBL, Ficolin-2 and -3 to the relative association levels and found that the association between MAP-1 and MBL is highly correlated to the MBL level (Spearman r: 0.92, p<0.0001) (FIG. 30B, top right hand side). In contrast to this the relative MAP-1 association to Ficolin-2 and -3 correlates to the serum level of MAP-I (Spearman r: 0.45 and 0.61, respectively, p<0.0001, FIG. 30B left hand side). Although we observed a certain correlation between the MAP-1 concentration and relative association to MBL and the Ficolin-3 concentration to the, the tendencies were less pronounced.

Density Gradient Fractionation

In order to investigate the distribution of MAP-1 in relation to associated molecules and to examine how much appears non-associated we subjected normal human serum to density fractionation using a 10-30% sucrose gradient and ultracentrifugation. Subsequently the collected fractions were analyzed for MAP-1, MASP-3, MBL, Ficolin-2 and -3 by ELISA (FIG. 31A) and MAP-1, MASP-1, -2 and -3, sMAP, MBL, Ficolin-2 and -3 by western blotting (FIG. 31B). The results showed that serum MAP-1 was only present in the fractions with the ficolins and MBL suggesting that MAP-1 does not exist as a non-associated molecule. The same pattern was observed for sMAP, MASP-1, -2 and -3. Additionally the data indicate that the majority of MAP-1, sMAP and MASP-1, -2 and -3 co-localize in the peak fractions of Ficolin-3. This distribution was also analyzed by size exclusion chromatography on a sephadex-200 column. An equivalent distribution pattern of the molecules was observed (data not shown).

Finally we assessed the capacity of the sucrose gradient fractions to activate exogenously applied C4. Solid phase mannan and acetylated BSA were used as ligands for MBL and Ficolin-3, respectively. We observed two different C4 deposition curves reflecting the peaks of Ficolin-3 and MBL complexes separated by the sucrose gradient (FIG. 31C).

Discussion

To investigate structural aspects and to establish the serum level of the novel MBL/Ficolin associated protein 1 (MAP-1), we expressed non-tagged, recombinant MAP-1 and generated specific antibodies against it. N-glycosidase F treatment and SDS-PAGE analysis indicated that MAP-I is glycosylated resulting in a molecular mass of ~45 kDa with N-glycans and ~40 kDa after deglycosylation equivalent to the calculated molecular mass from the deduced amino acid sequence without the signal peptide.

We used a monoclonal antibody generated against the MAP-1 specific C-terminal end to establish a quantitative MAP-1 ELISA and to determine the serum concentration range in 100 healthy Danish blood donors. We found a relatively low serum concentration (mean: 240 ng/ml, range 115-466 ng/ml) in the donor group compared to the MASP-3 concentration (mean: 6500 ng/ml). Additionally there was no correlation between the serum concentrations of the two proteins suggesting that although the two molecules are differentially spiced variants of the same gene the regulation of the expression is different. Recently, a significant difference in the tissue distribution of MASP-1, -3 and MAP-1 was described (Degn et al., 2009; Skjoedt et al., 2010). The finding of a major difference in the serum concentration between MASP-3 and MAP-I further supports the notion of a differential regulatory mechanism of the transcripts variants derived from the MASP1 gene.

We developed ELISA based assays to assess the relative association between serum MAP-1 and MBL, Ficolin-2 and -3, respectively. Additionally we determined the serum concentration of Ficolin-2, -3 and MBL in order to relate them to the relative association levels. The results show that MAP-1 is associated primarily to Ficolin-3 and Ficolin-2 and that the relative association to MBL appears less pronounced. It could be argued that this distribution reflects the difference in the mean serum concentration of MBL, Ficolin-2 and -3. However, although the MBL-MAP-I association correlates to the MBL concentration the same is not evident for Ficolin-2 where the MAP-I serum concentration correlates to the association level with Ficolin-2. The relative association between Ficolin-3 and MAP-1 was highly correlated with the MAP-1 serum concentration, while a positive correlation to the Ficolin-3 serum level was very weak. The above findings indicate that the major association between MAP-1 and Ficolin-2 and -3 is not simply due to the general higher concentration of Ficolin-2 and -3. This distribution pattern was further substantiated by analysis of serum subjected to density gradient separation. We found a clear tendency that not only MAP-1, but also sMAP, MASP-1, -2 and -3 co-localized with the Ficolin-3 peak fractions. This is a phenomenon that we have observed previously for MASP-3 (Skjoedt et al., 2009). The separation of the Ficolin-3 and MBL peak fractions was also assessed by the capacity to activate exogenously added C4 on acetylated BSA (a Ficolin-3 ligand) and mannan (an MBL ligand). The C4 deposition on the two different activation surfaces clearly illustrated the different peak fractions containing MBL or Ficolin-3 complexes.

The data from the sucrose gradient density analysis also indicated that the surface to mass ratio is higher for MBL than for Ficolin-2 and Ficolin-3, which supports the observations from a recent study suggesting that MBL has a very loose and open conformation in the quaternary structure (Jensenius et al., 2009). However the smaller surface to mass ratio of the ficolins could also reflect the molecular distribution with associated molecules such as MAP-1, sMAP and the MASPs. In this respect being more associated to MAP-1/sMAP/MASPs would result in a higher mass and a further migration through the density gradient.

In conclusion, we have shown that MAP-1 is present in low serum concentrations compared to MASP-3 and that MAP-1 and circulates in complex predominantly with the ficolins but also to some degree with MBL. Furthermore we could demonstrate that Ficolin-3 appears to be the main MAP-1 associated molecule among the LCP recognition molecules.

```
SEQ ID NO: 1
The complete 380 amino acid sequences for human FAP. (Two potential
glycosylation sites identified at amino acid position 49 and 178 are highlighted).
MRWLLLYYALCFSLSKASAHTVELNNMFGQIQSPGYPDSYPSDSEVTWNITVPDGFRIKLYFMHFNLESSYLCEYDYVKV        80

ETEDQVLATFCGRETTDTEQTPGQEVVLSPGSFMSITFRSDFSNEERFTGFDAHYMAVDVDECKEREDEELSCDHYCHNY       160

IGGYYCSCRFGYILHTDNRTCRVECSDNLFTQRTGVITSPDFPNPYPKSSECLYTIELEEGFMVNLQFEDIFDIEDHPEV       240

PCPYDYIKIKVGPKVLGPFCGEKAPEPISTQSHSVLILFHSDNSGENRGWRLSYRAAGNECPELQPPVHGKIEPSQAKYF       320

FKDQVLVSCDTGYKVLKDNVEMDTFQIECLKDGTWSNKIPTCKKNEIDLESELKSEQVTE.

SEQ ID NO: 2
The complete cDNA nucleotide sequences for human FAP.
atgaggtggctgcttctctattatgctctgtgcttctccctgtcaaaggcttcagcccacaccgtggagctaaacaata tgtttggccagatccagtcgcctggttatccagactcctatcccagtgattcagaggtgacttggaatatcactgtccc agatgggtttcggatcaagctttacttcatgcacttcaacttggaatcctcctacctttgtgaatatgactatgtgaag gtagaaactgaggaccaggtgctggcaaccttctgtggcagggagaccacagacacagagcagactcccggccaggagg tggtcctctccctggctccttcatgtccatcactttccggtcagatttctccaatgaggagcgtttcacaggctttga tgcccactacatggctgtggatgtggacgagtgcaaggagagggaggacgaggagctgtcctgtgaccactactgccac aactacattggcggctactactgctcctgccgcttcggctacatcctccacacagacaacaggacctgccgagtggagt gcagtgacaacctcttcactcaaaggactggggtgatcaccagccctgacttcccaaaccctt acccc aagagctctga atgcctgtataccatcgagctggaggagggtttcatggtcaacctgcagtttgaggacatatttgacattgaggaccat cctgaggtgccctgccctatgactacatcaagatcaaagttggtccaaaagttttggggcctttctgtggagagaaag ccccagaacccatcagcacccagagccacagtgtcctgatcctgttccatagtgacaactcgggagagaaccggggctg gaggctctcatacagggctgcaggaaatgagtgcccagagctacagcctcctgtccatgggaaaatcgagccctcccaa gccaagtatttcttcaaagaccaagtgctcgtcagctgtgacacaggctacaaagtgctgaaggataatgtggagatgg acacattccagattgagtgtctgaaggatgggacgtggagtaacaagattcccacctgtaaaaaaaatgaaatcgatct ggagagcgaactcaagtcagagcaagtgacagagtga.
```

```
SEQ NO: 3
Minimum sequence of a ficolin-associated polypeptide comprising the CUB1-EGF-
CUB2 domains including a signal peptide of amino acids 1-19. The sequence corresponds to
exon 2 to exon 6.
MRWLLLYYALCFSLSKASAHTVELNNMFGQIQSPGYPDSYPSDSEVTWNITVPDGFRIKLYFMHFNLESSYLCEYDYVKV          80

ETEDQVLATFCGRETTDTEQTPGQEVVLSPGSFMSITFRSDFSNEERFTGFDAHYMAVDVDECKEREDEELSCDHYCHNY         160

IGGYYCSCRFGYILHTDNRTCRVECSDNLFTQRTGVITSPDFPNPYPKSSECLYTIELEEGFMVNLQFEDIFDIEDHPEV         240

PCPYDYIKIKVGPKVLGPFCGEKAPEPISTQSHSVLILFHSDNSGENRGWRLSYRAA.

SEQ ID NO: 4
Unique terminal 17 amino acids of FAP
KNEIDLESELKSEQVTE.

SEQ ID NO: 5
Protein sequence of human MASP-1.
MRWLLLYYALCFSLSKASAHTVELNNMFGQIQSPGYPDSYPSDSEVTWNITVPDGFRIKLYFMHFNLESSYL

CEYDYVKVETEDQVLATFCGRETTDTEQTPGQEVVLSPGSFMSITFRSDFSNEERFTGFDAHYMAVDVDEC

KEREDEELSCDHYCHNYIGGYYCSCRFGYILHTDNRTCRVECSDNLFTQRTGVITSPDFPNPYPKSSECLYTI

ELEEGFMVNLQFEDIFDIEDHPEVPCPYDYIKIKVGPKVLGPFCGEKAPEPISTQSHSVLILFHSDNSGENRG

WRLSYRAAGNECPELQPPVHGKIEPSQAKYFFKDQVLVSCDTGYKVLKDNVEMDTFQIECLKDGTWSNKIP

TCKIVDCRAPGELEHGLITFSTRNNLTTYKSEIKYSCQEPYYKMLNNNTGIYTCSAQGVWMNKVLGRSLPTC

LPVCGLPKFSRKLMARIFNGRPAQKGTTPWIAMLSHLNGQPFCGGSLLGSSWIVTAAHCLHQSLDPEDPTLR

DSDLLSPSDFKIILGKHWRLRSDENEQHLGVKHTTLHPQYDPNTFENDVALVELLESPVLNAFVMPICLPEGP

QQEGAMVIVSGWGKQFLQRFPETLMEIEIPIVDHSTCQKAYAPLKKKVTRDMICAGEKEGGKDACAGDSGG

PMVTLNRERGQWYLVGTVSWGDDCGKKDRYGVYSYIHHNKDWIQRVTGVRN

SEQ ID NO: 6
cDNA sequence of human MASP-1
GAAGTCAGCCACACAGGATAAAGGAGGGAAGGGAAGGAGCAGATCTTTTCGGTAGGAAGACAGATTTTGT

TGTCAGGTTCCTGGGAGTGCAAGAGCAAGTCAAAGGAGAGAGAGAGGAGAGAGGAAAAGCCAGAGGGAGA

GAGGGGGAGAGGGGATCTGTTGCAGGCAGGGGAAGGCGTGACCTGAATGGAGAATGCCAGCCAATTCCAG

AGACACACAGGGACCTCAGAACAAAGATAAGGCATCACGGACACCACACCGGGCACGAGCTCACAGGCAA

GTCAAGCTGGGAGGACCAAGGCCGGGCAGCCGGGAGCACCCAAGGCAGGAAAATGAGGTGGCTGCTTCTC

TATTATGCTCTGTGCTTCTCCCTGTCAAAGGCTTCAGCCCACACCGTGGAGCTAAACAATATGTTTGGCC

AGATCCAGTCGCCTGGTTATCCAGACTCCTATCCCAGTGATTCAGAGGTGACTTGGAATATCACTGTCCC

AGATGGGTTTCGGATCAAGCTTTACTTCATGCACTTCAACTTGGAATCCTCCTACCTTTGTGAATATGAC

TATGTGAAGGTAGAAACTGAGGACCAGGTGCTGGCAACCTTCTGTGGCAGGGAGACCACAGACACAGAGC

AGACTCCCGGCCAGGAGGTGGTCCTCTCCCCTGGCTCCTTCATGTCCATCACTTTCCGGTCAGATTTCTC

CAATGAGGAGCGTTTCACAGGCTTTGATGCCCACTACATGGCTGTGGATGTGGACGAGTGCAAGGAGAGG

GAGGACGAGGAGCTGTCCTGTGACCACTACTGCCACAACTACATTGGCGGCTACTACTGCTCCTGCCGCT

TCGGCTACATCCTCCACACAGACAACAGGACCTGCCGAGTGGAGTGCAGTGACAACCTCTTCACTCAAAG

GACTGGGGTGATCACCAGCCCTGACTTCCCAAACCCTTACCCCAAGAGCTCTGAATGCCTGTATACCATC

GAGCTGGAGGAGGGTTTCATGGTCAACCTGCAGTTTGAGGACATATTTGACATTGAGGACCATCCTGAGG

TGCCCTGCCCCTATGACTACATCAAGATCAAAGTTGGTCCAAAAGTTTTGGGGCCTTTCTGTGGAGAGAA

AGCCCCCAGAACCCATCAGCACCCAGAGCCACAGTGTCCTGATCCTGTTCCATAGTGACAACTCGGGAGAG

AACCGGGGCTGGAGGCTCTCATACAGGGCTGCAGGAAATGAGTGCCCAGAGCTACAGCCTCCTGTCCATG

GGAAAATCGAGCCCTCCCAAGCCAAGTATTTCTTCAAAGACCAAGTGCTCGTCAGCTGTGACACAGGCTA

CAAAGTGCTGAAGGATAATGTGGAGATGGACACATTCCAGATTGAGTGTCTGAAGGATGGGACGTGGAGT
```

-continued

```
AACAAGATTCCCACCTGTAAAATTGTAGACTGTAGAGCCCCAGGAGAGCTGGAACACGGGCTGATCACCT

TCTCTACAAGGAACAACCTCACCACATACAAGTCTGAGATCAAATACTCCTGTCAGGAGCCCTATTACAA

GATGCTCAACAATAACACAGGTATATATACCTGTTCTGCCCAAGGAGTCTGGATGAATAAAGTATTGGGG

AGAAGCCTACCCACCTGCCTTCCAGTGTGTGGGCTCCCCAAGTTCTCCCGGAAGCTGATGGCCAGGATCT

TCAATGGACGCCCAGCCCAGAAAGGCACCACTCCCTGGATTGCCATGCTGTCACACCTGAATGGGCAGCC

CTTCTGCGGAGGCTCCCTTCTAGGCTCCAGCTGGATCGTGACCGCCGCACACTGCCTCCACCAGTCACTC

GATCCGGAAGATCCGACCCTACGTGATTCAGACTTGCTCAGCCCTTCTGACTTCAAAATCATCCTGGGCA

AGCATTGGAGGCTCCGGTCAGATGAAAATGAACAGCATCTCGGCGTCAAACACACCACTCTCCACCCCCA

GTATGATCCCAACACATTCGAGAATGACGTGGCTCTGGTGGAGCTGTTGGAGAGCCCAGTGCTGAATGCC

TTCGTGATGCCCATCTGTCTGCCTGAGGGACCCCAGCAGGAAGGAGCCATGGTCATCGTCAGCGGCTGGG

GGAAGCAGTTCTTGCAAAGGTTCCCAGAGACCCTGATGGAGATTGAAATCCCGATTGTTGACCACAGCAC

CTGCCAGAAGGCTTATGCCCCGCTGAAGAAGAAAGTGACCAGGGACATGATCTGTGCTGGGGAGAAGGAA

GGGGGAAAGGACGCCTGTGCGGGTGACTCTGGAGGCCCCATGGTGACCCTGAATAGAGAAAGAGGCCAGT

GGTACCTGGTGGGCACTGTGTCCTGGGGTGATGACTGTGGGAAGAAGGACCGCTACGGAGTATACTCTTA

CATCCACCACAACAAGGACTGGATCCAGAGGGTCACCGGAGTGAGGAACTGAATTTGGCTCCTCAGCCCC

AGCACCACCAGCTGTGGGCAGTCAGTAGCAGAGGACGATCCTCCGATGAAAGCAGCCATTTCTCCTTTCC

TTCCTCCCATCCCCCCTCCTTCGGCCTATCCATTACTGGGCAATAGAGCAGGTATCTTCACCCCCTTTTC

ACTCTCTTTAAAGAGATGGAGCAAGAGAGTGGTCAGAACACAGGCCGAATCCAGGCTCTATCACTTACTA

GTTTGCAGTGCTGGGCAGGTGACTTCATCTCTTCGAACTTCAGTTTCTTCATAAGATGGAAATGCTATAC

CTTACCTACCTCGTAAAAGTCTGATGAGGAAAAGATTAACTAATAGATGCATAGCACTTAACAGAGTGCA

TAGCATACACTGTTTTCAATAAATGCACCTTAGCAGAAGGTCGATGTGTCTACCAGGCAGACGAAGCTCT

CTTACAAACCCCTGCCTGGGTCTTAGCATTGATCAGTGACACACCTCTCCCCTCAACCTTGACCATCTCC

ATCTGCCCTTAAATGCTGTATGCTTTTTTGCCACCGTGCAACTTGCCCAACATCAATCTTCACCCTCATC

CCTAAAAAAGTAAAACAGACAAGGTTCTGAGTCCTGTGGTATGTCCCCTAGCAAATGTAACTAGGAACAT

GCACTAGATGACAGATTGCGGGAGGGCCTGAGAGAAGCAGGGACAGGAGGGAGCCTGGGGATTGTGGTTT

GGGAAGGCAGACACCTGGTTCTAGAACTAGCTCTGCCCTTAGCCCCCTGTATGACCCTATGCAAGTCCTC

CTCCCTCATCTCAAAGGGTCCTCAAAGCTCTGACGATCTAAGATACAATGAAGCCATTTTCCCCCTGATA

AGATGAGGTAAAGCCAATGTAACCAAAAGGCAAAAATTACAATCGGTTCAAAGGAACTTTGATGCAGACA

AAATGCTGCTGCTGCTGCTCCTGAAATACCCACCCCTTTCCACTACGGGTGGGTTCCCAAGGACATGGGA

CAGGCAAAGTGTGAGCCAAAGGATCCTTCCTTATTCCTAAGCAGAGCATCTGCTCTGGGCCCTGGCCTCC

TTCCCTTCTTGGGAAACTGGGCTGCATGAGGTGGGCCCTGGTAGTTTGTACCCCAGGCCCCTATACTCTT

CCTTCCTATGTCCACAGCTGACCCCAAGCAGCCGTTCCCCGACTCCTCACCCCTGAGCCTCACCCTGAAC

TCCCTCATCTTGCAAGGCCATAAGTGTTTTCCAAGCAAAATGCCTCTCCCATCCTCTCTCAGGAAGCTTC

TAGAGACTTTATGCCCTCCAGAGCTCCAAGATATAAGCCCTCCAAGGGATCAGAAGCTCCAAGTTCCTGT

CTTCTGTTTTATAGAAATTGATCTTCCCTGGGGGACTTTAACTCTTGACCTGTATGCAGCTGTTGGAGTA

ATTCCAGGTCTCTTGAAAAAAAAGAGGAAGATAATGGAGAATGAGAACATATATATATATATATTAAGCC

CCAGGCTGAATACTCAGGGACAGCAATTCACAGCCTGCCTCTGGTTCTATAAACAAGTCATTCTACCTCT

TTGTGCCCTGCTGTTTATTCTGTAAGGGGAAGGTGGCAATGGGACCCAGCTCCATCAGACACTTGTCAAG

CTAGCAGAAACTCCATTTTCAATGCCAAAGAAGAACTGTAATGCTGTTTTGGAATCATCCCAAGGCATCC

CAAGACACCATATCTTCCCATTTCAAGCACTGCCTGGGCACACCCCAACATCCCAGGCTGTGGTGGCTCC

TGTGGGAACTACCTAGATGAAGAGAGTATCATTTATACCTTCTAGGAGCTCCTATTGGGAGACATGAAAC
```

-continued

ATATGTAATTGACTACCATGTAATAGAACAAACCCTGCCAAGTGCTGCTTTGGAAAGTCATGGAGGTAAA

AGAAAGACCATTC

SEQ ID NO: 7
Protein sequence of human MASP-3.
MRWLLLYYALCFSLSKASAHTVELNNMFGQIQSPGYPDSYPSDSEVTWNITVPDGFRIKLYFMHFNLESSYLCEYDYVKVETEDQ VLATFCGRETTDTEQTPGQEVVLSPGSFMSITFRSDFSNEERFTGFDAHYMAVDVDECKEREDEELSCDHYCHNYIGGYYCSCRF GYILHTDNRTCRVECSDNLFTQRTGVITSPDFPNPYPKSSECLYTIELEEGFMVNLQFEDIFDIEDHPEVPCPYDYIKIKVGPKV LGPFCGEKAPEPISTQSHSVLILFHSDNSGENRGWRLSYRAAGNECPELQPPVHGKIEPSQAKYFFKDQVLVSCDTGYKVLKDNV EMDTFQIECLKDGTWSNKIPTCKIVDCRAPGELEHGLITFSTRNNLTTYKSEIKYSCQEPYYKMLNNNTGIYTCSAQGVWMNKVL GRSLPTCLPECGQPSRSLPSLVKRIIGGRNAEPGLFPWQALIVVEDTSRVPNDKWFGSGALLSASWILTAAHVLRSQRRDTTVIP VSKEHVTVYLGLHDVRDKSGAVNSSAARVVLHPDFNIQNYNHDIALVQLQEPVPLGPHVMPVCLPRLEPEGPAPHMLGLVAGWGI SNPNVTVDEIISSGTRTLSDVLQYVKLPVVPHAECKTSYESRSGNYSVTENMECAGYIEGGKDTCLGDSGGAFVIFDDLSQRWVV

QGLVSWGGPEECGSKQVYGVYTKVSNYVDWVWEQMGLPQSVVEPQVER

SEQ ID NO: 8
cDNA sequence of human MASP-3
GAAGTCAGCCACACAGGATAAAGGAGGGAAGGGAAGGAGCAGATCTTTTCGGTAGGAAGACAGATTTTGT

TGTCAGGTTCCTGGGAGTGCAAGAGCAAGTCAAAGGAGAGAGAGAGGAGAGAGGAAAAGCCAGAGGGAGA

GAGGGGGAGAGGGGATCTGTTGCAGGCAGGGGAAGGCGTGACCTGAATGGAGAATGCCAGCCAATTCCAG

AGACACACAGGGACCTCAGAACAAAGATAAGGCATCACGGACACCACACCGGGCACGAGCTCACAGGCAA

GTCAAGCTGGGAGGACCAAGGCCGGGCAGCCGGGAGCACCCAAGGCAGGAAAATGAGGTGGCTGCTTCTC

TATTATGCTCTGTGCTTCTCCCTGTCAAAGGCTTCAGCCCACACCGTGGAGCTAAACAATATGTTTGGCC

AGATCCAGTCGCCTGGTTATCCAGACTCCTATCCCAGTGATTCAGAGGTGACTTGGAATATCACTGTCCC

AGATGGGTTTCGGATCAAGCTTTACTTCATGCACTTCAACTTGGAATCCTCCTACCTTTGTGAATATGAC

TATGTGAAGGTAGAAACTGAGGACCAGGTGCTGGCAACCTTCTGTGGCAGGGAGACCACAGACACAGAGC

AGACTCCCGGCCAGGAGGTGGTCCTCTCCCCTGGCTCCTTCATGTCCATCACTTTCCGGTCAGATTTCTC

CAATGAGGAGCGTTTCACAGGCTTTGATGCCCACTACATGGCTGTGGATGTGGACGAGTGCAAGGAGAGG

GAGGACGAGGAGCTGTCCTGTGACCACTACTGCCACAACTACATTGGCGGCTACTACTGCTCCTGCCGCT

TCGGCTACATCCTCCACACAGACAACAGGACCTGCCGAGTGGAGTGCAGTGACAACCTCTTCACTCAAAG

GACTGGGGTGATCACCAGCCCTGACTTCCCAAACCCTTACCCCAAGAGCTCTGAATGCCTGTATACCATC

GAGCTGGAGGAGGGTTTCATGGTCAACCTGCAGTTTGAGGACATATTTGACATTGAGGACCATCCTGAGG

TGCCCTGCCCCTATGACTACATCAAGATCAAAGTTGGTCCAAAAGTTTTGGGGCCTTTCTGTGGAGAGAA

AGCCCCAGAACCCATCAGCACCCAGAGCCACAGTGTCCTGATCCTGTTCCATAGTGACAACTCGGGAGAG

AACCGGGGCTGGAGGCTCTCATACAGGGCTGCAGGAAATGAGTGCCCAGAGCTACAGCCTCCTGTCCATG

GGAAAATCGAGCCCTCCCAAGCCAAGTATTTCTTCAAAGACCAAGTGCTCGTCAGCTGTGACACAGGCTA

CAAAGTGCTGAAGGATAATGTGGAGATGGACACATTCCAGATTGAGTGTCTGAAGGATGGGACGTGGAGT

AACAAGATTCCCACCTGTAAAATTGTAGACTGTAGAGCCCCAGGAGAGCTGGAACACGGGCTGATCACCT

TCTCTACAAGGAACAACCTCACCACATACAAGTCTGAGATCAAATACTCCTGTCAGGAGCCCTATTACAA

GATGCTCAACAATAACACAGGTATATATACCTGTTCTGCCCAAGGAGTCTGGATGAATAAAGTATTGGGG

AGAAGCCTACCCACCTGCCTTCCAGAGTGTGGTCAGCCCTCCCGCTCCCTGCCAAGCCTGGTCAAGAGGA

TCATTGGGGGCCGAAATGCTGAGCCTGGCCTCTTCCCGTGGCAGGCCCTGATAGTGGTGGAGGACACTTC

GAGAGTGCCAAATGACAAGTGGTTTGGGAGTGGGGCCCTGCTCTCTGCGTCCTGGATCCTCACAGCAGCT

CATGTGCTGCGCTCCCAGCGTAGAGACACCACGGTGATACCAGTCTCCAAGGAGCATGTCACCGTCTACC

```
                                    -continued
TGGGCTTGCATGATGTGCGAGACAAATCGGGGGCAGTCAACAGCTCAGCTGCCCGAGTGGTGCTCCACCC

AGACTTCAACATCCAAAACTACAACCACGATATAGCTCTGGTGCAGCTGCAGGAGCCTGTGCCCCTGGGA

CCCCACGTTATGCCTGTCTGCCTGCCAAGGCTTGAGCCTGAAGGCCCGGCCCCCACATGCTGGGCCTGG

TGGCCGGCTGGGGCATCTCCAATCCCAATGTGACAGTGGATGAGATCATCAGCAGTGGCACACGGACCTT

GTCAGATGTCCTGCAGTATGTCAAGTTACCCGTGGTGCCTCACGCTGAGTGCAAAACTAGCTATGAGTCC

CGCTCGGGCAATTACAGCGTCACGGAGAACATGTTCTGTGCTGGCTACTACGAGGGCGGCAAAGACACGT

GCCTTGGAGATAGCGGTGGGGCCTTTGTCATCTTTGATGACTTGAGCCAGCGCTGGGTGGTGCAAGGCCT

GGTGTCCTGGGGGGACCTGAAGAATGCGGCAGCAAGCAGGTCTATGGAGTCTACACAAAGGTCTCCAAT

TACGTGGACTGGGTGTGGGAGCAGATGGGCTTACCACAAAGTGTTGTGGAGCCCCAGGTGGAACGGTGAG

CTGACTTACTTCCTCGGGGCCTGCCTCCCCTGAGCGAAGCTACACCGCACTTCCGACAGCACACTCCACA

TTACTTATCAGACCATATGGAATGGAACACACTGACCTAGCGGTGGCTTCTCCTACCGAGACAGCCCCCA

GGACCCTGAGAGGCAGAGTGTGGTATAGGGAAAAGGCTCCAGGCAGGAGACCTGTGTTCCTGAGCTTGTC

CAAGTCTCTTTCCCTGTCTGGGCCTCACTCTACCGAGTAATACAATGCAGGAGCTCAACCAAGGCCTCTG

TGCCAATCCCAGCACTCCTTTCCAGGCCATGCTTCTTACCCCAGTGGCCTTTATTCACTCCTGACCACTT

ATCAAACCCATCGGTCCTACTGTTGGTATAACTGAGCTTGGACCTGACTATTAGAAAATGGTTTCTAACA

TTGAACTGAATGCCGCATCTGTATATTTTCCTGCTCTGCCTTCTGGGACTAGCCTTGGCCTAATCCTTCC

TCTAGGAGAAGAGCATTCAGGTTTTGGGAGATGGCTCATAGCCAAGCCCCTCTCTCTTAGTGTGATCCCT

TGGAGCACCTTCATGCCTGGGGTTTCTCTCCCAAAAGCTTCTTGCAGTCTAAGCCTTATCCCTTATGTTC

CCCATTAAAGGAATTTCAAAAGACATGGAGAAAGTTGGGAAGGTTTGTGCTGACTGCTGGGAGCAGAATA

GCCGTGGGAGGCCCACCAAGCCCTTAAATTCCCATTGTCAACTCAGAACACATTTGGGCCCATATGCCAC

CCTGGAACACCAGCTGACACCATGGGCGTCCACACCTGCTGCTCCAGACAAGCACAAAGCAATCTTTCAG

CCTTGAAATGTATTATCTGAAAGGCTACCTGAAGCCCAGGCCCGAATATGGGACTTAGTCGATTACCTG

GAAAAGAAAAGACCCACACTGTGTCCTGCTGTGCTTTTGGGCAGGAAAATGGAAGAAAGAGTGGGGTGG

GCACATTAGAAGTCACCCAAATCCTGCCAGGCTGCCTGGCATCCCTGGGGCATGAGCTGGGCGGAGAATC

CACCCCGCAGGATGTTCAGAGGGACCCCACTCCTTCATTTTTCAGAGTCAAAGGAATCAGAGGCTCACCCA

TGGCAGGCAGTGAAAAGAGCCAGGAGTCCTGGGTTCTAGTCCCTGCTCTGCCCCCAACTGGCTGTATAAC

CTTTGAAAAATCATTTTCTTTGTCTGAGTCTCTGGTTCTCCGTCAGCAACAGGCTGGCATAAGGTCCCCT

GCAGGTTCCTTCTAGCTGGAGCACTCAGAGCTTCCCTGACTGCTAGCAGCCTCTCTGGCCCTCACAGGGC

TGATTGTTCTCCTTCTCCCTGGAGCTCTCTCTCCTGAAAATCTCCATCAGAGCAAGGCAGCCAGAGAAGC

CCCTGAGAGGGAATGATTGGGAAGTGTCCACTTTCTCAACCGGCTCATCAAACACACTCCTTTGTCTATG

AATGGCACATGTAAATGATGTTATATTTTGTATCTTTTATATCATATGCTTCACCATTCTGTAAAGGGCC

TCTGCATTGTTGCTCCCATCAGGGGTCTCAAGTGGAAATAAACCCTCGTGGATAACCAAAAAAAAAAAAA

AAAAAAA

SEQ ID NO: 9
Protein sequence of human MASP-2
MRLLTLLGLLCGSVATPLGPKWPEPVFGRLASPGFPGEYANDQERRWTLTAPPGYRLRLYFTHFDLELSHLCE

YDFVKLSSGAKVLATLCGQESTDTERAPGKDTFYSLGSSLDITFRSDYSNEKPFTGFEAFYAAEDIDECQVAP

GEAPTCDHHCHNLLGGFYCSCRAGYVLHRNKRTCSALCSGQVFTQRSGELSSPEYPRPYPKLSSCTYSISLE

EGFSVILDFVESFDVETHPETLCPYDFLKIQTDREEHGPFCGKTLPHRIETKSNTVTITFVTDESGDHTGWKI

HYTSTAQPCPYPMAPPNGHVSPVQAKYILKDSFSIFCETGYELLQGHLPLKSFTAVCQKDGSWDRPMPACSI

VDCGPPDDLPSGRVEYITGPGVTTYKAVIQYSCEETFYTMKVNDGKYVCEADGFWTSSKGEKSLPVCEPVC

GLSARTTGGRIYGGQKAKPGDFPWQVLILGGTTAAGALLYDNWVLTAAHAVYEQKHDASALDIRMGTLKRL
```

SPHYTQAWSEAVFIHEGYTHDAGFDNDIALIKLNNKVVINSNITPICLPRKEAESFMRTDDIGTASGWGLTQ
RGFLARNLMYVDIPIVDHQKCTAAYEKPPYPRGSVTANMLCAGLESGGKDSCRGDSGGALVFLDSETERWF
VGGIVSWGSMNCGEAGQYGVYTKVINYIPWIENIISDF

SEQ ID NO: 10
cDNA sequence of human MASP-2
GGCCAGCTGGACGGGCACACCATGAGGCTGCTGACCCTCCTGGGCCTTCTGTGTGGCTCGGTGGCCACCC
CCTTGGGCCCGAAGTGGCCTGAACCTGTGTTCGGGCGCCTGGCATCCCCCGGCTTTCCAGGGGAGTATGC
CAATGACCAGGAGCGGCGCTGGACCCTGACTGCACCCCCGGCTACCGCCTGCGCCTCTACTTCACCCAC
TTCGACCTGGAGCTCTCCCACCTCTGCGAGTACGACTTCGTCAAGCTGAGCTCGGGGGCCAAGGTGCTGG
CCACGCTGTGCGGGCAGGAGAGCACAGACACGGAGCGGGCCCCTGGCAAGGACACTTTCTACTCGCTGGG
CTCCAGCCTGGACATTACCTTCCGCTCCGACTACTCCAACGAGAAGCCGTTCACGGGGTTCGAGGCCTTC
TATGCAGCCGAGGACATTGACGAGTGCCAGGTGGCCCCGGGAGAGGCGCCCACCTGCGACCACCACTGCC
ACAACCACCTGGGCGGTTTCTACTGCTCCTGCCGCGCAGGCTACGTCCTGCACCGTAACAAGCGCACCTG
CTCAGCCCTGTGCTCCGGCCAGGTCTTCACCCAGAGGTCTGGGGAGCTCAGCAGCCCTGAATACCCACGG
CCGTATCCCAAACTCTCCAGTTGCACTTACAGCATCAGCCTGGAGGAGGGGTTCAGTGTCATTCTGGACT
TTGTGGAGTCCTTCGATGTGGAGACACACCCTGAAACCCTGTGTCCCTACGACTTTCTCAAGATTCAAAC
AGACAGAGAAGAACATGGCCCATTCTGTGGGAAGACATTGCCCCACAGGATTGAAACAAAAAGCAACACG
GTGACCATCACCTTTGTCACAGATGAATCAGGAGACCACACAGGCTGGAAGATCCACTACACGAGCACAG
CGCAGCCTTGCCCTTATCCGATGGCGCCACCTAATGGCCACGTTTCACCTGTGCAAGCCAAATACATCCT
GAAAGACAGCTTCTCCATCTTTTGCGAGACTGGCTATGAGCTTCTGCAAGGTCACTTGCCCCTGAAATCC
TTTACTGCAGTTTGTCAGAAAGATGGATCTTGGGACCGGCCAATGCCCGCGTGCAGCATTGTTGACTGTG
GCCCTCCTGATGATCTACCCAGTGGCCGAGTGGAGTACATCACAGGTCCTGGAGTGACCACCTACAAAGC
TGTGATTCAGTACAGCTGTGAAGAGACCTTCTACACAATGAAAGTGAATGATGGTAAATATGTGTGTGAG
GCTGATGGATTCTGGACGAGCTCCAAAGGAGAAAAATCACTCCCAGTCTGTGAGCCTGTTTGTGGACTAT
CAGCCCGCACAACAGGAGGGCGTATATATGGAGGGCAAAAGGCAAAACCTGGTGATTTTCCTTGGCAAGT
CCTGATATTAGGTGGAACCACAGCAGCAGGTGCACTTTTATATGACAACTGGGTCCTAACAGCTGCTCAT
GCCGTCTATGAGCAAAAACATGATGCATCCGCCCTGGACATTCGAATGGGCACCCTGAAAAGACTATCAC
CTCATTATACACAAGCCTGGTCTGAAGCTGTTTTTATACATGAAGGTTATACTCATGATGCTGGCTTTGA
CAATGACATAGCACTGATTAAATTGAATAACAAAGTTGTAATCAATAGCAACATCACGCCTATTTGTCTG
CCAAGAAAAGAAGCTGAATCCTTTATGAGGACAGATGACATTGGAACTGCATCTGGATGGGGATTAACCC
AAAGGGGTTTTCTTGCTAGAAATCTAATGTATGTCGACATACCGATTGTTGACCATCAAAAATGTACTGC
TGCATATGAAAAGCCACCCTATCCAAGGGGAAGTGTAACTGCTAACATGCTTTGTGCTGGCTTAGAAAGT
GGGGGCAAGGACAGCTGCAGAGGTGACAGCGGAGGGGCACTGGTGTTTCTAGATAGTGAAACAGAGAGGT
GGTTTGTGGGAGGAATAGTGTCCTGGGGTTCCATGAATTGTGGGGAAGCAGGTCAGTATGGAGTCTACAC
AAAAGTTATTAACTATATTCCCTGGATCGAGAACATAATTAGTGATTTTAACTTGCGTGTCTGCAGTCA
AGGATTCTTCATTTTTAGAAATGCCTGTGAAGACCTTGGCAGCGACGTGGCTCGAGAAGCATTCATCATT
ACTGTGGACATGGCAGTTGTTGCTCCACCCAAAAAAACAGACTCCAGGTGAGGCTGCTGTCATTTCTCCA
CTTGCCAGTTTAATTCCAGCCTTACCCATTGACTCAAGGGGACATAAACCACGAGAGTGACAGTCATCTT
TGCCCACCCAGTGTAATGTCACTGCTCAAATTACATTTCATTACCTTAAAAAGCCAGTCTCTTTTCATAC
TGGCTGTTGGCATTTCTGTAAACTGCCTGTCCATGCTCTTTGTTTTTAAACTTGTTCTTATTGAAAAAAA
AAAAAAAAA -continued SEQ ID NO: 11
Protein sequence of human sMAP (MAp19)
MRLLTLLGLLCGSVATPLGPKWPEPVFGRLASPGFPGEYANDQERRWTLTAPPGYRLRLYFTHFDLELSHL

CEYDFVKLSSGAKVLATLCGQESTDTERAPGKDTFYSLGSSLDITFRSDYSNEKPFTGFEAFYAAEDIDEC

QVAPGEAPTCDHHCHNHLGGFYCSCRAGYVLHRNKRTCSEQSL

SEQ ID NO: 12
cDNA sequence of human sMAP (MAp19)
GGCCAGCTGGACGGGCACACCATGAGGCTGCTGACCCTCCTGGGCCTTCTGTGTGGCTCGGTGGCCACCC

CCTTGGGCCCGAAGTGGCCTGAACCTGTGTTCGGGCGCCTGGCATCCCCCGGCTTTCCAGGGGAGTATGC

CAATGACCAGGAGCGGCGCTGGACCCTGACTGCACCCCCCGGCTACCGCCTGCGCCTCTACTTCACCCAC

TTCGACCTGGAGCTCTCCCACCTCTGCGAGTACGACTTCGTCAAGCTGAGCTCGGGGGCCAAGGTGCTGG

CCACGCTGTGCGGGCAGGAGAGCACAGACACGGAGCGGGCCCCTGGCAAGGACACTTTCTACTCGCTGGG

CTCCAGCCTGGACATTACCTTCCGCTCCGACTACTCCAACGAGAAGCCGTTCACGGGGTTCGAGGCCTTC

TATGCAGCCGAGGACATTGACGAGTGCCAGGTGGCCCCGGGAGAGGCGCCCACCTGCGACCACCACTGCC

ACAACCACCTGGGCGGTTTCTACTGCTCCTGCCGCGCAGGCTACGTCCTGCACCGTAACAAGCGCACCTG

CTCAGAGCAGAGCCTCTAGCCTCCCCTGGAGCTCCGGCCTGCCCAGCAGGTCAGAAGCCAGAGCCAGCCT

GCTGGCCTCAGCTCCGGGTTGGGCTGAGATGGCTGTGCCCCAACTCCCATTCACCCACCATGGACCCAAT

AATAAACCTGGCCCCACCCCAAAAAAAAAAAAAAAAAA

DNA primers:
SEQ ID NO: 13:
5'-gcacccagagccacagtg-3'

SEQ ID NO: 14:
5'-gccttccagtgtgtgggc-3'

SEQ ID NO: 15:
5-gccttccagagtgtggtca-3'

SEQ ID NO: 16:
5'-cgatctggagagcgaactc-3'

SEQ ID NO: 17:
5'-ctgttcttcacactggctg-3'

SEQ ID NO: 18:
5'-ctgctgagatcatgttgttc-3'

SEQ ID NO: 19:
5'-TTATACGACTCACTA-3'

---

The invention claimed is:

1. A pharmaceutical composition comprising a recombinant ficolin-associated polypeptide (FAP), wherein said FAP polypeptide comprises an amino acid sequence set forth in positions 20-380 of SEQ ID NO:1 and having at its C-terminal end the amino acid sequence of SEQ ID NO:4, wherein the FAP polypeptide further comprises a non-native signal sequence, wherein said polypeptide has FAP activity, wherein said polypeptide does not have serine protease activity, and wherein said FAP polypeptide is present in the composition at a concentration of from 0.5 μg/mL to 1 mg/mL.

2. The composition of claim 1, wherein said FAP polypeptide is in homodimer form.

3. The composition of claim 1, wherein said composition comprises at least one of a buffer, a preservative, an isotonic agent, a chelating agent, a stabilizing agent and/or a surfactant.

4. The composition of claim 1, wherein the FAP polypeptide is provided as a conjugate.

5. The composition of claim 1, wherein the FAP polypeptide is N-linked glycosylated at one or two amino acids corresponding to a position selected from 49 and 178 of SEQ ID NO:1.

6. The composition of claim 1, wherein the FAP polypeptide comprises one or more amino acids that have been chemically modified.

7. The composition of claim 6, wherein the chemical modification is selected from the group consisting of alkylation, PEGylation, acylation, ester formation and amide formation.

8. The composition of claim 1, wherein the FAP the polypeptide comprises one or more non-naturally occurring amino acid residues.

9. The composition of claim 8, wherein the non-naturally occurring amino acid residue(s) is selected from the group consisting of: beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine.

* * * * *

UNITED STATES PATENT AND TRADEMARK OFFICE
CERTIFICATE OF CORRECTION

PATENT NO. : 11,203,622 B2
APPLICATION NO. : 15/609660
DATED : December 21, 2021
INVENTOR(S) : Peter Garred It is certified that error appears in the above-identified patent and that said Letters Patent is hereby corrected as shown below:

On the Title Page

In Column 1, item (63), under Related U.S. Application Data, Line 3, delete "2010." and insert -- 2010, now abandoned. --, therefor.

In Column 2, under OTHER PUBLICATIONS, Line 24, delete "Fa-rective" and insert -- Fa-reactive --, therefor.

In Column 2, under OTHER PUBLICATIONS, Line 29, delete "domai,"" and insert -- domain," --, therefor.

In Column 2, under OTHER PUBLICATIONS, Line 30, delete "3pages." and insert -- 3 pages. --, therefor.

In Column 2, under OTHER PUBLICATIONS, Line 35, delete "Comlement-act,"" and insert -- Compliment-act," --, therefor.

On page 2, in Column 1, under OTHER PUBLICATIONS, Line 11, delete "PatentApplication" and insert -- Patent Application --, therefor.

In the Specification

In Column 1, Line 8, delete "15/609,660, filed May 31, 2017," and insert -- 13/383,676, filed July 13, 2012, now abandoned, --, therefor.

In Column 1, Line 9, delete "PCT/EP2010/060,279," and insert -- PCT/EP2010/060279, --, therefor.

In Column 4, Line 18, delete "comprising" and insert -- comprising: --, therefor.

In Column 4, Line 22, delete "the a nucleic" and insert -- the nucleic --, therefor.

Signed and Sealed this
Seventeenth Day of January, 2023

Katherine Kelly Vidal
*Director of the United States Patent and Trademark Office*

CERTIFICATE OF CORRECTION (continued)
U.S. Pat. No. 11,203,622 B2

In Column 8, Line 27, delete "MAP-I" and insert -- MAP-1 --, therefor.

In Column 8, Line 31, delete "MAP-I," and insert -- MAP-1, --, therefor.

In Column 8, Line 31, delete "MAP-I" and insert -- MAP-1 --, therefor.

In Column 8, Line 33, delete "MAP-I" and insert -- MAP-1 --, therefor.

In Column 8, Line 35, delete "MAP-I" and insert -- MAP-1 --, therefor.

In Column 8, Line 37, delete "MAP-I" and insert -- MAP-1 --, therefor.

In Column 8, Line 39, delete "MAP-I" and insert -- MAP-1 --, therefor.

In Column 8, Line 43, delete "MAP-I" and insert -- MAP-1 --, therefor.

In Column 8, Line 46, delete "MAP-I" and insert -- MAP-1 --, therefor.

In Column 8, Line 49, delete "MAP-I" and insert -- MAP-1 --, therefor.

In Column 8, Line 54, delete "MAP-I," and insert -- MAP-1, --, therefor.

In Column 8, Line 58, delete "MAP-I, MASP-I," and insert -- MAP-1, MASP-1, --, therefor.

In Column 9, Line 5, delete "MAP-I" and insert -- MAP-1 --, therefor.

In Column 11, Line 4, delete "posses" and insert -- possess --, therefor.

In Column 12, Line 25, delete "posses" and insert -- possess --, therefor.

In Column 12, Line 29, delete "to or three" and insert -- two or three --, therefor.

In Column 12, Line 39, delete "posses" and insert -- possess --, therefor.

In Column 13, Line 62, delete "Nati." and insert -- Natl. --, therefor.

In Column 18, Line 28, delete "Sci" and insert -- Sci. --, therefor.

In Column 20, Line 2, delete "of the invention of" and insert -- of --, therefor.

In Column 20, Line 13, delete "phosphoamidite" and insert -- phosphoramidite --, therefor.

In Column 20, Line 17, delete "phosphoamidite" and insert -- phosphoramidite --, therefor.

In Column 23, Line 67, delete "eucaryotic cells." and insert -- eukaryotic cells. --, therefor.

In Column 27, Line 26, delete "pro nuclei" and insert -- pronuclei --, therefor.

In Column 27, Line 44, delete "(IEF)," and insert -- (IEF)), --, therefor.

In Column 30, Line 41, delete "ring/ml)" and insert -- mg/ml) --, therefor.

In Column 31, Line 60, delete "a other" and insert -- other --, therefor.

In Column 32, Line 6, delete "aminomethan," and insert -- aminomethane, --, therefor.

In Column 32, Line 17, delete "thiomerosal," and insert -- thiomersal, --, therefor.

In Column 33, Line 13, delete "mg/mi." and insert -- mg/ml. --, therefor.

In Column 35, Line 33, delete "galactopyransoide)," and insert -- galactopyranoside), --, therefor.

In Column 37, Line 28, delete "nanoparticles," and insert -- nanoparticles. --, therefor.

In Column 40, Line 33, delete "according the" and insert -- according to the --, therefor.

In Column 40, Line 35, delete "according the" and insert -- according to the --, therefor.

In Column 40, Line 66, delete "pneumotransmicroscopicsilicovolcanoconiosis," and insert -- pneumonoultramicroscopicsilicovolcanoconiosis, --, therefor.

In Column 41, Line 26, delete "atypic haemolytic" and insert -- atypical hemolytic --, therefor.

In Column 41, Lines 53-54, delete "percutaneous transdermal coronary angioplasty (PTCA)," and insert -- percutaneous transluminal coronary angioplasty (PTCA), --, therefor.

In Column 41, Line 58, delete "septic chock," and insert -- septic shock, --, therefor.

In Column 42, Lines 9-10, delete "percutaneous transdermal coronary angioplasty (PTCA)," and insert -- percutaneous transluminal coronary angioplasty (PTCA), --, therefor.

In Column 44, Line 66, delete "samples wee" and insert -- samples were --, therefor.

In Column 47, Line 15, delete "pad.com" and insert -- pad.com). --, therefor.

In Column 47, Line 28, delete "immunblotting" and insert -- immunoblotting --, therefor.

In Column 47, Line 37, delete "MAP-I" and insert -- MAP-1 --, therefor.

In Column 48, Line 7, delete "MAP-I" and insert -- MAP-1 --, therefor.

In Column 48, Line 43, delete "MAP-I" and insert -- MAP-1 --, therefor.

In Column 48, Line 62, delete "MAP-I" and insert -- MAP-1 --, therefor.

In Column 49, Line 7, delete "MAP-I" and insert -- MAP-1 --, therefor.

In Column 49, Line 9, delete "MAP-I" and insert -- MAP-1 --, therefor.

SEQUENCE LISTING

<160> NUMBER OF SEQ ID NOS: 19

<210> SEQ ID NO 1
<211> LENGTH: 380
<212> TYPE: PRT
<213> ORGANISM: Homo sapiens

<400> SEQUENCE: 1

Met Arg Trp Leu Leu Leu Tyr Tyr Ala Leu Cys Phe Ser Leu Ser Lys
 1               5                  10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

```
Phe Asn Leu Glu Ser Ser Tyr Leu Cys Glu Tyr Asp Tyr Val Lys Val
 65                  70                  75                  80

Glu Thr Glu Asp Gln Val Leu Ala Thr Phe Cys Gly Arg Glu Thr Thr
             85                  90                  95

Asp Thr Glu Gln Thr Pro Gly Gln Glu Val Val Leu Ser Pro Gly Ser
        100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Glu Cys Lys
        130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Lys Asn Glu Ile Asp
        355                 360                 365

Leu Glu Ser Glu Leu Lys Ser Glu Gln Val Thr Glu
        370                 375                 380

<210> SEQ ID NO 2
<211> LENGTH: 1143
<212> TYPE: DNA
<213> ORGANISM: Homo sapiens

<400> SEQUENCE: 2
atgaggtggc tgcttctcta ttatgctctg tgcttctccc tgtcaaaggc ttcagcccac    60
accgtggagc taaacaatat gtttggccag atccagtcgc ctggttatcc agactcctat   120
cccagtgatt cagaggtgac ttggaatatc actgtcccag atgggtttcg gatcaagctt   180
tacttcatgc acttcaactt ggaatcctcc taccttgtg aatatgacta tgtgaaggta   240
gaaactgagg accaggtgct ggcaaccttc tgtggcaggg agaccacaga cacagagcag   300
actcccggcc aggaggtggt cctctcccct ggctccttca tgtccatcac tttccggtca   360
```

```
gatttctcca atgaggagcg tttcacaggc tttgatgccc actacatggc tgtggatgtg    420
gacgagtgca aggagaggga ggacgaggag ctgtcctgtg accactactg ccacaactac    480
attggcggct actactgctc ctgccgcttc ggctacatcc tccacacaga acacaggacc    540
tgccgagtgg agtgcagtga caacctcttc actcaaagga ctggggtgat caccagccct    600
gacttcccaa acccttaccc caagagctct gaatgcctgt ataccatcga gctggaggag    660
ggtttcatgg tcaacctgca gtttgaggac atatttgaca ttgaggacca tcctgaggtg    720
ccctgcccct atgactacat caagatcaaa gttggtccaa aagttttggg gcctttctgt    780
ggagagaaag ccccagaacc catcagcacc cagagccaca gtgtcctgat cctgttccat    840
agtgacaact cgggagagaa ccggggctgg aggctctcat acagggctgc aggaaatgag    900
tgcccagagc tacagcctcc tgtccatggg aaaatcgagc cctcccaagc caagtatttc    960
ttcaaagacc aagtgctcgt cagctgtgac acaggctaca aagtgctgaa ggataatgtg   1020
gagatggaca cattccagat tgagtgtctg aaggatggga cgtggagtaa caagattccc   1080
acctgtaaaa aaatgaaat cgatctggag agcgaactca agtcagagca agtgacagag   1140
tga                                                                 1143

<210> SEQ ID NO 3
<211> LENGTH: 297
<212> TYPE: PRT
<213> ORGANISM: Homo sapiens

<400> SEQUENCE: 3

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220
```

```
Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala
    290                 295

<210> SEQ ID NO 4
<211> LENGTH: 17
<212> TYPE: PRT
<213> ORGANISM: Homo sapiens

<400> SEQUENCE: 4

Lys Asn Glu Ile Asp Leu Glu Ser Glu Leu Lys Ser Glu Gln Val Thr
1               5                   10                  15

Glu

<210> SEQ ID NO 5
<211> LENGTH: 699
<212> TYPE: PRT
<213> ORGANISM: Homo sapiens

<400> SEQUENCE: 5

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Asp Gly Phe Arg Ile Lys Leu Tyr Phe Met His
        50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
```

```
            225                 230                 235                 240
        Pro Cys Pro Tyr Asp Tyr Ile Lys Ile Lys Val Gly Pro Lys Val Leu
                            245                 250                 255
        Gly Pro Phe Cys Gly Glu Lys Ala Pro Glu Pro Ile Ser Thr Gln Ser
                            260                 265                 270
        His Ser Val Leu Ile Leu Phe His Ser Asp Asn Ser Gly Glu Asn Arg
                            275                 280                 285
        Gly Trp Arg Leu Ser Tyr Arg Ala Ala Gly Asn Glu Cys Pro Glu Leu
                            290                 295                 300
        Gln Pro Pro Val His Gly Lys Ile Glu Pro Ser Gln Ala Lys Tyr Phe
        305                 310                 315                 320
        Phe Lys Asp Gln Val Leu Val Ser Cys Asp Thr Gly Tyr Lys Val Leu
                            325                 330                 335
        Lys Asp Asn Val Glu Met Asp Thr Phe Gln Ile Glu Cys Leu Lys Asp
                            340                 345                 350
        Gly Thr Trp Ser Asn Lys Ile Pro Thr Cys Lys Ile Val Asp Cys Arg
                            355                 360                 365
        Ala Pro Gly Glu Leu Glu His Gly Leu Ile Thr Phe Ser Thr Arg Asn
                            370                 375                 380
        Asn Leu Thr Thr Tyr Lys Ser Glu Ile Lys Tyr Ser Cys Gln Glu Pro
        385                 390                 395                 400
        Tyr Tyr Lys Met Leu Asn Asn Asn Thr Gly Ile Tyr Thr Cys Ser Ala
                            405                 410                 415
        Gln Gly Val Trp Met Asn Lys Val Leu Gly Arg Ser Leu Pro Thr Cys
                            420                 425                 430
        Leu Pro Val Cys Gly Leu Pro Lys Phe Ser Arg Lys Leu Met Ala Arg
                            435                 440                 445
        Ile Phe Asn Gly Arg Pro Ala Gln Lys Gly Thr Thr Pro Trp Ile Ala
                            450                 455                 460
        Met Leu Ser His Leu Asn Gly Gln Pro Phe Cys Gly Gly Ser Leu Leu
        465                 470                 475                 480
        Gly Ser Ser Trp Ile Val Thr Ala Ala His Cys Leu His Gln Ser Leu
                            485                 490                 495
        Asp Pro Glu Asp Pro Thr Leu Arg Asp Ser Asp Leu Leu Ser Pro Ser
                            500                 505                 510
        Asp Phe Lys Ile Ile Leu Gly Lys His Trp Arg Leu Arg Ser Asp Glu
                            515                 520                 525
        Asn Glu Gln His Leu Gly Val Lys His Thr Thr Leu His Pro Gln Tyr
                            530                 535                 540
        Asp Pro Asn Thr Phe Glu Asn Asp Val Ala Leu Val Glu Leu Leu Glu
        545                 550                 555                 560
        Ser Pro Val Leu Asn Ala Phe Val Met Pro Ile Cys Leu Pro Glu Gly
                            565                 570                 575
        Pro Gln Gln Glu Gly Ala Met Val Ile Val Ser Gly Trp Gly Lys Gln
                            580                 585                 590
        Phe Leu Gln Arg Phe Pro Glu Thr Leu Met Glu Ile Glu Ile Pro Ile
                            595                 600                 605
        Val Asp His Ser Thr Cys Gln Lys Ala Tyr Ala Pro Leu Lys Lys Lys
                            610                 615                 620
        Val Thr Arg Asp Met Ile Cys Ala Gly Glu Lys Glu Gly Gly Lys Asp
        625                 630                 635                 640
        Ala Cys Ala Gly Asp Ser Gly Gly Pro Met Val Thr Leu Asn Arg Glu
                            645                 650                 655
```

```
Arg Gly Gln Trp Tyr Leu Val Gly Thr Val Ser Trp Gly Asp Asp Cys
            660                 665                 670
Gly Lys Lys Asp Arg Tyr Gly Val Tyr Ser Tyr Ile His His Asn Lys
        675                 680                 685
Asp Trp Ile Gln Arg Val Thr Gly Val Arg Asn
        690                 695

<210> SEQ ID NO 6
<211> LENGTH: 4353
<212> TYPE: DNA
<213> ORGANISM: Homo sapiens

<400> SEQUENCE: 6
gaagtcagcc acacaggata aaggagggaa gggaaggagc agatcttttc ggtaggaaga      60
cagattttgt tgtcaggttc ctgggagtgc aagagcaagt caaaggagag agagaggaga     120
gaggaaaagc cagagggaga gaggggagag ggggatctgt tgcaggcagg ggaaggcgtg     180
acctgaatgg agaatgccag ccaattccag agacacacag ggacctcaga acaaagataa     240
ggcatcacgg acaccacacc gggcacgagc tcacaggcaa gtcaagctgg gaggaccaag     300
gccgggcagc cgggagcacc caaggcagga aaatgaggtg gctgcttctc tattatgctc     360
tgtgcttctc cctgtcaaag gcttcagccc acaccgtgga gctaaacaat atgtttggcc     420
agatccagtc gcctggttat ccagactcct atcccagtga ttcagaggtg acttggaata     480
tcactgtccc agatgggttt cggatcaagc tttacttcat gcacttcaac ttggaatcct     540
cctacctttg tgaatatgac tatgtgaagg tagaaactga ggaccaggtg ctggcaacct     600
tctgtggcag ggagaccaca gacacagagc agactcccgg ccaggaggtg gtcctctccc     660
ctggctcctt catgtccatc actttccggt cagatttctc caatgaggag cgtttcacag     720
gctttgatgc ccactacatg gctgtggatg tggacgagtg caaggagagg gaggacgagg     780
agctgtcctg tgaccactac tgccacaact acattggcgg ctactactgc tcctgccgct     840
tcggctacat cctccacaca gacaacagga cctgccgagt ggagtgcagt gacaacctct     900
tcactcaaag gactggggtg atcaccagcc ctgacttccc aaacccttac cccaagagct     960
ctgaatgcct gtataccatc gagctggagg agggtttcat ggtcaacctg cagtttgagg    1020
acatatttga cattgaggac catcctgagg tgccctgccc ctatgactac atcaagatca    1080 agttggtcc aaaagttttg gggcctttct gtggagagaa agccccagaa cccatcagca    1140
cccagagcca cagtgtcctg atcctgttcc atagtgacaa ctcgggagag aaccggggct    1200
ggaggctctc atacagggct gcaggaaatg agtgcccaga gctacagcct cctgtccatg    1260
ggaaaatcga gccctcccaa gccaagtatt tcttcaaaga ccaagtgctc gtcagctgtg    1320
acacaggcta caaagtgctg aaggataatg tggagatgga cacattccag attgagtgtc    1380
tgaaggatgg gacgtggagt aacaagattc ccacctgtaa aattgtagac tgtagagccc    1440
caggagagct ggaacacggg ctgatcacct tctctacaag gaacaacctc accacataca    1500
agtctgagat caaatactcc tgtcaggagc cctattacaa gatgctcaac aataacacag    1560
gtatatatac ctgttctgcc caaggagtct ggatgaataa agtattgggg agaagcctac    1620
ccacctgcct tccagtgtgt gggctcccca gttctcccg gaagctgatg ccaggatct     1680 tcaatggacg cccagcccag aaaggcacca ctccctggat tgccatgctg tcacacctga    1740
atgggcagcc cttctgcgga ggctccctc taggctccag ctggatcgtg accgccgcac    1800
actgcctcca ccagtcactc gatccggaag atccgacct acgtgattca gacttgctca    1860
```

```
gcccttctga cttcaaaatc atcctgggca agcattggag gctccggtca gatgaaaatg    1920
aacagcatct cggcgtcaaa cacaccactc tccaccccca gtatgatccc aacacattcg    1980
agaatgacgt ggctctggtg gagctgttgg agagcccagt gctgaatgcc ttcgtgatgc    2040
ccatctgtct gcctgaggga ccccagcagg aaggagccat ggtcatcgtc agcggctggg    2100
ggaagcagtt cttgcaaagg ttcccagaga ccctgatgga gattgaaatc ccgattgttg    2160
accacagcac ctgccagaag gcttatgccc cgctgaagaa gaaagtgacc agggacatga    2220
tctgtgctgg ggagaaggaa gggggaaagg acgcctgtgc gggtgactct ggaggcccca    2280
tggtgaccct gaatagagaa agaggccagt ggtacctggt gggcactgtg tcctggggtg    2340
atgactgtgg gaagaaggac cgctacggag tatactctta catccaccac aacaaggact    2400
ggatccagag ggtcaccgga gtgaggaact gaatttggct cctcagcccc agcaccacca    2460
gctgtgggca gtcagtagca gaggacgatc ctccgatgaa agcagccatt tctcctttcc    2520
ttcctcccat cccccctcct tcggcctatc cattactggg caatagagca ggtatcttca    2580
cccccttttc actctcttta agagatggaa gcaagagagt ggtcagaaca caggccgaat    2640
ccaggctcta tcacttacta gtttgcagtg ctgggcaggt gacttcatct cttcgaactt    2700
cagtttcttc ataagatgga aatgctatac cttacctacc tcgtaaaagt ctgatgagga    2760
aaagattaac taatagatgc atagcactta acagagtgca tagcatacac tgtttt caat    2820 aaatgcacct tagcagaagg tcgatgtgtc taccaggcag acgaagctct cttacaaacc    2880
cctgcctggg tcttagcatt gatcagtgac acacctctcc cctcaacctt gaccatctcc    2940
atctgccctt aaatgctgta tgcttttttg ccaccgtgca acttgcccaa catcaatctt    3000
caccctcatc cctaaaaaag taaaacagac aaggttctga gtcctgtggt atgtccccta    3060
gcaaatgtaa ctaggaacat gcactagatg acagattgcg ggagggcctg agagaagcag    3120
ggacaggagg gagcctgggg attgtggttt gggaaggcag acacctggtt ctagaactag    3180
ctctgccctt agccccctgt atgaccctat gcaagtcctc ctccctcatc tcaaagggtc    3240
ctcaaagctc tgacgatcta agatacaatg aagccatttt ccccctgata agatgaggta    3300
aagccaatgt aaccaaaagg caaaaattac aatcggttca aaggaacttt gatgcagaca    3360
aaatgctgct gctgctgctc ctgaaatacc cacccctttc cactacgggt gggttcccaa    3420
ggacatggga caggcaaagt gtgagccaaa ggatccttcc ttattcctaa gcagagcatc    3480
tgctctgggc cctggcctcc ttcccttctt gggaaactgg gctgcatgag gtgggccctg    3540
gtagtttgta ccccaggccc ctatactctt ccttcctatg tccacagctg accccaagca    3600
gccgttcccc gactcctcac ccctgagcct caccctgaac tccctcatct tgcaaggcca    3660
taagtgtttt ccaagcaaaa tgcctctccc atcctctctc aggaagcttc tagagacttt    3720
atgccctcca gagctccaag atataagccc tccaagggat cagaagctcc aagttcctgt    3780
cttctgtttt atagaaattg atcttccctg ggggacttta actcttgacc tgtatgcagc    3840

tgttggagta attccaggtc tcttgaaaaa aagaggaag ataatggaga atgagaacat    3900

атататат attaagcc ccaggctgaa tactcaggga cagcaattca cagcctgcct    3960
ctggttctat aaacaagtca ttctacctct tgtgccctg ctgtttattc tgtaagggaa    4020
aggtggcaat gggacccagc tccatcagac acttgtcaag ctagcagaaa ctccattttc    4080
aatgccaaag aagaactgta atgctgtttt ggaatcatcc caaggcatcc caagacacca    4140

tatcttccca tttcaagcac tgcctgggca caccccaaca tcccaggctg tggtggctcc    4200
```

-continued

```
tgtgggaact acctagatga agagagtatc atttataccct tctaggagct cctattggga    4260
gacatgaaac atatgtaatt gactaccatg taatagaaca aaccctgcca agtgctgctt    4320
tggaaagtca tggaggtaaa agaaagacca ttc                                 4353
```

<210> SEQ ID NO 7
<211> LENGTH: 728
<212> TYPE: PRT
<213> ORGANISM: Homo sapiens

<400> SEQUENCE: 7

```
Met Arg Trp Leu Leu Leu Tyr Tyr Ala Leu Cys Phe Ser Leu Ser Lys
 1               5                  10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350
```

-continued

Gly Thr Trp Ser Asn Lys Ile Pro Thr Cys Lys Ile Val Asp Cys Arg
            355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
        435                 440                 445

Arg Ile Ile Gly Gly Arg Asn Ala Glu Pro Gly Leu Phe Pro Trp Gln
    450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
        515                 520                 525

Ser Gly Ala Val Asn Ser Ser Ala Ala Arg Val Val Leu His Pro Asp
    530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
            580                 585                 590

Trp Gly Ile Ser Asn Pro Asn Val Thr Val Asp Glu Ile Ile Ser Ser
        595                 600                 605

Gly Thr Arg Thr Leu Ser Asp Val Leu Gln Tyr Val Lys Leu Pro Val
    610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
            660                 665                 670

Asp Leu Ser Gln Arg Trp Val Val Gln Gly Leu Val Ser Trp Gly Gly
        675                 680                 685

Pro Glu Glu Cys Gly Ser Lys Gln Val Tyr Gly Val Tyr Thr Lys Val
    690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725

<210> SEQ ID NO 8
<211> LENGTH: 4137
<212> TYPE: DNA
<213> ORGANISM: Homo sapiens

```
<400> SEQUENCE: 8
gaagtcagcc acacaggata aaggagggaa gggaaggagc agatcttttc ggtaggaaga      60
cagattttgt tgtcaggttc ctgggagtgc aagagcaagt caaaggagag agagaggaga     120
gaggaaaagc cagagggaga gaggggggaga ggggatctgt tgcaggcagg ggaaggcgtg    180
acctgaatgg agaatgccag ccaattccag agacacacag ggacctcaga acaaagataa    240
ggcatcacgg acaccacacc gggcacgagc tcacaggcaa gtcaagctgg gaggaccaag    300
gccgggcagc cgggagcacc caaggcagga aaatgaggtg gctgcttctc tattatgctc    360
tgtgcttctc cctgtcaaag gcttcagccc acaccgtgga gctaaacaat atgtttggcc    420
agatccagtc gcctggttat ccagactcct atcccagtga ttcagaggtg acttggaata    480
tcactgtccc agatgggttt cggatcaagc tttacttcat gcacttcaac ttggaatcct    540
cctacctttg tgaatatgac tatgtgaagg tagaaactga ggaccaggtg ctggcaacct    600
tctgtggcag ggagaccaca gacacagagc agactcccgg ccaggaggtg gtcctctccc    660
ctggctcctt catgtccatc actttccggt cagatttctc caatgaggag cgtttcacag    720
gctttgatgc ccactacatg gctgtggatg tggacgagtg caaggagagg gaggacgagg    780
agctgtcctg tgaccactac tgccacaact acattggcgg ctactactgc tcctgccgct    840
tcggctacat cctccacaca gacaacagga cctgccgagt ggagtgcagt gacaacctct    900
tcactcaaag gactggggtg atcaccagcc ctgacttccc aaacccttac cccaagagct    960
ctgaatgcct gtataccatc gagctggagg agggtttcat ggtcaacctg cagtttgagg    1020
acatatttga cattgaggac catcctgagg tgccctgccc ctatgactac atcaagatca    1080
aagttggtcc aaaagttttg gggccttttct gtggagagaa agccccagaa cccatcagca    1140
cccagagcca cagtgtcctg atcctgttcc atagtgacaa ctcgggagag aaccggggct    1200
ggaggctctc atacagggct gcaggaaatg agtgcccaga gctacagcct cctgtccatg    1260
ggaaaatcga gccctcccaa gccaagtatt tcttcaaaga ccaagtgctc gtcagctgtg    1320
acacaggcta caaagtgctg aaggataatg tggagatgga cacattccag attgagtgtc    1380
tgaaggatgg gacgtggagt aacaagattc ccacctgtaa aattgtagac tgtagagccc    1440
caggagagct ggaacacggg ctgatcacct tctctacaag gaacaacctc accacataca    1500
agtctgagat caaatactcc tgtcaggagc cctattacaa gatgctcaac aataacacag    1560
gtatatatac ctgttctgcc caaggagtct ggatgaataa agtattgggg agaagcctac    1620
ccacctgcct tccagagtgt ggtcagcccc ccgctccct gccaagcctg gtcaagagga    1680
tcattggggg ccgaaatgct gagcctggcc tcttcccgtg gcaggccctg atagtggtgg    1740
aggacacttc gagagtgcca aatgacaagt ggtttgggag tggggccctg ctctctgcgt    1800
cctggatcct cacagcagct catgtgctgc gctcccagcg tagagacacc acggtgatac    1860
cagtctccaa ggagcatgtc accgtctacc tgggcttgca tgatgtgcga gacaaatcgg    1920
gggcagtcaa cagctcagct gcccgagtgg tgctccaccc agacttcaac atccaaaact    1980
acaaccacga tatagctctg gtgcagctgc aggagcctgt gcccctggga ccccacgtta    2040
tgcctgtctg cctgccaagg cttgagcctg aaggcccggc cccccacatg ctgggcctgg    2100
tggccggctg gggcatctcc aatcccaatg tgacagtgga tgagatcatc agcagtggca    2160 cacggaccett gtcagatgtc ctgcagtatg tcaagttacc cgtggtgcct cacgctgagt    2220
gcaaaactag ctatgagtcc cgctcgggca attacagcgt cacggagaac atgttctgtg    2280
ctggctacta cgagggcggc aaagacacgt gccttggaga tagcggtggg gccttttgtca   2340
```

```
tctttgatga cttgagccag cgctgggtgg tgcaaggcct ggtgtcctgg ggggacctg    2400 aagaatgcgg cagcaagcag gtctatggag tctacacaaa ggtctccaat tacgtggact    2460
gggtgtggga gcagatgggc ttaccacaaa gtgttgtgga gccccaggtg gaacggtgag    2520
ctgacttact tcctcggggc ctgcctcccc tgagcgaagc tacaccgcac ttccgacagc    2580
acactccaca ttacttatca gaccatatgg aatggaacac actgacctag cggtggcttc    2640
tcctaccgag acagccccca ggaccctgag aggcagagtg tggtataggg aaaaggctcc    2700
aggcaggaga cctgtgttcc tgagcttgtc caagtctctt tccctgtctg ggcctcactc    2760
taccgagtaa tacaatgcag gagctcaacc aaggcctctg tgccaatccc agcactcctt    2820
tccaggccat gcttcttacc ccagtggcct ttattcactc ctgaccactt atcaaaccca    2880
tcggtcctac tgttggtata actgagcttg gacctgacta ttagaaaatg gtttctaaca    2940
ttgaactgaa tgccgcatct gtatattttc ctgctctgcc ttctgggact agccttggcc    3000
taatccttcc tctaggagaa gagcattcag gttttgggag atggctcata gccaagcccc    3060
tctctcttag tgtgatccct tggagcacct tcatgcctgg ggtttctctc ccaaaagctt    3120
cttgcagtct aagccttatc ccttatgttc cccattaaag gaatttcaaa agacatggag    3180
aaagttggga aggtttgtgc tgactgctgg gagcagaata gccgtgggag gcccaccaag    3240
cccttaaatt cccattgtca actcagaaca catttgggcc catatgccac cctggaacac    3300
cagctgacac catgggcgtc cacacctgct gctccagaca agcacaaagc aatctttcag    3360
ccttgaaatg tattatctga aaggctacct gaagcccagg cccgaatatg gggacttagt    3420
cgattacctg gaaaagaaa agacccacac tgtgtcctgc tgtgcttttg ggcaggaaaa    3480
tggaagaaag agtgggggtgg gcacattaga agtcacccaa atcctgccag gctgcctggc    3540
atccctgggg catgagctgg gcggagaatc caccccgcag gatgttcaga gggacccact    3600
ccttcatttt tcagagtcaa aggaatcaga ggctcaccca tggcaggcag tgaaaagagc    3660
caggagtcct gggttctagt ccctgctctg cccccaactg gctgtataac cttttgaaaaa    3720 tcatttttctt tgtctgagtc tctggttctc cgtcagcaac aggctggcat aaggtcccct    3780
gcaggttcct tctagctgga gcactcagag cttccctgac tgctagcagc ctctctggcc    3840
ctcacagggc tgattgttct ccttctccct ggagctctct ctcctgaaaa tctccatcag    3900
agcaaggcag ccagagaagc ccctgagagg gaatgattgg gaagtgtcca ctttctcaac    3960
cggctcatca aacacactcc tttgtctatg aatggcacat gtaaatgatg ttatattttg    4020
tatcttttat atcatatgct tcaccattct gtaaagggcc tctgcattgt tgctcccatc    4080 agggtctca agtggaaata aaccctcgtg gataaccaaa aaaaaaaaaa aaaaaaa      4137
```

<210> SEQ ID NO 9
<211> LENGTH: 686
<212> TYPE: PRT
<213> ORGANISM: Homo sapiens

<400> SEQUENCE: 9

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe

```
                50                  55                  60
Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
                100                 105                 110

Leu Asp Ile Thr Phe Arg Ser Asp Tyr Ser Asn Glu Lys Pro Phe Thr
                115                 120                 125

Gly Phe Glu Ala Phe Tyr Ala Ala Glu Asp Ile Asp Glu Cys Gln Val
                130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
                180                 185                 190

Ser Gly Glu Leu Ser Ser Pro Glu Tyr Pro Arg Pro Tyr Pro Lys Leu
                195                 200                 205

Ser Ser Cys Thr Tyr Ser Ile Ser Leu Glu Glu Gly Phe Ser Val Ile
210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
                260                 265                 270

Thr Val Thr Ile Thr Phe Val Thr Asp Glu Ser Gly Asp His Thr Gly
                275                 280                 285

Trp Lys Ile His Tyr Thr Ser Thr Ala Gln Pro Cys Pro Tyr Pro Met
                290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
                340                 345                 350

Ser Trp Asp Arg Pro Met Pro Ala Cys Ser Ile Val Asp Cys Gly Pro
                355                 360                 365

Pro Asp Asp Leu Pro Ser Gly Arg Val Glu Tyr Ile Thr Gly Pro Gly
                370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
                420                 425                 430

Val Cys Gly Leu Ser Ala Arg Thr Thr Gly Gly Arg Ile Tyr Gly Gly
                435                 440                 445

Gln Lys Ala Lys Pro Gly Asp Phe Pro Trp Gln Val Leu Ile Leu Gly
                450                 455                 460

Gly Thr Thr Ala Ala Gly Ala Leu Leu Tyr Asp Asn Trp Val Leu Thr
465                 470                 475                 480
```

```
Ala Ala His Ala Val Tyr Glu Gln Lys His Asp Ala Ser Ala Leu Asp
            485                 490                 495
Ile Arg Met Gly Thr Leu Lys Arg Leu Ser Pro His Tyr Thr Gln Ala
        500                 505                 510
Trp Ser Glu Ala Val Phe Ile His Glu Gly Tyr Thr His Asp Ala Gly
        515                 520                 525
Phe Asp Asn Asp Ile Ala Leu Ile Lys Leu Asn Asn Lys Val Val Ile
    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                565                 570                 575
Gln Arg Gly Phe Leu Ala Arg Asn Leu Met Tyr Val Asp Ile Pro Ile
            580                 585                 590
Val Asp His Gln Lys Cys Thr Ala Ala Tyr Glu Lys Pro Pro Tyr Pro
        595                 600                 605
Arg Gly Ser Val Thr Ala Asn Met Leu Cys Ala Gly Leu Glu Ser Gly
        610                 615                 620
Gly Lys Asp Ser Cys Arg Gly Asp Ser Gly Gly Ala Leu Val Phe Leu
625                 630                 635                 640
Asp Ser Glu Thr Glu Arg Trp Phe Val Gly Gly Ile Val Ser Trp Gly
                645                 650                 655
Ser Met Asn Cys Gly Glu Ala Gly Gln Tyr Gly Val Tyr Thr Lys Val
            660                 665                 670
Ile Asn Tyr Ile Pro Trp Ile Glu Asn Ile Ile Ser Asp Phe
        675                 680                 685

<210> SEQ ID NO 10
<211> LENGTH: 2460
<212> TYPE: DNA
<213> ORGANISM: Homo sapiens

<400> SEQUENCE: 10
ggccagctgg acgggcacac catgaggctg ctgacccctcc tgggccttct gtgtggctcg      60
gtggccaccc ccttgggccc gaagtggcct gaacctgtgt tcgggcgcct ggcatccccc     120
ggctttccag gggagtatgc caatgaccag gagcggcgct ggaccctgac tgcaccccccc   180
ggctaccgcc tgcgcctcta cttcacccac ttcgacctgg agctctccca cctctgcgag     240
tacgacttcg tcaagctgag ctcgggggcc aaggtgctgg ccacgctgtg cgggcaggag     300
agcacagaca cggagcgggc ccctggcaag gacactttct actcgctggg ctccagcctg     360
gacattacct tccgctccga ctactccaac gagaagccgt tcacggggtt cgaggccttc     420
tatgcagccg aggacattga cgagtgccag gtggccccgg agaggcgcc cacctgcgac     480
caccactgcc acaaccacct gggcggtttc tactgctcct gccgcgcagg ctacgtcctg     540
caccgtaaca agcgcacctg ctcagccctg tgctccggcc aggtcttcac ccagaggtct     600
ggggagctca gcagccctga atacccacgg ccgtatccca actctccag ttgcacttac     660
agcatcagcc tggaggaggg gttcagtgtc attctggact tgtgtgagtc cttcgatgtg     720
gagacacacc ctgaaaccct gtgtccctac gactttctca gattcaaac agacagagaa     780
gaacatggcc cattctgtgg gaagacattg cccccacagga ttgaaacaaa agcaacacg     840
gtgaccatca cctttgtcac agatgaatca ggagaccaca caggctggaa gatccactac     900
acgagcacag cgcagccttg cccttatccg atggcgccac ctaatggcca cgtttcacct     960
```

```
gtgcaagcca aatacatcct gaaagacagc ttctccatct tttgcgagac tggctatgag    1020
cttctgcaag tcacttgcc cctgaaatcc tttactgcag tttgtcagaa agatggatct    1080
tgggaccggc caatgcccgc gtgcagcatt gttgactgtg ccctcctga tgatctaccc    1140 agtggccgag tggagtacat cacaggtcct ggagtgacca cctacaaagc tgtgattcag    1200
tacagctgtg aagagacctt ctacacaatg aaagtgaatg atggtaaata tgtgtgtgag    1260
gctgatggat tctggacgag ctccaaagga gaaaaatcac tcccagtctg tgagcctgtt    1320
tgtggactat cagcccgcac aacaggaggg cgtatatatg gagggcaaaa ggcaaaacct    1380
ggtgattttc cttggcaagt cctgatatta ggtggaacca cagcagcagg tgcactttta    1440
tatgacaact gggtcctaac agctgctcat gccgtctatg agcaaaaaca tgatgcatcc    1500
gccctggaca ttcgaatggg caccctgaaa agactatcac ctcattatac acaagcctgg    1560
tctgaagctg ttttatatca tgaaggttat actcatgatg ctggctttga caatgacata    1620
gcactgatta aattgaataa caaagttgta atcaatagca acatcacgcc tatttgtctg    1680
ccaagaaaag aagctgaatc ctttatgagg acagatgaca ttggaactgc atctggatgg    1740
ggattaaccc caaagggttt tcttgctaga aatctaatgt atgtcgacat accgattgtt    1800
gaccatcaaa aatgtactgc tgcatatgaa aagccaccct atccaagggg aagtgtaact    1860
gctaacatgc tttgtgctgg cttagaaagt gggggcaagg acagctgcag aggtgacagc    1920 ggagggcac tggtgtttct agatagtgaa acagagaggt ggtttgtggg aggaatagtg    1980 tcctgggggtt ccatgaattg tggggaagca ggtcagtatg gagtctacac aaaagttatt    2040
aactatattc cctggatcga gaacataatt agtgattttt aacttgcgtg tctgcagtca    2100
aggattcttc attttttagaa atgcctgtga agaccttggc agcgacgtgg ctcgagaagc    2160
attcatcatt actgtggaca tggcagttgt tgctccaccc aaaaaaacag actccaggtg    2220
aggctgctgt catttctcca cttgccagtt taattccagc cttacccatt gactcaaggg    2280
gacataaacc acgagagtga cagtcatctt tgcccaccca gtgtaatgtc actgctcaaa    2340
ttacatttca ttaccttaaa aagccagtct cttttcatac tggctgttgg catttctgta    2400
aactgcctgt ccatgctctt tgtttttaaa cttgttctta ttgaaaaaaa aaaaaaaaaa    2460
```

<210> SEQ ID NO 11
<211> LENGTH: 185
<212> TYPE: PRT
<213> ORGANISM: Homo sapiens

<400> SEQUENCE: 11

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

```
Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
        130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
        180                 185

<210> SEQ ID NO 12
<211> LENGTH: 738
<212> TYPE: DNA
<213> ORGANISM: Homo sapiens

<400> SEQUENCE: 12
ggccagctgg acgggcacac catgaggctg ctgaccctcc tgggccttct gtgtggctcg      60
gtggccaccc ccttgggccc gaagtggcct gaacctgtgt tcgggcgcct ggcatccccc     120
ggctttccag gggagtatgc caatgaccag gagcggcgct ggaccctgac tgcaccccc     180 ggctaccgcc tgcgcctcta cttcacccac ttcgacctgg agctctccca cctctgcgag     240
tacgacttcg tcaagctgag ctcggggggcc aaggtgctgg ccacgctgtg cgggcaggag     300
agcacagaca cggagcgggc ccctggcaag gacactttct actcgctggg ctccagcctg     360
gacattacct tccgctccga ctactccaac gagaagccgt tcacggggtt cgaggccttc     420
tatgcagccg aggacattga cgagtgccag gtggccccgg agaggcgcc cacctgcgac     480 caccactgcc acaaccacct gggcggtttc tactgctcct gccgcgcagg ctacgtcctg     540
caccgtaaca agcgcacctg ctcagagcag agcctctagc ctccctgga gctccggcct     600 gcccagcagg tcagaagcca gagccagcct gctggcctca gctccgggtt gggctgagat     660
ggctgtgccc caactcccat tcacccacca tggacccaat aataaacctg ccccacccc      720 aaaaaaaaaa aaaaaaaa                                                   738

<210> SEQ ID NO 13
<211> LENGTH: 18
<212> TYPE: DNA
<213> ORGANISM: Artificial Sequence
<220> FEATURE:
<223> OTHER INFORMATION: DNA primer

<400> SEQUENCE: 13
gcacccagag ccacagtg                                                    18

<210> SEQ ID NO 14
<211> LENGTH: 18
<212> TYPE: DNA
<213> ORGANISM: Artificial Sequence
<220> FEATURE:
<223> OTHER INFORMATION: DNA Primer

<400> SEQUENCE: 14
gccttccagt gtgtgggc                                                    18

<210> SEQ ID NO 15
<211> LENGTH: 19
<212> TYPE: DNA
<213> ORGANISM: Artificial Sequence
```

```
<220> FEATURE:
<223> OTHER INFORMATION: DNA Primer

<400> SEQUENCE: 15
gccttccaga gtgtggtca                                              19

<210> SEQ ID NO 16
<211> LENGTH: 19
<212> TYPE: DNA
<213> ORGANISM: Artificial Sequence
<220> FEATURE:
<223> OTHER INFORMATION: DNA Primer

<400> SEQUENCE: 16
cgatctggag agcgaactc                                              19

<210> SEQ ID NO 17
<211> LENGTH: 19
<212> TYPE: DNA
<213> ORGANISM: Artificial Sequence
<220> FEATURE:
<223> OTHER INFORMATION: DNA Primer

<400> SEQUENCE: 17
ctgttcttca cactggctg                                              19

<210> SEQ ID NO 18
<211> LENGTH: 20
<212> TYPE: DNA
<213> ORGANISM: Artificial Sequence
<220> FEATURE:
<223> OTHER INFORMATION: DNA Primer

<400> SEQUENCE: 18
ctgctgagat catgttgttc                                             20

<210> SEQ ID NO 19
<211> LENGTH: 15
<212> TYPE: DNA
<213> ORGANISM: Artificial Sequence
<220> FEATURE:
<223> OTHER INFORMATION: DNA Primer

<400> SEQUENCE: 19
ttatacgact cacta                                                  15
```